United States Patent

Komori et al.

[11] Patent Number: 5,998,333
[45] Date of Patent: Dec. 7, 1999

[54] PYRIMIDINONE DERIVATIVES AND HERBICIDES CONTAINING THEM

[75] Inventors: Takashi Komori; Hisayuki Hoshi, both of Toyonaka, Japan

[73] Assignee: Sumitomo Chemical Company, Ltd., Osaka-fu, Japan

[21] Appl. No.: 09/148,403

[22] Filed: Sep. 4, 1998

[30] Foreign Application Priority Data

Sep. 5, 1997 [JP] Japan ................................. 9-241573
Nov. 28, 1997 [JP] Japan ................................. 9-370043

[51] Int. Cl.⁶ .................... A01N 43/54; C07D 487/04; C07D 239/70
[52] U.S. Cl. .................... 504/240; 504/241; 544/279; 544/281; 544/282
[58] Field of Search .................... 544/279, 281, 544/282; 504/240, 241

[56] References Cited

U.S. PATENT DOCUMENTS

| 3,816,422 | 6/1974 | Stable et al. ............... 260/256.4 |
| 5,602,077 | 2/1997 | Amuti et al. ............... 504/243 |

FOREIGN PATENT DOCUMENTS

| 0476697 A1 | 3/1992 | European Pat. Off. . |
| WO9814452 A1 | 4/1998 | WIPO . |

OTHER PUBLICATIONS

Stahle et al., *Liebigs Ann. Chem*, pp. 1275–1281 (1973) (w/Abstract).
von Hans Peter Harter et al., *Helvetica Chimica Acta*, vol. 59, Fasc. 4, No. 122, pp. 1203–1212 (w/Abstract).

*Primary Examiner*—Mukund J. Shah
*Assistant Examiner*—Ann M. Kessinger
*Attorney, Agent, or Firm*—Birch, Stewart, Kolasch & Birch, LLP

[57] ABSTRACT

Pyrimidinone derivatives of the general formula:

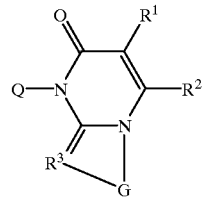

wherein $R^1$ is hydrogen or alkyl; $R^2$ is haloalkyl; $R^3$ is nitrogen or CH; G is optionally substituted ethylene, trimethylene, or vinylene; and Q is selected from several heterocyclic-condensed phenyl groups, are useful as the active ingredients of herbicides because of their excellent herbicidal activity.

12 Claims, No Drawings

PYRIMIDINONE DERIVATIVES AND HERBICIDES CONTAINING THEM

FIELD OF INVENTION

The present invention relates to pyrimidinone derivatives and their use.

OBJECT OF THE INVENTION

It is an object of the present invention to provide compounds with excellent herbicidal activity.

SUMMARY OF THE INVENTION

The present inventors have intensively studied to seek out various compounds with excellent herbicidal activity. As a result, they have found that pyrimidinone derivatives of the general formula as depicted below have excellent herbicidal activity, thereby completing the present invention.

Thus the present invention provides pyrimidinone derivatives of the general formula:

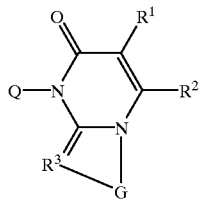

(hereinafter referred to as the present compound(s))

wherein:

$R^1$ is hydrogen or $C_1$–$C_3$ alkyl;

$R^2$ is $C_1$–$C_3$ haloalkyl;

$R^3$ is nitrogen or CH;

G is any group of the general formula:

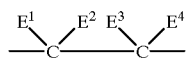
G-1

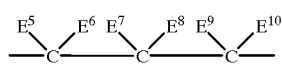
G-2

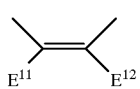
G-3 wherein:

$E^1$, $E^2$, $E^3$, $E^4$, $E^5$, $E^6$, $E^7$, $E^8$, $E^9$, $E^{10}$, $E^{11}$, and $E^{12}$ are independently hydrogen or $C_1$–$C_3$ alkyl; and Q is any group of the general formula:

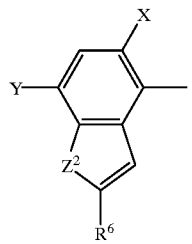
Q-3

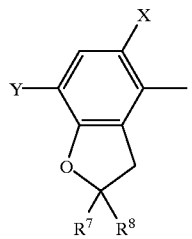
Q-4 wherein:

X is hydrogen or halogen;

Y is halogen, nitro, cyano, or trifluoromethyl;

$Z^2$ is oxygen or sulfur;

$R^6$ is $C_1$–$C_6$ alkyl, $C_1$–$C_6$ haloalkyl, cyano, carboxyl, hydroxy $C_1$–$C_6$ alkyl, $C_1$–$C_6$ alkoxy $C_1$–$C_6$ alkyl, $C_1$–$C_4$ alkylthio $C_1$–$C_4$ alkyl, $C_1$–$C_6$ alkoxy $C_1$–$C_6$ alkoxy $C_1$–$C_6$ alkyl, ($C_1$–$C_6$ alkyl)carbonyloxy $C_1$–$C_6$ alkyl, ($C_1$–$C_6$ haloalkyl)carbonyloxy $C_1$–$C_6$ alkyl, or ($C_1$–$C_6$ alkoxy)carbonyl;

$R^7$ is hydrogen or $C_1$–$C_6$ alkyl; and $R^8$ is $C_1$–$C_6$ alkyl, $C_1$–$C_6$ haloalkyl, hydroxy $C_1$–$C_6$ alkyl, $C_1$–$C_4$ alkoxy $C_1$–$C_4$ alkyl, $C_1$–$C_3$ alkoxy $C_1$–$C_3$ alkoxy $C_1$–$C_3$ alkyl, ($C_1$–$C_6$ alkyl)carbonyloxy $C_1$–$C_6$ alkyl, ($C_1$–$C_6$ haloalkyl)carbonyl $C_1$–$C_6$ alkyl, carboxyl, carboxy $C_1$–$C_6$ alkyl, ($C_1$–$C_8$ alkoxy)carbonyl, ($C_1$–$C_6$ haloalkoxy)carbonyl, ($C_3$–$C_{10}$ cycloalkoxy)carbonyl, ($C_3$–$C_8$ alkenyloxy)carbonyl, ($C_3$–$C_8$ alkynyloxy)carbonyl, ($C_1$–$C_6$ alkyl)aminocarbonyl, di($C_1$–$C_6$ alkyl)aminocarbonyl, ($C_1$–$C_6$ alkyl)aminocarbonyloxy $C_1$–$C_6$ alkyl, or di($C_1$–$C_6$ alkyl)aminocarbonyloxy $C_1$–$C_6$ alkyl;

and herbicides containing them as active ingredients.

DETAILED DESCRIPTION OF THE INVENTION

The $C_1$–$C_3$ alkyl represented by $R^1$ may include methyl and ethyl.

The $C_1$–$C_3$ haloalkyl represented by $R^2$ may include trichloromethyl, trifluoromethyl, chlorodifluoromethyl, pentafluoroethyl, and 1,1-difluoroethyl.

The $C_1$–$C_3$ alkyl represented by $E^1$, $E^2$, $E^3$, $E^4$, $E^5$, $E^6$, $E^7$, $E^8$, $E^9$, $E^{10}$, $E^{11}$, or $E^{12}$ may include methyl, ethyl, propyl, and isopropyl.

The halogen, represented by X or Y may include fluorine, chlorine, bromine, and iodine.

The $C_1$–$C_6$ alkyl represented by $R^6$ may include methyl and ethyl.

The $C_1$–$C_6$ haloalkyl represented by $R^6$ may include bromomethyl, dibromomethyl, tribromomethyl, 1-bromoethyl, chloromethyl, dichloromethyl, and trichloromethyl.

The hydroxy $C_1$–$C_6$ alkyl represented by $R^6$ may include hydroxymethyl and hydroxyethyl.

The ($C_1$–$C_6$ alkoxy) $C_1$–$C_6$ alkyl represented by $R^6$ may include methoxymethyl, ethoxymethyl, propoxymethyl, and isopropoxymethyl.

The $C_1$–$C_4$ alkylthio $C_1$–$C_4$ alkyl represented by $R^6$ may include methylthiomethyl, 1-methylthioethyl, and ethylthiomethyl.

The {($C_1$–$C_6$ alkoxy) $C_1$–$C_6$ alkoxy} $C_1$–$C_6$ alkyl represented by $R^6$ may include methoxymethoxymethyl, methoxyethoxymethyl, and ethoxymethoxymethyl.

The ($C_1$–$C_6$ alkyl)carbonyloxy $C_1$–$C_6$ alkyl represented by $R^6$ may include acetyloxymethyl, ethylcarbonyloxymethyl, and isopropylcarbonyloxymethyl.

The ($C_1$–$C_6$ haloalkyl)carbonyloxy $C_1$–$C_6$ alkyl represented by $R^6$ may include trifluoroacetyloxymethyl, chloroacetyloxymethyl, and trichloroacetyloxymethyl.

The ($C_1$–$C_6$ alkoxy)carbonyl represented by $R^6$ may include methoxycarbonyl, ethoxycarbonyl, propoxycarbonyl, butoxycarbonyl, amyloxycarbonyl, isopropoxycarbonyl, isobutoxycarbonyl, and isoamyloxycarbonyl.

The $C_1$–$C_6$ alkyl represented by $R^7$ may include methyl and ethyl.

The $C_1$–$C_6$ alkyl represented by $R^8$ may include methyl and ethyl.

The $C_1$–$C_6$ haloalkyl represented by $R^8$ may include chloromethyl and bromomethyl.

The hydroxy $C_1$–$C_6$ alkyl represented by $R^8$ may include hydroxymethyl.

The $C_1$–$C_4$ alkoxy $C_1$–$C_4$ alkyl represented by $R^8$ may include methoxymethyl, ethoxymethyl, isopropoxymethyl, butoxymethyl, and isobutoxymethyl.

The $C_1$–$C_3$ alkoxy $C_1$–$C_3$ alkoxy $C_1$–$C_3$ alkyl represented by $R^8$ may include methoxymethoxymethyl, methoxyethoxymethyl, ethoxymethoxymethyl.

The ($C_1$–$C_6$ alkyl)carbonyloxy $C_1$–$C_6$ alkyl represented by $R^8$ may include acetyloxymethyl, ethylcarbonyloxymethyl, and isopropylcarbonyloxymethyl.

The ($C_1$–$C_6$ haloallyl)carbonyl $C_1$–$C_6$ alkyl represented by $R^8$ may include 2-choroethylcarbonylmethyl.

The carboxy $C_1$–$C_6$ alkyl represented by $R^8$ may include carboxymethyl and carboxyethyl.

The ($C_1$–$C_8$ alkoxy)carbonyl represented by $R^8$ may include methoxycarbonyl, ethoxyearbonyl, propoxycarbonyl, butoxycarbonyl, amyloxycarbonyl, isopropoxycarbonyl, isobutoxycarbonyl, and isoamyloxycarbonyl.

The ($C_1$–$C_6$ haloalkoxy)carbonyl represented by $R^8$ may include 2-chloroethoxycarbonyl, 2-bromoethoxycarbonyl, 3-chlorobutoxycarbonyl, 1-chloro-2-propoxycarbonyl, 1,3-dichloro-2-propoxycarbonyl, 2,2-dichloroethoxycarbonyl, 2,2,2-trifluoroethoxycarbonyl, 2,2,2-trichloroethoxycarbonyl, and 2,2,2-tribromoethoxycarbonyl.

The ($C_3$–$C_{10}$ cycloalkoxy)carbonyl represented by $R^8$ may include cyclobutyloxycarbonyl, cyclopentyloxycarbonyl, and cyclohexyloxycarbonyl.

The ($C_3$–$C_8$ alkenyloxy)carbonyl represented by $R^8$ may include allyloxycarbonyl, 3-butenyloxycarbonyl, and 1-methyl-2-propenyloxycarbonyl.

The ($C_3$–$C_8$ alkynyloxy)carbonyl represented by $R^8$ may include propargyloxycarbonyl, 3-butynyloxycarbonyl, and 1-methyl-2-propynyloxycarbonyl.

The ($C_1$–$C_6$ alkyl)aminocarbonyl represented by $R^8$ may include methylaminocarbonyl, ethylaminocarbonyl, and propylaminocarbonyl.

The di($C_1$–$C_6$ alkyl)aminocarbonyl represented by $R^8$ may include dimethylaminocarbonyl, diethylaminocarbonyl, and diisopropylaminocarbonyl.

The ($C_1$–$C_6$ alkyl)aminocarbonyloxy $C_1$–$C_6$ alkyl represented by $R^8$ may include methylaminocarbonyloxymethyl, ethylaminocarbonyloxymethyl, and propylaminocarbonyloxymethyl.

The di($C_1$–$C_6$ alkyl)aminocarbonyloxy $C_1$–$C_6$ alkyl represented by $R^8$ may include dimethylaminocarbonyloxymethyl and diethylaminocarbonyloxymethyl.

For the present compounds, there may exist geometrical isomers based on the double bond, and optical isomers or diastereomers based on the asymmetric carbon atom. These isomers and their mixtures are included in the present compounds.

In the present compounds, the substituent groups preferred in view of herbicidal activity may include fluorine-substituted methyl (e.g., trifluoromethyl, chlorodifluoromethyl) and fluorine-substituted ethyl (e.g., pentafluoroethyl, 1,1-difluoroethyl) for $R^2$; hydrogen and methyl for $R^1$; nitrogen for $R^3$; $C_1$–$C_6$ alkyl (e.g., methyl, ethyl), carboxyl, hydroxy $C_1$–$C_6$ alkyl (e.g., hydroxy methyl) and ($C_1$–$C_6$ alkoxy)carbonyl (e.g., methoxycarbonyl, ethoxycarbonyl) for $R^6$; hydrogen and methyl for $R^7$; and $C_1$–$C_6$ alkyl (e.g., methyl, ethyl), hydroxy $C_1$–$C_6$ alkyl (e.g., hydroxy methyl), ($C_1$–$C_8$ alkoxy)carbonyl (e.g., methoxycarbonyl, ethoxycarbonyl) for $R^8$.

The following are specific examples of the preferred compounds of the present invention in view of herbicidal activity. The numbers in parentheses after the compound names are corresponding to the compound numbers in Tables 1 to 92.

8-(7-chloro-5-fluoro-2-methyl-2,3-dihydrobenzo[b]furan-4-yl)-5-(trifluoromethyl)-2,3,7,8-tetrahydroimidazo[1,2-a]pyrimidin-7-one (4-5)

8-[7-chloro-5-fluoro-2-(hydroxymethyl)-2,3-dihydrobenzo[b]furan-4-yl]-5-(trifluoromethyl)-2,3,7,8-tetrahydroimidazo[1,2-a]pyrimidin-7-one (4-14)

methyl 7-chloro-5-fluoro-4-[7-oxo-5-(trifluoromethyl)-2,3,7,8-tetrahydroimidazo [1,2-a]pyrimidin-8-yl]-2,3-dihydrobenzo[b]furan-2-carboxylate (4-106)

ethyl 7-chloro-5-fluoro-4-[7-oxo-5-(trifluoromethyl)-2,3,7,8-tetrahydroimidazo[1,2-a]pyrimidin-8-yl]-2,3-dihydrobenzo[b]furan-2-carboxylate (4-112)

8-(7-chloro-5-fluoro-2,2-dimethyl-2,3-dihydrobenzo[b]furan-4-yl)-5-(trifluoromethyl)-2,3,7,8-tetrahydroimidazo[1,2-a]pyrimidin-7-one (4-197)

methyl 7-chloro-5-fluoro-2-methyl-4-[7-oxo-5-(trifluoromethyl)-2,3,7,8-tetrahydroimidazo[1,2-a]pyrimidin-8-yl]-2,3-dihydrobenzo[b]furan-2-carboxylate (4-298)

ethyl 7-chloro-5-fluoro-2-methyl-4-[7-oxo-5-(trifluoromethyl)-2,3,7,8-tetrahydroimidazo[1,2-a]pyrimidin-8-yl]-2,3-dihydrobenzo[b]furan-2-carboxylate (4-304)

8-(7-chloro-5-fluoro-2-methylbenzo[b]furan-4-yl)-5-(trifluoromethyl)-2,3,7,8-tetrahydroimidazo[1,2-a]pyrimidin-7-one (3-5)

8-[7-chloro-5-fluoro-2-(hydroxymethyl)benzo[b]furan-4-yl]-5-(trifluoromethyl)-2,3,7,8-tetrahydroimidazo[1,2-a]pyrimidin-7-one (3-52)

methyl 7-chloro-5-fluoro-4-[7-oxo-5-(trifluoromethyl)-2,3,7,8-tetrahydroimidazo[1,2-a]pyrimidin-8-yl]benzo[b]furan-2-carboxylate (3-130)

ethyl 7-chloro-5-fluoro-4-[7-oxo-5-(trifluoromethyl)-2,3,7,8-tetrahydroimidazo[1,2-a]pyrimidin-8-yl]benzo[b]furan-2-carboxylate (3-136)

8-(7-chloro-5-fluoro-2-methyl-2,3-dihydrobenzo[b]furan-4-yl)-5-(trifluoromethyl)-7,8-dihydroimidazo[1,2-a]pyrimidin-7-one (9-5)

8-[7-chloro-5-fluoro-2-(hydroxymethyl)-2,3-dihydrobenzo[b]furan-4-yl]-5-(trifluoromethyl)-7,8-dihydroimidazo[1,2-a]pyrimidin-7-one (9-14)

methyl 7-chloro-5-fluoro-4-[7-oxo-5-(trifluoromethyl)-7,8-dihydroimidazo[1,2-a]pyrimidin-8-yl]-2,3-dihydrobenzo[b]furan-2-carboxylate (9-106)

ethyl 7-chloro-5-fluoro-4-[7-oxo-5-(trifluoromethyl)-7,8-dihydroimidazo[1,2-a]pyrimidin-8-yl]-2,3-dihydrobenzo[b]furan-2carboxylate (9-112)

8-(7-chloro-5-fluoro-2,2-dimethyl-2,3-dihydrobenzo[b]furan-4-yl)-5-(trifluoromethyl)-7,8-dihydroimidazo[1,2-a]pyrimidin-7-one (9-197)

methyl 7-chloro-5-fluoro-2-methyl-4-[7-oxo-5-(trifluoromethyl)-7,8-dihydroimidazo[1,2-a]pyrimidin-8-yl]-2,3-dihydrobenzo[b]furan-2 -carboxylate (9-298)

ethyl 7-chloro-5-fluoro-2-methyl-4-[7-oxo-5-(trifluoromethyl)-7,8-dihydroimidazo[1,2-a]pyrimidin-8-yl]-2,3-dihydrobenzo[b]furan-2-carboxylate (9-304)

8-(7-chloro-5-fluoro-2-methylbenzo[b]furan-4-yl)-5-(trifluoromethyl)-7,8-dihydroimidazo[1,2-a]pyrimidin-7-one (8-5)

8-[7-chloro-5-fluoro-2-(hydroxymethyl)benzo[b]furan-4-yl]-5-(trifluoromethyl)-7,8-dihydroimidazo[1,2-a]pyrimidin-7-one (8-52)

methyl 7-chloro-5-fluoro-4-[7-oxo-5-(trifluoromethyl)-7,8-dihydroimidazo[1,2-a]pyrimidin-8-yl]benzo[b]furan-2-carboxylate (8-130)

ethyl 7-chloro-5-fluoro-4-[7-oxo-5-(trifluoromethyl)-7,8-dihydroimidazo[1,2-a]pyrimidin-8-yl]benzo[b]furan-2-carboxylate (8-136)

The present compounds can be produced, for example, according to the following production processes 1 to 5.

Production Process 1

This is the production process in which an aniline derivative of the general formula:

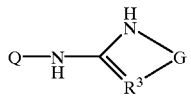

wherein G, Q, and $R^3$ are as defined above, is reacted with an ester derivative of the general formula:

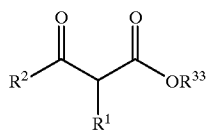

wherein $R^1$ and $R^2$ are as defined above and $R^{33}$ is $C_1$–$C_6$ alkyl, or an acrylic acid derivative of the general formula:

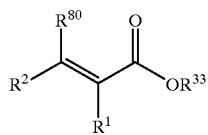

wherein $R^1$, $R^2$, and $R^{33}$ are as defined above and $R^{80}$ is a leaving group such as $C_1$–$C_6$ alkoxy, $C_1$–$C_6$ alkylthio, di($C_1$–$C_3$ alkyl)amino, halogen, $C_1$–$C_6$ alkylsulfonyl, or arylsulfonyl.

The reaction is usually effected without any solvent or in a solvent. The reaction temperature is usually in the range of 50° C. to 200° C. The reaction time is usually in the range of 1 to 100 hours.

The amounts of reagents to be used in the reaction are stoichiometrically 1 mole of the ester derivative or acrylic acid derivative of the above general formula for 1 mole of the aniline derivative of the above general formula, although they may suitably be changed with the reaction conditions.

The solvent which can be used may include aliphatic hydrocarbons such as hexane, heptane, octane, and ligroin; aromatic hydrocarbons such as benzene, toluene, ethylbenzene, xylene, and mesitylene; halogenated hydrocarbons such as chlorobenzene, dichlorobenzene, and trichlorobenzene; ethers such as 1,4-dioxane, tetrahydrofuran, ethylene glycol dimethyl ether, and methyl t-butyl ether; nitro compounds such as nitromethane and nitrobenzene; acid amides such as N,N-dimethylformamide; sulfur compounds such as dimethylsulfoxide and sulforane; and mixtures thereof.

Furthermore, acids such as p-toluenesulfonic acid may be used as the catalyst in the reaction.

After completion of the reaction, the reaction mixture is concentrated without further treatment, or the reaction mixture is poured into water, which is extracted with an organic solvent, and the organic layer is subjected to ordinary post-treatments such as drying and concentration. If necessary, purification may be carried out by an ordinary technique such as recrystallization or column chromatography. Thus the desired present compound can be obtained.

Production Process 2

This is the production process according to the following scheme:

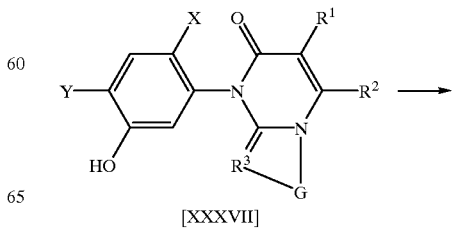

[XXXVII]

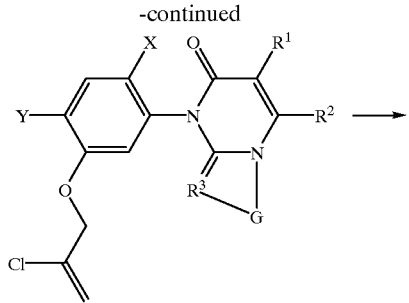

[XL]

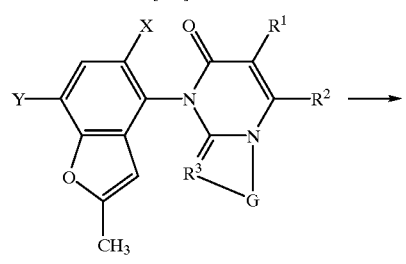

[XLI]

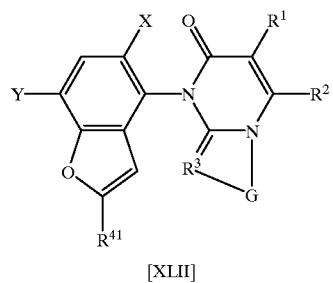

[XLII]

wherein $R^{41}$ is as defined for $R^6$ but not methyl, and X, Y, G, $R^1$, $R^2$, and $R^3$ are as defined above.

The reaction conditions in the respective steps are, foe example, as follows:

1) Procedure for preparing compound [XL] from compound [XXXVII]

Compound [XL] can be prepared by reacting compound [XXXVII] with 2,3-dichloropropene in the presence of a base in a solvent.

Amount of 2,3-dichloropropene: 1 to 3 moles for 1 mole of compound [XXXVII]

Base: inorganic bases such as potassium carbonate

Amount of base: 1 to 2 moles for 1 mole of compound [XXXVII]

Solvent: DMF or the like

Temperature: 0° C. to 70° C.

Time: a moment to 24 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

2) Procedure for preparing compound [XLI] from compound [XL]

Compound [XLI] can be prepared by heating compound [XL] in a solvent

Solvent: DMF, N,N-dimethylaniline, N,N-diethylaniline, or the like

Temperature: 70° C. to 200° C.

Time: a moment to 24 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

3) Procedure for preparing compound [XLII] from compound [XLI]

The reaction can be effected by the procedure for converting methyl at position 2 on the benzofuran ring into another substituent group, as described on column 2–11 in the specification of U.S. Pat. No. 5,308,829.

Production Process 3

This is the production process according the following scheme:

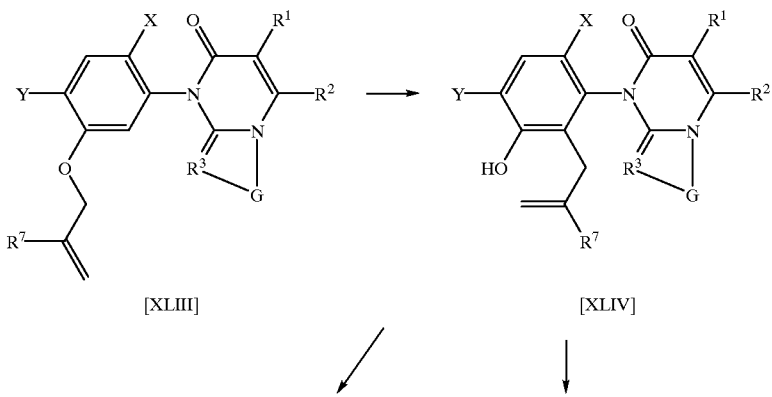

[XLIII]  [XLIV]

-continued

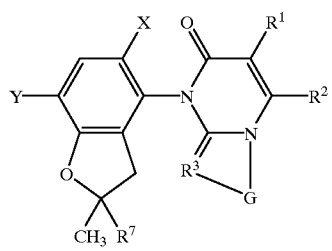

[XLV]

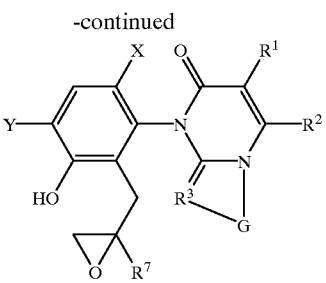

[XLVI]

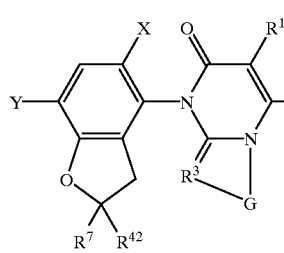

[XLVIII]

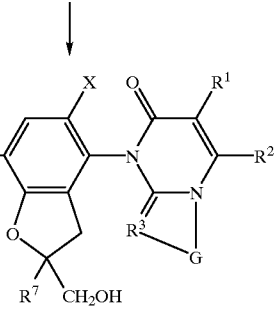

[XLVII]

wherein X, Y, G, $R^1$, $R^2$, $R^3$, and $R^7$ are as defined above and $R^{42}$ is as defined for $R^8$ but neither methyl nor hydroxymethyl.

The reaction conditions in the respective steps are, for example, as follows:

1) Procedure for preparing compound [XLIV] from compound [XLIII]

Compound [XLIV] can be prepared by heating compound [XLIII] in a solvent.

Solvent: N,N-dimethylaniline, N,N-diethylaniline, p-diisopropylbenzene

Temperature: 100° C. to 200° C.

Time: a moment to 24 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

2) Procedure for preparing compound [XLV] from compound [XLIV]

Compound [XLV] can be prepared by heating compound [XLIV] in the presence of an acid in a solvent.

Acid: organic acids such as p-toluenesulfonic acid, or inorganic acids such as sulfuric acid Amount of acid: a catalytic amount to 1 mole for 1 mole of compound [XLIV]

Solvent: toluene, xylene, or the like

Temperature: 100° C. to 250° C.

Time: a moment to 24 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

3) Procedure for compound [XLVI] from compound [XLIV]

Compound [XLVI] can be prepared by reacting compound [XLIV] with a peracid in a solvent.

Peracid: m-chloroperbenzoic acid, peracetic acid, or the like

Amount of peracid: 1 mole to an excessive amount for 1 mole of compound [XLIV]

Solvent: halogenated hydrocarbons such as dichloromethane, or organic acids such as acetic acid Temperature: −20° C. to room temperature Time: a moment to 24 hours After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

4) Procedure for preparing compound [XLVII] from compound [XLVI]

Compound [XLVII] can be prepared by heating compound [XLVI] in the presence of a base in a solvent Base: potassium carbonate or the like Amount of base: 1 to 2 moles for 1 mole of compound [XLVI]

Solvent: methanol, ethanol, or the like

Temperature: 0° C. to 50° C.

Time: a moment to 5 hours

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

5) Procedure for preparing compound [XLVIII] from compound [XLVII]

The reaction can be effected by the procedure for converting hydroxyalkyl at position 2 on the dihydrobenzofuran ring into another substituent group, as described on column 5–10 in the specification of U.S. Pat. No. 5,411,935.

Production Process 4

This is the production process according to the following scheme:

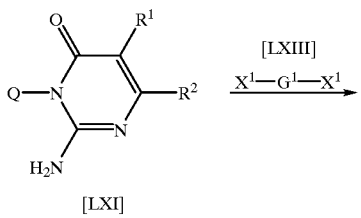

[LXI]

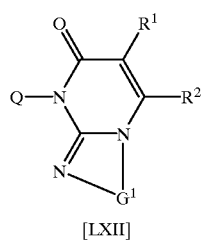

[LXII]

wherein Q, $R^1$, and $R^2$ are as defined above; $G^1$ is G-1 or G-2 as defined above; and $X^1$ is iodine, bromine, or chlorine.

1) Procedure for preparing compound [LXII] from compound [LXI]

Compound [LXII] can be prepared by reacting compound [LXI] with compound [LXIII] in the presence of a base in a solvent.

Amount of compound [LXIII]: 1 mole to an excessive amount for 1 mole of compound [LXI]

Solvent: ethers such as dioxane, alcohols such as ethanol, water, or the like

Temperature: 0° C. to heating temperature under reflux

Time: a moment to 48 hours

Base: alcoholates such as sodium ethoxide, organic bases such as triethylamine, or inorganic bases such as potassium carbonate Amount of base: 2 moles to an excessive amount for 1 mole of compound [LXI]

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

Production Process 5

This is the production process according to the following scheme:

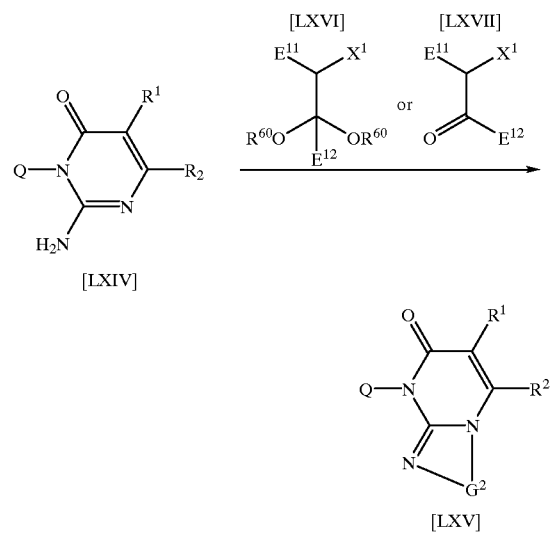

wherein Q, $X^1$, $R^1$, $R^2$, $E^{11}$, and $E^{12}$ are as defined above; $G^2$ is G-3 as defined above; and $R^{60}$ hydrogen or $C_1$–$C_5$ alkyl.

1) Procedure for preparing compound [LXV] from compound [LXIV]

Compound [LXV] can be prepared by reacting compound [LIV] with compound [LXVI] or compound [LXVII] in a solvent and if necessary, in the presence of an acid.

Amount of compound [LXVI] or compound [LXVII]: 1 mole to an excessive amount for 1 mole of compound [LXIV]

Solvent: ethers such as dioxane, alcohols such as ethanol, organic acids such as acetic acid, water, or the like Temperature: 0° C. to heating temperature under reflux Time: a moment to 168 hours Acid: inorganic acids such as hydrochloric acid Amount of acid: a catalytic amount to an excessive amount After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

The following are production processes for intermediates or starting compounds used in the production of the present compounds.

In the aniline derivatives of the general formula:

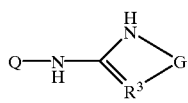

wherein Q, G, and $R^3$ are as defined above, which are the starting compounds in the production of the present compounds, the compounds of the general formula:

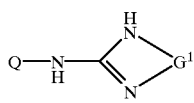

wherein Q and $G^1$ are as defined above, can be prepared, for example, by the following production process 6 or 7, and the compounds of the general formula:

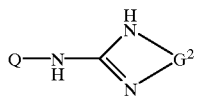

wherein Q and $G^2$ are as defined above, can be prepared, for example, by the following production process 8.

Production Process 6

This is the production process in which a carbamate derivative of the general formula:

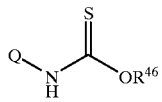

wherein Q is as defined above and $R^{46}$ is $C_1$–$C_6$ alkyl, is reacted with an amine derivative of the general formula:

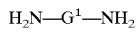

wherein $G^1$ is as defined above.

The reaction is usually effected without any solvent or in a solvent. The reaction temperature is usually in the range of 20° C. to 200° C. The reaction time is usually in the range of a moment to 24 hours.

The amounts of reagents to be used in the reaction are stoichiometrically 1 mole of the amine derivative of the above general formula for 1 mole of the carbamate compound of the above general formula, although they may suitably be changed with the reaction conditions.

The solvent which can be used may include aliphatic hydrocarbons such as hexane, heptane, ligroin, cyclohexane, and petroleum ether; aromatic hydrocarbons such as benzene, toluene, and xylene; halogenated hydrocarbons such as chlorobenzene and dichlorobenzene; ethers such as diethyl ether, diisopropyl ether, dioxane, THF, and ethylene glycol dimethyl ether; nitro compounds such as nitromethane and nitrobenzene; nitriles such as acetonitrile and isobutyronitrile; acid amides such as DMF; tertiary amines such as pyridine, triethylamine, diisopropylethylamine, N,N-dimethylaniline, N,N-diethylaniline, and N-methylmorpholine; sulfur compounds such as dimethylsulfoxide and sulforane; alcohols such as methanol, ethanol, ethylene glycol, and isopropanol; water; and mixtures thereof. The amine derivatives of the above general formula can also be used as the solvents.

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

The carbamate derivatives of the above general formula can be prepared by the known methods, for example, by reacting an isothiocyanate of Q-NCS (wherein Q is as defined above) with $R^{46}$OH (wherein $R^{46}$ is as defined above).

The isothiocyanate of Q-NCS (wherein Q is as defined above) is commercially available or can be prepared, for example, by the procedures as described in the "Jikken Kagaku Kohza" (Maruzen Kabushiki Kaisha), 4th ed., vol 20, pp. 483–489.

Production Process 7

This is the production process in which an isothiocyanate derivative of Q-NCS (wherein Q is as defined above) is reacted with an amine derivative of the above general formula.

The reaction is usually effected without any solvent or in a solvent. The reaction temperature is usually in the range of 20° C. to 200° C. The reaction time is usually in the range of a moment to 24 hours.

The amounts of reagents to be used in the reaction are stoichiometrically 1 mole of the amine derivative of the above general formula for 1 mole of the isothiocyanate derivative of Q-NCS, although they may suitably be changed with the reaction conditions.

The solvent which can be used may include aliphatic hydrocarbons such as hexane, heptane, ligroin, cyclohexane, and petroleum ether; aromatic hydrocarbons such as benzene, toluene, and xylene; halogenated hydrocarbons such as chlorobenzene and dichlorobenzene; ethers such as diethyl ether, diisopropyl ether, dioxane, THF, and ethylene glycol dimethyl ether; nitro compounds such as nitromethane and nitrobenzene; nitriles such as acetonitrile and isobutyronitrile; acid amides such as DMF; tertiary amines such as pyridine, triethylamine, diisopropylethylamine, N,N-dimethylaniline, N,N-diethylaniline, and N-methylmorpholine; sulfur compounds such as dimethylsulfoxide and sulforane; water; and mixtures thereof. The amine derivatives of the above general formula can also be used as the solvents.

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

Production Process 8

This is the production process according to the following scheme:

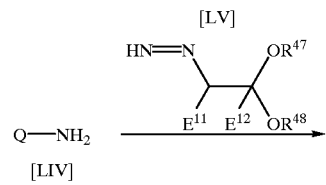

-continued

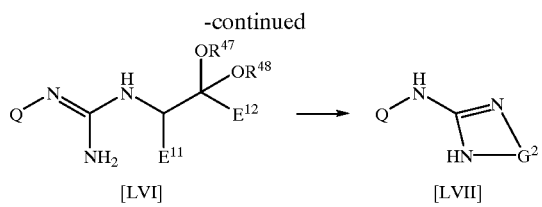

wherein $R^{47}$ and $R^{48}$ are independently $C_1$–$C_6$ alkyl; and Q, $E^{11}$, $E^{12}$, and $G^2$ are as defined above (see J. Med. Chem., 1997, 40, 18–23).

1) Procedure for preparing compound [LVI] from compound [LIV]

Compound [LVI] can be prepared by reacting compound [LIV] with compound [LV] in the presence of an acid in a solvent.

Amount of compound [LV]: 1 mole to an excessive amount for 1 mole of compound [LIV]

Solvent: ethanol or the like
Temperature: 0° C. to heating temperature under reflux
Time: a moment to 24 hours
Acid: organic acids such as methanesulfonic acid
Amount of acid: a catalytic amount to an excessive amount After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

2) Procedure for preparing compound [LVII] from compound [LVI]

Compound [LVII] can be prepared by reacting compound [LVI] in the presence of an acid in a solvent.

Solvent: water or the like
Temperature: 0° C. to heating temperature under reflux
Time: a moment to 24 hours
Acid: inorganic acids such as hydrochloric acid
Amount of acid: a catalytic amount to an excessive amount After completion of the reaction, the crystals precipitated by the addition of water are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

The aniline derivatives of Q-$NH_2$ (wherein Q is as defined above) are known in the art, for example, in the published specification of European Patent Application, EP-61741-A; the specifications of U.S. Pat. No. 5,169,431; and Japanese Laid-open Patent Publication No. 63-156787, or can be prepared by the procedures as described therein.

Production Process 9

The 2-aminopyrimidine derivatives used in the production processes 4 and 5 can be prepared by the following scheme:

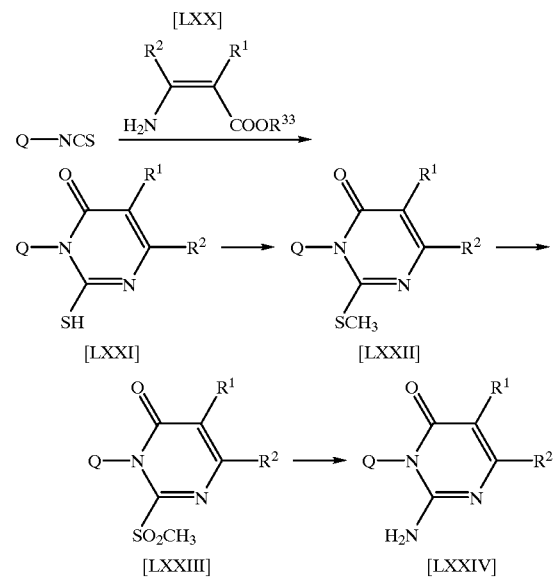

wherein Q, $R^1$, $R^2$, and $R^{33}$ are as defined above (see the published specification of European Patent Application EP-0396250).

1) Procedure for preparing compound [LXXI] from isothiocyanate derivative

Compound [LXXI] can be prepared by reacting compound [LXX] with an isothiocyanate derivative in the presence of a base in a solvent.

Amount of compound [LXX]: 1 mole to an excessive amount for 1 mole of isothiocyanate derivative Solvent: N,N-dimethylformamide or the like
Temperature: 0° C. to 100° C.
Time: a moment to 24 hours
Base: inorganic bases such as sodium hydride
Amount of base: 1 mole to an excessive amount for 1 mole of isothiocyanate derivative After completion of the reaction, the crystals precipitated, if necessary, by the addition of aqueous hydrochloric acid, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

2) Procedure for preparing compound [LXXII] from compound [LXXI]

Compound [LXXII] can be prepared by methylating compound [LXXI] in the presence of a base in a solvent.

Amount of methylating agent: 1 mole to an excessive amount for 1 mole of compound [LXXI]

Methylating agent: iodomethane, dimethyl sulfate, or the like
Solvent: N,N-dimethylformamide or the like
Temperature: −10° C. to 100° C.
Time: a moment to 24 hours
Base: organic bases such as triethylamine, or inorganic bases such as potassium carbonate
Amount of base: 1 mole to an excessive amount for 1 mole of compound [LXXI]

After completion of the reaction, the crystals precipitated by the addition of water are collected by filtration, or the reaction mixture is subjected to ordinary post-treatments such as extraction with an organic solvent and concentration.

If necessary, purification may be carried out by an ordinary technique such as chromatography or recrystallization. Thus the desired compound can be isolated.

3) Procedure for preparing compound [LXXIII] from compound [LXXII]

Compound [LXXIII] can be prepared by oxidizing compound [LXXII] in a solvent.

Amount of oxidizing agent: 2 moles to an excessive amount for 1 mole of compound [LXXII]
Oxidizing agent: m-chloroperbenzoic acid or the like
Solvent: chloroform or the like
Temperature: −10° C. to refluxing temperature
Time: a moment to 48 hours After completion of the reaction, the reaction mixture is washed with an aqueous solution of sodium hydrogensulfite or the like and then subjected to ordinary post-treatments such as extraction with an organic solvent and concentration. If necessary, purification may be carried out by an ordinary technique such as chromatography or recrystallization. Thus the desired compound can be isolated.

4) Procedure for preparing compound [LXXIV] from compound [LXXIII]

Compound [LXXIV] can be prepared by reacting compound [LXXIII] with ammonia in a solvent.

Amount of ammonia: 1 mole to an excessive amount for 1 mole of compound [LXXIII]
Solvent: 2-propanol, 2-methyl-2-propanol, or the like
Temperature: −10° C. to refluxing temperature
Time: a moment to 48 hours After completion of the reaction, the reaction mixture is poured into water and the precipitated crystals are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

Production Process 10

Compound [XXXVII] used in the Production Process 2 may be produced by hydrolyzing the compound of the formula:

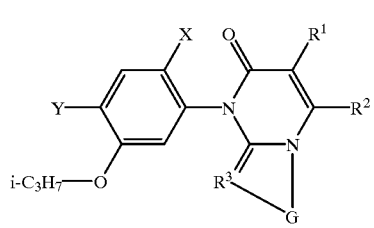

[XXXVI]

wherein $R^1$, $R^2$, $R^3$, G, X and Y are as defined above in the presence of an acid such as sulfuric acid, or by treating said compound with an acid such as boron tribromide in a solvent such as methylene chloride and then with water.

The reaction temperature is usually in the range of −20° C. to 150° C., preferably 0° C. to 100° C. The reaction time is usually in the range of a moment to 72 hours.

The amount of acid to be used in the reaction is stoichiometrically 1 mole for 1 mole of compound [XXXVI], although it may suitably be changed with the reaction conditions.

After completion of the reaction, the crystals precipitated, if necessary, by the addition of water, are collected by filtration, or the reaction mixture is subjected to ordinary post-treatments such as extraction with an organic solvent and concentration. If necessary, purification may be carried out by an ordinary technique such as chromatography or recrystallization. Thus the desired compound can be isolated.

Compound [XXXVI] may be produced by using the same manner as described in Production Process 4 or 5, except that the compound of the formula:

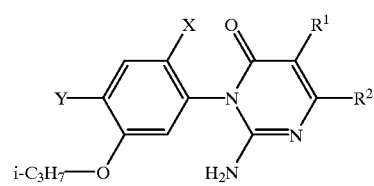

[LXI-1]

wherein $R^1$, $R^2$, X and Y are as defined above is substituted for the compound [LXI] or the compound [LXIV].

Compound [LXI-1] may be produced by using the same manner as described in Production Process 9, except that the compound of the formula:

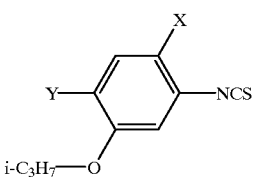

wherein X and Y are as defined above is substituted for the compound Q-NCS.

Production Process 11

Compound [XLIII] used in the Production Process 3 may be produced by using the same manner as described in Production Process 2, 1), except that the compound of the formula:

$CH_2=C(R^7)CH_2Cl$ wherein $R^7$ is as defined above is substituted for 2,3-dichloropropene.

Production Process 12

Compound of the formula:

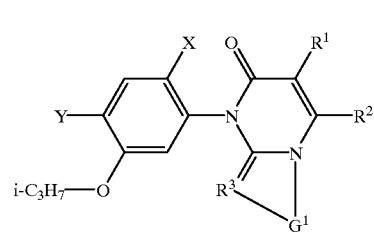

[XXXVII-1]

where in $R^1$, $R^2$, $R^3$, $G^1$, X and Y are as defined above may be produced by using the same manner as described in Production Process 1, except that the compound of the formula:

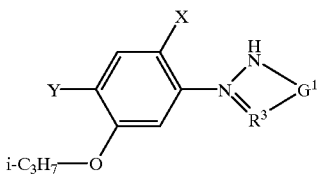

[XXXVII-2]

wherein R³, G¹, X and Y are as defined above is substituted for the compound of the formula:

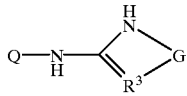

wherein R³, G and Q are as defined above.

Compound [XXXVII-2] may be produced by using the same manner as described in Production Process 6 or 7, except that the compound of the formula:

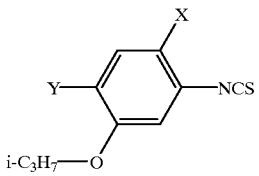

wherein X and Y are as defined above is substituted for the compound Q-NCS or the compound of the formula:

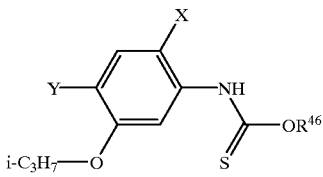

wherein X, Y and R⁴⁶ are as defined above is substituted for the compound of the formula:

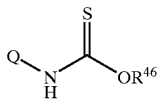

wherein Q and R⁴⁶ are as defined above.

The presence compounds have excellent herbicidal activity and some of them exhibit excellent selectivity between crops and weeds. More particularly, the present compounds have herbicidal activity against various weeds which may cause some trouble in the foliar treatment and soil treatment on upland fields, such as listed below.

Polygonaceous weeds:
wild buckwheat (*Polygonum convolvulus*), pale smartweed (*Polygonum lapathifolium*), pennsylvania smartweed (*Polygonum pensylvanicum*), ladysthumb (*Polygonum persicaria*), curly dock (*Rumex crispus*), broadleaf dock (*Rumex obtusifolius*), Japanese knotweed (*Polygonum cuspidatum*)

Portulacaceous weeds:
common purslane (*Portulaca oleracea*)

Caryophyllaceous weeds:
common chickweed (*Stellaria media*)

Chenopodiaceous weeds:
common lambsquarters (*Chenopodium album*), kochia (*Kochia scoparia*)

Amaranthaceous weeds:
redroot pigweed (*Amaranthus retroflexus*), smooth pigweed (*Amaranthus hybridus*)

Cruciferous (brassicaceous) weeds:
wild radish (*Raphanus raphanistrum*), wild mustard (*Sinapis arvensis*), shepherdpurse (*Capsella bursa-pastoris*)

Leguminous (fabaceous) weeds:
hemp sesbania (*Sesbania exaltata*), sicklepod (*Cassia obtusifolia*), Florida beggarweed (*Desmodium tortuosum*), white clover (*Trifolium repens*)

Malvaceous weeds:
velvetleaf (*Abutilon theophrasti*), prickly sida (*Sida spinosa*)

Violaceous weeds:
field pansy (*Viola arvensis*), wild pansy (*Viola tricolor*)

Rubiaceous weeds:
catchweed bedstraw (cleavers) (*Galium aparine*)

Convolvulaceous weeds:
ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa*), field bindweed (*Convolvulus arvensis*)

Labiate weeds:
red deadnettle (*Lamium purpureum*), henbit (*Lamium amplexicaule*)

Solanaceous weeds:
jimsonweed (*Datura stramonium*), black nightshade (*Solanum nigrum*)

Scrophulariaceous weeds:
birdseye speedwell (*Veronica persica*), ivyleaf speedwell (*Veronica hederaefolia*)

Composite weeds:
common cocklebur (*Xanthium pensylvanicum*), common sunflower (*Helianthus annuus*), scentless chamomile (*Matricaria perforata* or *inodora*), corn marigold (*Chrysanthemum segetum*), pineappleweed (*Matricaria matricaroides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*)

Boraginaceous weeds:
forget-me-not (*Myosotis arvensis*)

Asclepiadaceous weeds:
common milkweed (*Asclepias syriaca*)

Euphorbiaceous weeds:
sun spurge (*Euphorbia helioscopia*), spotted spurge (*Euphorbia maculata*)

Graminaceous weeds:
barnyardgrass (*Echinochloa crus-galli*), green foxtail (*Setari viridis*), giant foxtail (*Setaria faberi*), large crabgrass (*Digitari sanguinalis*), goosegrass (*Eleusine indica*), annual bluegrass (*Poa annua*), blackgrass (*Alopecurus myosuroides*), wild oats (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texanum*), shattercane (*Sorghum vulgare*)

Commelinaceous weeds:
common dayflower (*Commelina communis*)
Equisetaceous weeds:
field horsetail (*Equisetum arvense*)
Cyperaceous weeds:
rice flatsedge (*Cyperus iria*), purple nutsedge (*Cyperus rotundus*), yellow nutsedge (*Cyperus esculentus*)

Furthermore, some of the present compounds exhibit no significant phytotoxicity on the main crops such as corn (*Zea mays*), wheat (*Triticum aestivum*), barley (*Hordeum vulgare*), rice (*Oryza sativa*), sorghum (*Sorghum bicolor*), soybean (*Glycine max*), cotton (Gossypium spp.), sugar beet (*Beta vulgaris*), peanut (*Arachis hypogaea*), sunflower (*Helianthus annuus*), and canola (*Brassica napus*); horticultural crops such as flowers and ornamental plants; and vegetable crops.

The present compounds can also attain the effective control of various weeds which may cause some trouble in the no-tillage cultivation of soybean (*Glycine max*), corn (*Zea mays*), wheat (*Triticum aestivum*), and other crops. Furthermore, some of them exhibit no significant phytotoxicity on the crops.

The present compounds also have herbicidal activity against various weeds which may cause some trouble in the flooding treatment on paddy fields, such as listed below.
Graminaceous weeds:
  barnyardgrass (*Echinochloa oryzicola*)
Scrophulariaceous weeds:
common falsepimpernel (*Lindernia procumbens*)
Lythraceous weeds:
Indian toothcup (*Rotala indica*), red stem (*Ammannia multiflora*)
Elatinaceous weeds:
waterwort (*Elatine triandra*)
Cyperaceous weeds:
smallflower umbrella sedge (*Cyperus difformis*), hardstem bulrush (*Scirpus juncoides*), needle spikerush (*Eleocharis acicularis*), water nutgrass (*Cyperus serotinus*), water chestnut (*Eleocharis kuroguwal*)
Pontederiaceous weeds:
monochoria (*Monochoria vaginalis*)
Alismataceous weeds:
arrowhead (*Sagittaria pygmaea*), arrowhead (*Sagittaria trifolia*), waterplantain (*Alisma canaliculatum*)
Potamogetonaceous weeds:
roundleaf pondweed (*Potamogeton distinctus*)
Umbelloferous weeds:
watercelery sp. (*Oenanthe javanica*)

Furthermore, some of the present compounds exhibit no significant phytotoxicity on transplanted paddy rice.

The present compounds can also attain the control of a wide variety of weeds which grow or will grow in the orchards, grasslands, lawns, forests, waterways, canals, or other non-cultivated lands.

The present compounds also have herbicidal activity against various aquatic weeds, such as water hyacinth (*Eichhornia crassipes*), which grow or will grow at the waterside such as waterways or canals.

The present compounds have substantially the same characteristics as those of the herbicidal compounds disclosed in the published specification of International Patent Application, WO95/34659. In the case where crops with tolerance imparted by introducing a herbicide tolerance gene described in the published specification are cultivated, the present compounds can be used at larger rates than those used when ordinary crops without tolerance are cultivated, which makes it possible to control other unfavorable weeds more effectively.

When the present compounds are used as the active ingredients of herbicides, they are usually mixed with solid or liquid carriers or diluents, surfactants, and other auxiliary agents to give emulsifiable concentrates, wettable powders, flowables, granules, concentrated emulsions, water-dispersible granules, or other formulations.

These formulations may contain any of the present compounds as an active ingredient at an amount of 0.001 to 80% by weight, preferably 0.005 to 70% by weight, based on the total weight of the formulation.

The solid carrier or diluent which can be used may include, for example, fine powders or granules of the following materials: mineral matters such as kaolin clay, attapulgite clay, bentonite, acid clay, pyrophyllite, talc, diatomaceous earth, and calcite; organic substances such as walnut shell powder; water-soluble organic substances such as urea; inorganic salts such as ammonium sulfate; and synthetic hydrated silicon oxide. The liquid carrier or diluent which can be used may include, for example, aromatic hydrocarbons such as methylnaphthalene, phenylxylylethane, and alkylbenzene (e.g., xylene); alcohols such as isopropanoli ethylene glycol, and 2-ethoxyethanol; esters such as phthalic acid dialkyl esters; ketones such as acetone, cyclohexanone, and isophorone; mineral oils such as machine oil; vegetable oils such as soybean oil and cottonseed oil; dimethylsulfoxide, N,N-dimethylformamide, acetonitrile, N-methylpyrrolidone, and water.

The surfactant used for emulsification, dispersing, or spreading may include surfactants of the anionic type, such as alkylsulfates, alkylsulfonates, alkylarylsulfonates, dialkylsulfosuccinates, and phosphates of polyoxyethylene alkyl aryl ethers; and surfactants of the nonionic type, such as polyoxyethylene alkyl ethers, polyoxyethylene alkyl alkyl ethers, polyoxyethylene polyoxypropylene block copolymers, sorbitan fatty acid esters, and polyoxyethylene sorbitan fatty acid esters.

The auxiliary agent may include lignin sulfonates, alginates, polyvinyl alcohol, gum arabic, CMC (carboxymethylcellulose), and PAP (isopropyl acid phosphate).

The present compounds are usually formulated as described above and then used for pre- or post-emergence soil, foliar, or flooding treatment of weeds. The soil treatment may include soil surface treatment and soil incorporation. The foliar treatment may include application over the plants and directed application in which a chemical is applied only to weeds so as to keep off the crop plants.

The present compounds may often exhibit the enhancement of herbicidal activity when used in admixture with other herbicides. They can also be used in admixture with insecticides, acaricides, nematocides, fungicides, bactericides, plant growth regulators, fertilizers, and soil conditioners.

Examples of the herbicide which can be used in admixture with the present compounds are atrazine, cyanazine, dimethametryn, metribuzin, prometryn, simazine, simetryn, chlorotoluron, diuron, dymron, fluometuron, isoproturon, linuron, methabenzthiazuron, bromoxynil, ioxynil, ethalfluralin, pendimethalin, trifluralin, acifluorfen, acifluorfen-sodium, bifenox, chlomethoxynil, fomesafen, lactofen, oxadiazon, oxadiargyl, oxyfluorfen, carfentrazone, flumiclorac-pentyl, flumioxazine, fluthiacet-methyl, sulfentrazone, thidiazimin, difenzoquat, diquat, paraquat, 2,4-D, 2,4-DB, DCPA, MCPA, MCPB, clomeprop, clopyralid, dicamba, dithiopyr, fluroxypyr, mecoprop, naproanilide, phenothiol, quinclorac, triclopyr, acetochlor, alachlor, butachlor, diethatyl-ethyl, metolachlor, pretilachlor, propachlor, bensulfuron-methyl, chlorsulfuron, chlorimuron-ethyl, halosulfuron-methyl, metsulfuron-methyl, nicosulfuron, primisulfuron, pyrazosulfuron-ethyl, sulfometuron-ethyl, thifensulfuron-methyl, triasulfuron, tribenuron-methyl, azimsulfuron, cloransulam-methyl, cyclosulfamuron, flumetsulam, flupyrsulfron, flazasulfuron, imazosulfuron, metosulam, prosulfuron, rimsulfuron, triflusulfuron-methyl, imazamethabenz-methyl, imazapyr, imazaquin, imazethapyr, imazameth, imazamox, bispyribac-sodium, pyriminobac-methyl, pyrithiobac-sodium, alloxydim-sodium, clethodim, sethoxydim, tralkoxydim, dichlofop-methyl, fenoxaprop-ethyl, fenoxaprop-p-ethyl, fluazifop-butyl, fluazifop-p-butyl, haloxyfop-methyl, quizalofop-p-ethyl, cyhalofop-butyl, clodinafop-propargyl, benzofenap, clomazone, diflufenican, norflurazon, pyrazolate, pyrazoxyfen, isoxaflutole, sulcotrione, glufosinate-ammonium, glyphosate, bentazon, benthiocarb, bromobutide, butamifos, butylate, dimepiperate, dimethenamid, DSMA, EPTC, esprocarb, isoxaben, mefenacet, molinate, MSMA, piperophos, pyributicarb, propanil, pyridate, triallate, cafenstrol, flupoxam, and fluthiamide.

These compounds are described in the catalog of Farm Chemicals Handbook, 1995 (published by Meister Publishing Company); AG CHEM NEW COMPOUND REVIEW, VOL. 13, 1995 (published by AG CHEM INFORMATION SERVICES); and "Josouzai Kenkyu Souran" (published by Hakuyu-sha).

When the present compounds are used as the active ingredients of herbicides, the application amount, although it may vary with the weather conditions, formulation types, application times, application methods, soil conditions, crops to be protected, weeds to be controlled, and other factors, is usually in the range of 0.01 to 10,000 g, preferably 1 to 8000 g, per hectare. In the case of emulsifiable concentrates, wettable powders, flowables, concentrated emulsions, water-dispersible granules, or other similar formulations, they are usually applied after diluted in their prescribed amounts with water (if necessary, containing an adjuvant such as a spreading agent) at a ratio of 10 to 1000 liters per hectare. In the case of granules or some types of flowables, they are usually applied as such without any dilution.

The adjuvant which can be used herein, if necessary, may include, in addition to the surfactants as described above, polyoxyethylene resin acids (esters), lignin sulfonates, abietates, dinaphthylmethanedisulfonates, crop oil concentrates, and vegetable oils such as soybean oil, corn oil, cottonseed oil, and sunflower oil.

The present compounds can also be used as the active ingredients of harvesting aids such as defoliants and desiccants for cotton (Gossipyum spp.), and desiccants for potato (*Solanum tuberosum*). In these cases, the present compounds are usually formulated in the same manner as the case where they are used as the active ingredients of herbicides, and used alone or in admixture with other harvesting aids for foliar treatment before the harvesting of crops.

EXAMPLES

The present invention will be further illustrated by the following production examples, formulation examples, and test examples; however, the present invention is not limited to these examples.

Production Example 1

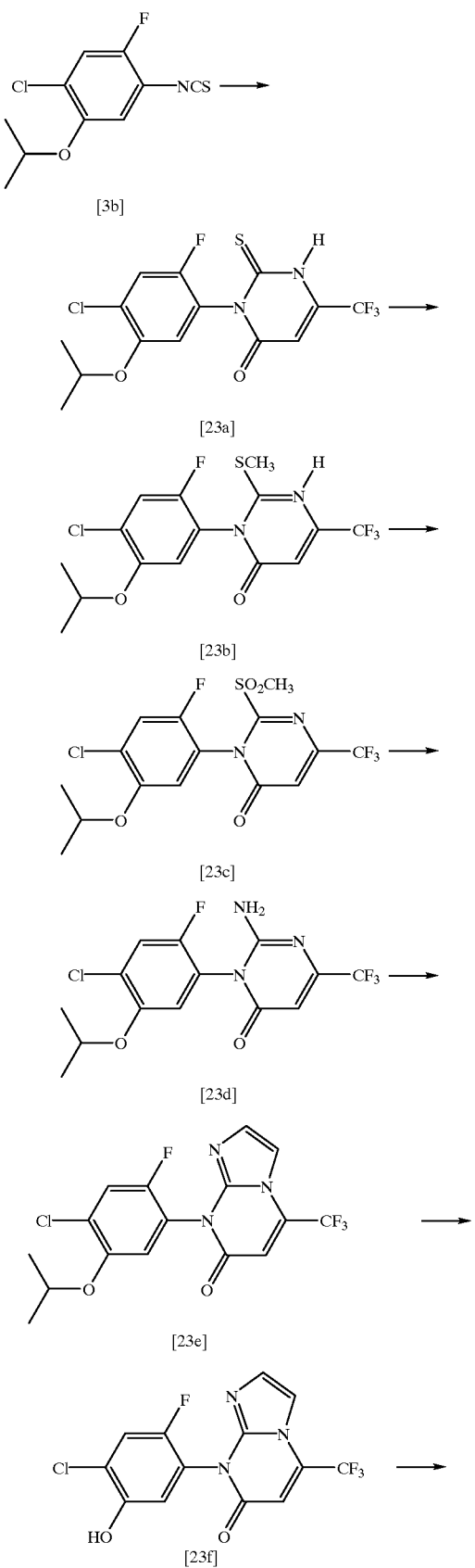

-continued

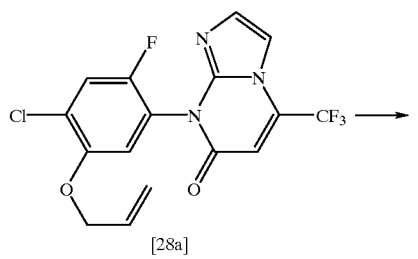

[28a]

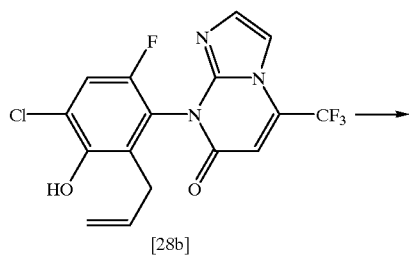

[28b]

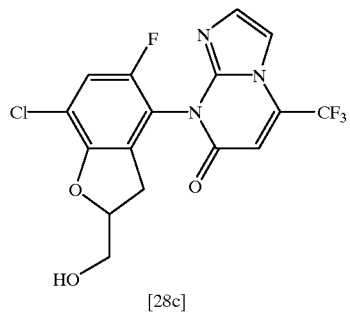

[28c]

First, 25.0 g of ethyl 3-amino-4,4,4-trifluorocrotonate was added to a suspension of 5.4 g of sodium hydride in 100 ml of N,N-dimethylformamide, while keeping the reaction mixture below 10° C. The reaction mixture was then stirred at room temperature for 30 minutes, to which a solution of 30.0 g of compound [3b] in 150 ml of toluene was added dropwise, while keeping the reaction mixture below 40° C. After completion of the addition, the reaction mixture was stirred at room temperature for 2 hours and then poured into water, which was neutralized with diluted hydrochloric acid and then extracted with diethyl ether. The organic layer was dried over magnesium sulfate and then concentrated. The crystals thus obtained were washed with a mixed solvent of hexane and diethyl ether (1:1) to give 16.0 g of compound [23a] (m.p., 224.9° C.).

Then, 5.0 g of triethylamine was added to a solution of 16.0 g of compound [23a] in 100 ml of N,N-dimethylformamide, followed by stirring for 30 minutes and addition of 6.0 g of iodomethane. The reaction mixture was stirred for another 1 hour and then poured into water, which was neutralized with diluted hydrochloric acid and then extracted with diethyl ether. The organic layer was dried over magnesium sulfate and then concentrated to give 16.4 g of compound [23b] (m.p., 88.4° C.).

Then, 28.6 g of m-chloroperbenzoic acid was added to a solution of 16.0 g of compound [23b] in 150 ml of chloroform. The reaction mixture was stirred for 12 hours and then filtered. The filtrate was washed with aqueous sodium thiosulfate solution and then with aqueous potassium carbonate solution, dried over magnesium sulfate, and then concentrated to give 16.5 g of compound [23c] (m.p., 164.8° C.).

Then, 16.2 g of compound [23c] was suspended in 150 ml of 2-methyl-2-propanol, into which ammonia gas was blown for 30 minutes, and the reaction mixture was poured into water. The precipitated crystals were collected by filtration, washed with water, and then dried to give 11.2 g of compound [23d] (m.p., 260.4° C.).

Then, 13.0 g of 2-bromo-1,1-dimethoxyethane was added to a mixed solution of 5.0 g of concentrated hydrochloric acid and 26.0 g of acetic acid, followed by stirring at room temperature for 15 minutes and addition of 11.0 g of compound [23d]. The reaction mixture was heated under reflux for 10 hours and then poured into water, which was extracted with diethyl ether. The organic layer was washed with saturated aqueous sodium hydrogencarbonate solution, dried over magnesium sulfate, and then concentrated. The residue was subjected to silica gel chromatography (eluent, hexane:ethyl acetate=5:1), which afforded 6.7 g of compound [23e] (m.p., 132.1° C.).

Then, 6.0 g of compound [23e] was added to 50 ml of concentrated sulfuric acid. The reaction mixture was stirred for 3 hours and then poured into ice water, which was stirred for another 1 hour and then extracted with diethyl ether. The organic layer was dried over magnesium sulfate and then concentrated. The residue was subjected to silica gel chromatography (eluent, hexane: ethyl acetate=3:1), which afforded 2.4 g of compound [23f].

$^1$H-NMR (250 MHz, CDCl$_3$, TMS)δ (ppm): 6.73 (1H, s), 6.74 (1H, d, J=6.5 Hz), 7.19 (1H, d, J=1.9 Hz), 7.29 (1H, d, J=1.9 Hz), 7.32 (1H, d, J=9.0 Hz).

Then 2.3 ml of N,N-dimethylformamide, 239 mg of potassium carbonate, and 154 mg of alkyl bromide were added to 400 mg of compound [23f], followed by stirring at room temperature for 1.5 hours. Then, water was added to the reaction mixture, which was extracted with ethyl acetate. The organic layer was washed with saturated aqueous sodium chloride solution, dried over anhydrous magnesium sulfate, and then concentrated. The residue was subjected to silica gel column chromatography (eluent, hexane:ethyl acetate=3:1), which afforded 366 mg of compound [28a] (m.p., 103.3° C.).

Then, 250 mg of compound [28a] was dissolved in 3.2 ml of N,N-diethylaniline, which was heated under reflux for 2.5 hours. After completion of the reaction, the reaction mixture was cooled to room temperature. Then, water was added to the reaction mixture, which was extracted with ethyl acetate. The organic layer was washed with saturated aqueous sodium chloride solution, dried over anhydrous magnesium sulfate, and then concentrated. The residue was subjected to silica gel column chromatography (eluent, hexane:ethyl acetate=2:1) to give 202 mg of compound [28b].

$^1$H-NMR (250 MHz, CDCl$_3$, TMS) δ (ppm): 3.19 (1H, ddt, J=15.4, 6.8, 1.3 Hz), 3.44 (1H, ddt, J=15.4, 6.2, 1.3 Hz), 4.77 (1H, ddd, J=17.0, 3.1, 1.3 Hz), 4.84 (1H, ddd, J=10.1, 3.1, 1.3 Hz), 5.69 (1H, dddd, J=17.0, 10.1, 6.8, 6.2 Hz), 6.68 (1H, s), 7.2–7.3 (2H, m)

Finally, 412 mg of compound [28b] was dissolved in 6 ml of chloroform, to which 341 mg of m-chloroperbenzoic acid was added, followed by stirring at room temperature for 3 hours. The reaction was quenched with saturated aqueous sodium thiosulfate solution. The organic layer was washed with 5% aqueous potassium carbonate solution, dried, and then concentrated. The residue was subjected to silica gel column chromatography (eluent, hexane:ethyl acetate=2:1), which afforded 162 mg of compound [28c] (present compound 9–14) (m.p., 213.6° C.; decomposition).

$^1$H-NMR (300 MHz, CDCl$_3$, TMS) δ (ppm): 2.2–2.5 (1H, b), 3.0–3.3 (2H, m), 3.74 (1H, dd, J=12.3, 4.9 Hz), 3.90 (1H, dd, J=12.3, 2.9 Hz), 5.0–5.2 (1H, m), 6.68 (1H, s), 7.2–7.3 (2H, m)

Production Example 2

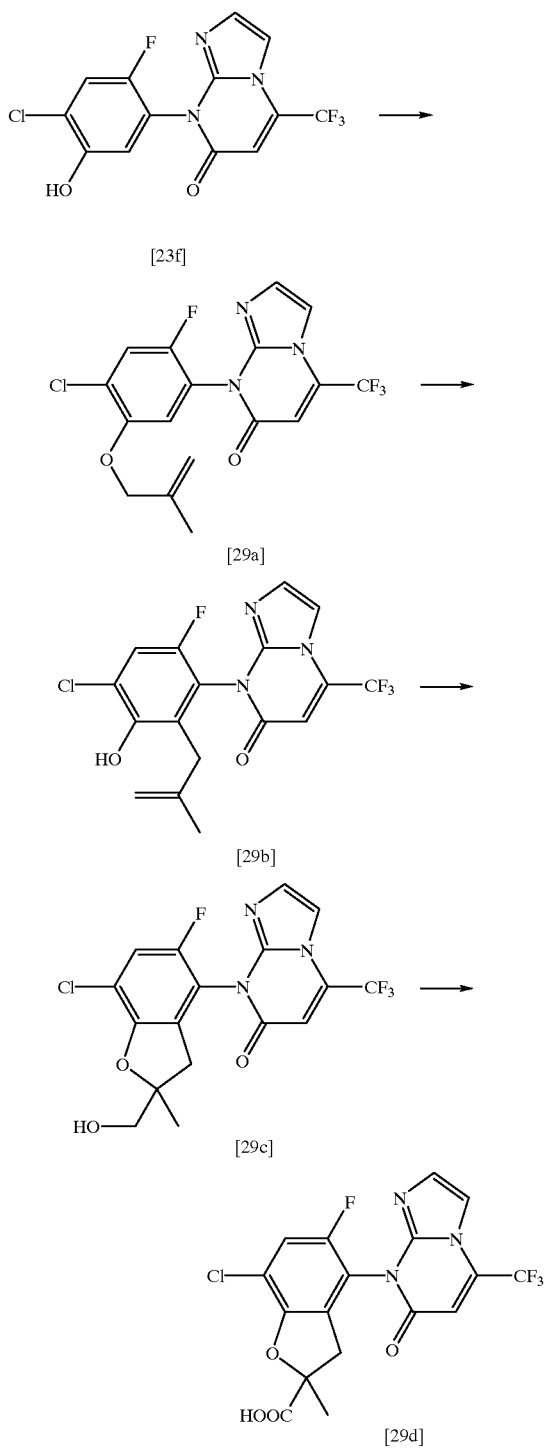

First, 4.0 ml of N,N-dimethylformamide, 419 mg of potassium carbonate, and 201 mg of methallyl chloride were added to 700 mg of compound [23f], followed by stirring at 60° C. for 4 hours. Then, water was added to the reaction mixture, which was extracted with ethyl acetate. The organic layer was washed with saturated aqueous sodium chloride solution, dried over anhydrous magnesium sulfate, and then concentrated. The residue was subjected to silica gel column chromatography (eluent, hexane: ethyl acetate=3:1), which afforded 490 mg of compound [29a].

$^1$H-NMR (300 MHz, CDCl$_3$, TMS)δ (ppm): 1.84 (3H, s), 4.45 (2H, s), 5.01 (1H, s), 5.13 (1H, s), 6.69 (1H, s), 6.95 (1H, d, J=6.2 Hz), 7.15 (1H, d, J=1.8 Hz), 7.26 (1H, d, J=1.8 Hz), 7.39 (1H, d, J=9.0 Hz)

Then, 490 mg of compound [29a] was dissolved in 5.5 ml of N,N-diethylaniline, which was heated under reflux for 4 hours. After completion of the reaction, the reaction mixture was cooled to room temperature. Then, water was added to the reaction mixture, which was extracted with ethyl acetate. The organic layer was washed with saturated aqueous sodium chloride solution, dried over anhydrous magnesium sulfate, and then concentrated. The residue was subjected to silica gel column chromatography (eluent, hexane:ethyl acetate=3:1), which afforded 377 mg of compound [29b] (m.p., 207° C.; decomposition).

Then, 1.79 g of compound [29b] was dissolved in 22.5 ml of chloroform, to which 1.43 g of m-chloroperbenzoic acid was added, followed by stirring at room temperature for 2 hours. The reaction was quenched with saturated aqueous sodium thiosulfate solution. The organic layer was washed with 5% aqueous potassium carbonate solution, dried, and then concentrated. The residue was subjected to silica gel column chromatography, which afforded 1.14 g of compound [29c] (present compound 9-206) as a mixture of two stereoisomers.

isomer-1: $^1$H-NMR (300 MHz, CDCl$_3$, TMS)δ (ppm): 1.49 (3H, s), 2.86 (1H, d, J=16 Hz), 3.23 (1H, d, J=16 Hz), 3.5–3.8 (1H, m), 6.66 (1H, s), 7.12 (1H, d, J=9.5 Hz), 7.17 (1H, d, J=1.8 Hz), 7.26 (1H, d, J=1.8 Hz)

isomer-2: $^1$H-NMR (300 MHz, CDCl$_3$, TMS)δ ppm): 1.48 (3H, s), 2.85 (1H, d, J=16 Hz), 3.25 (1H, d, J=16 Hz), 3.57 (1H, d, J=12 Hz), 3.71 (1H, d, J=12 Hz), 6.68 (1H, s), 7.12 (1H, d, J=9.5 Hz), 7.16 (1H, d, J=1.8 Hz), 7.26 (1H, d, J=1.8 Hz)

Then, 270 mg of compound [29c] (present compound 9–206) was dissolved in 5.4 ml of acetone, to which 0.49 ml of Jones reagent was slowly added under ice cooling, followed by stirring for 2 hours and then at room temperature for 1 hour. The reaction was quenched with isopropyl alcohol. The reaction mixture was poured into water, which was extracted with ethyl acetate. The organic layer was dried over anhydrous magnesium sulfate and then concentrated, which afforded 271 mg of compound [29d] present compound 9-292).

Production Example 3

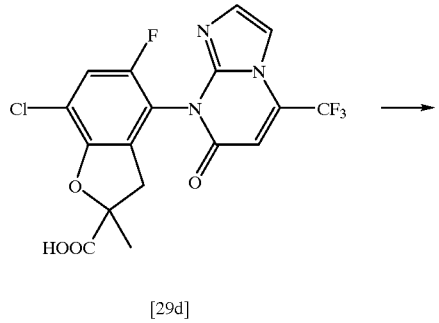

[29d]

-continued

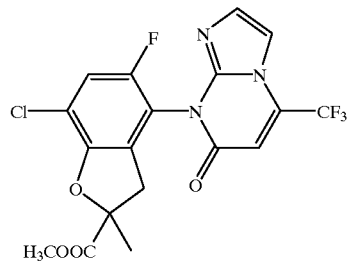

[30a]

First, 96 mg of compound [29d] (present compound 9-292) was dissolved in methanol, to which 8 mg of p-toluenesulfonic acid was added. The reaction mixture was heated under reflux for 2 hours, concentrated, and then diluted with ethyl acetate, which was washed with saturated aqueous sodium chloride solution, dried over anhydrous magnesium sulfate, and then concentrated. The residue was subjected to silica gel column chromatography (eluent, hexane:ethyl acetate=3:1), which afforded 28 mg of compound [30a] (present compound 9-298).

$^1$H-NMR (300 MHz, CDCl$_3$, TMS) δ (ppm): 1.75 (3H, s), 3.10 (1H, d, J=17 Hz), 3.61 (1H, d, J=17 Hz), 3.79 (3H, s), 6.66 (1H, s), 7.1–7.3 (3H, m)

Production Example 4

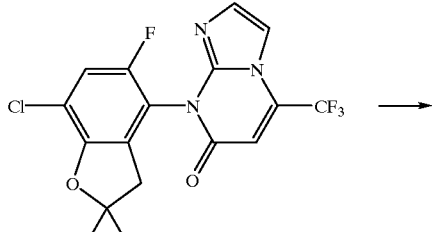

[29d]

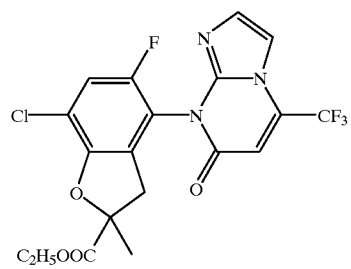

[31a]

In the same manner as described in Production Example 3, except that ethanol was substituted for methanol, 22 mg of compound [31a] (present compound 9-304) was obtained from 89 mg of compound [29d].

$^1$H-NMR (300 MHz, CDCl$_3$, TMS) δ (ppm): 1.2–1.3 (3H, m), 1.75 (3H, s), 3.10 (1H, d, J=17 Hz), 3.60 (1H, d, J=17 Hz), 4.2–4.3 (2H, m), 6.68 (1H, s), 7.1–7.3 (3H, m)

Production Example 5

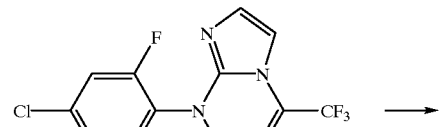

[23f]

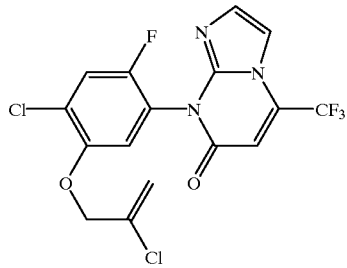

[32a]

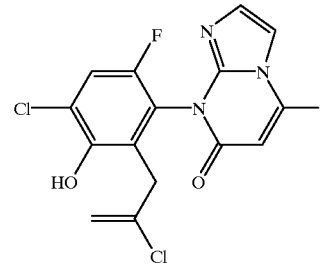

[32b]

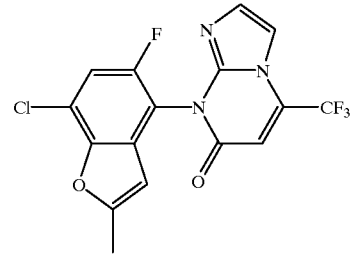

[32c]

First, 4.6 ml of N,N-dimethylformamide, 478 mg of potassium carbonate, and 282 mg of 2-chloroallyl chloride were added to 800 mg of compound [23f], followed by stirring at 60° C. for 3 hours. Then, water was added to the reaction mixture, which was extracted with ethyl acetate. The organic layer was washed with saturated aqueous sodium chloride solution, dried over anhydrous magnesium sulfate, and then concentrated. The residue was subjected to silica gel column chromatography (eluent, hexane:ethyl acetate=3:1), which afforded 551 mg of compound [32a].

$^1$H-NMR (300 MHz, CDCl$_3$, TMS) δ (ppm): 4.60 (2H, s), 5.48 (1H, s), 5.66–5.67 (1H, m), 6.69 (1H, s), 6.98 (1H, d, J=6.2 Hz), 7.14 (1H, s), 7.26 (1H, s), 7.40 (1H, d, J=8.9 Hz)

Then, 488 mg of compound [32a] was dissolved in 5.8 ml of N,N-diethylaniline, which was heated under reflux for 4 hours. After completion of the reaction, the reaction mixture was cooled to room temperature. Then, water was added to the reaction mixture, which was extracted with ethyl acetate. The organic layer was washed with saturated aqueous sodium chloride solution, dried over anhydrous magnesium sulfate, and then concentrated. The residue was subjected to silica gel column chromatography (eluent, hexane:ethyl acetate=3:1), which afforded 395 mg of compound [32b].

$^1$H-NMR (300 MHz, CDCl$_3$, TMS) δ (ppm): 3.50 (1H, d, J=16.3 Hz), 3.74 (1H, d, J=16.3 Hz), 4.89 (1H, d, J=1.4 Hz), 5.06 (1H, d, J=1.4 Hz), 6.67 (1H, s), 7.17 (1H, d, J=1.8 Hz), 7.2–7.3 (2H, m)

Finally, a solution of trifluoromethanesulfonic acid in 3.2 ml of chloroform was slowly added dropwise at 5° C. to a solution of 395 mg of compound [32b] in 1 ml of chloroform, followed by stirring at room temperature for 10 hours. The reaction mixture was poured into saturated aqueous sodium hydrogencarbonate solution, which was extracted with ethyl acetate. The organic layer was washed with saturated aqueous sodium chloride solution, dried over anhydrous magnesium sulfate, and then concentrated. The residue was subjected to silica gel column chromatography (eluent, toluene:ethyl acetate=15:1), which afforded 40 mg of compound [32c] (present compound 8-5).

$^1$H-NMR (300 MHz, CDCl$_3$, TMS) δ (ppm):2.47 (3H, s), 6.22 (1H, s), 6.72 (1H, s), 7.14 (1H, d, J=1.8 Hz), 7.2–7.3 (2H, m)

The production examples of the Compound [XXXVII] are shown as referential production examples below.

Referential Production Example 1

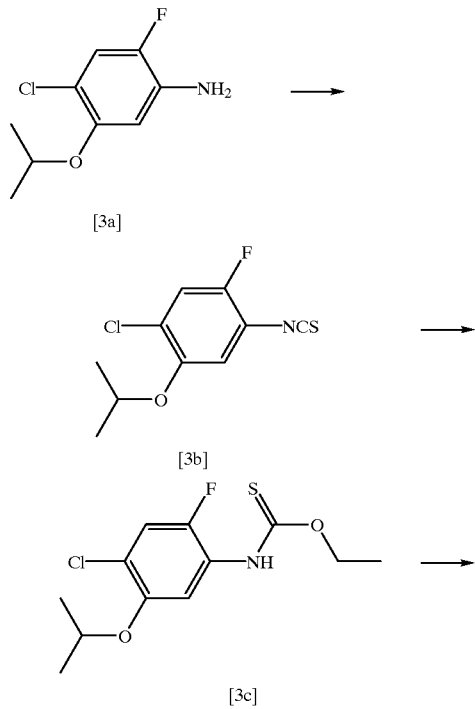

First, 50 ml of toluene and 3.4 g of thiophosgene were added to 5 g of compound [3a], which was heated under reflux for 1 hour. The reaction mixture was concentrated under reduced pressure to give compound [3b].

Then, 50 ml of ethanol was added to compound [3b], which was heated under reflux for 2 hours. The reaction mixture was concentrated under reduced pressure, and the residue was recrystallized by the addition of ethanol. The crystals were washed with hexane to give 2.8 g of compound [3c].

$^1$H-NMR (300 MHz, CDCl$_3$, TMS) δ (ppm): 1.37–1.47 (9H, m), 4.40–4.50 (1H, m), 4.60 (2H, q, J=6.9 Hz), 7.14 (1H, d, J=10.1 Hz), 7.90–8.25 (1H, br)

Then, 40 ml of toluene and 1.5 g of ethylenediamine were added to 2.7 g of compound [3c], which was heated under reflux for 7 hours. The reaction mixture was concentrated under reduced pressure, and the precipitated crystals were collected by filtration, and washed with water and then with hexane to give 2.2 g of compound [3d] (m.p., 162.8° C.).

Then, 30 ml of toluene and 3.2 ml of ethyl 4,4,4-trifluoroacetoacetate were added to 2.0 g of compound [3d], which was heated under reflux for 5 hours. The reaction mixture was concentrated under reduced pressure, and the residue was subjected to silica gel column chromatography, which afforded 0.80 g of compound [3e] (m.p., 158.200).

Then, 2 ml of concentrated sulfuric acid was added to 100 mg of compound [3e] under ice cooling, which was stirred for 10 minutes. The reaction mixture was returned to room temperature and then neutralized with aqueous sodium hydrogencarbonate solution, which was extracted with ethyl acetate. The organic layer was dried over magnesium sulfate and then concentrated under reduced pressure, which afforded 75 mg of compound [3f].

$^1$H-NMR (300 MHz, CDCl$_3$, TMS) δ (ppm): 3.95–4.27 (4H, m), 5.96 (1H, s), 6.49 (1H, d, J=6.7 Hz), 7.20 (1H, d, J=9.0 Hz).

Referential Production Example 2

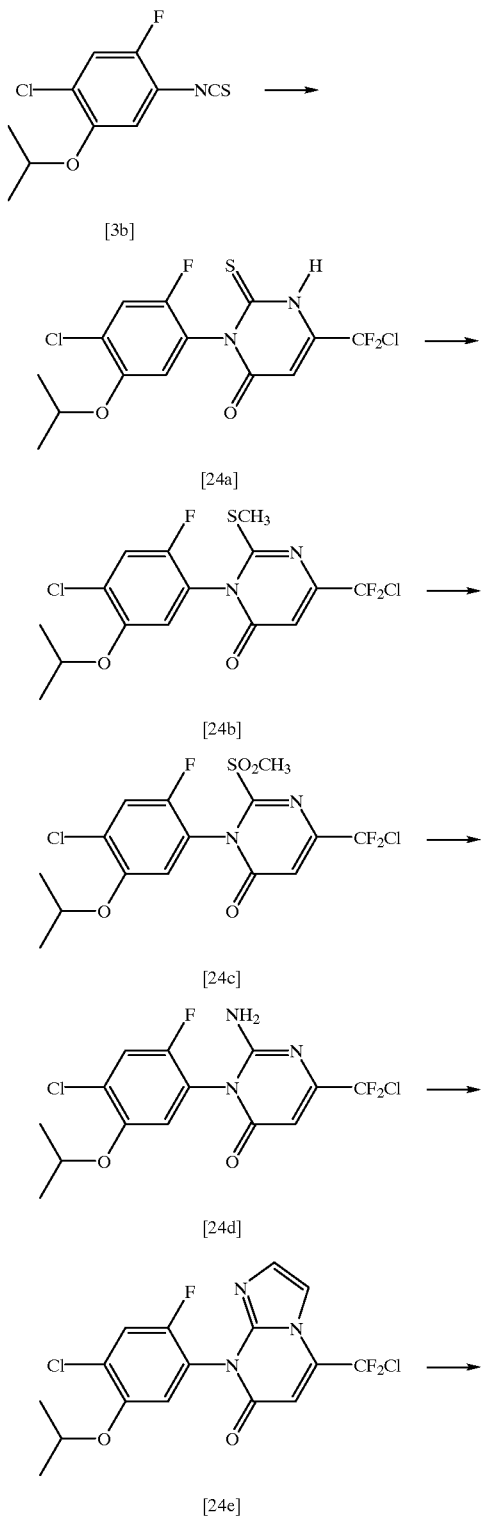

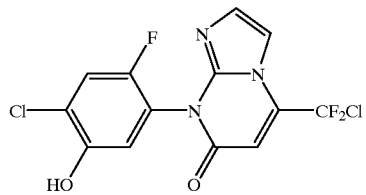

[24f]

First, 18.4 g of ethyl 3-amino-4-chloro-4,4-difluorochlotonate was added to a suspension of 3.6 g of sodium hydride in 50 ml of N,N-dimethylformamide, while keeping the reaction mixture below 10° C. The reaction mixture was stirred at room temperature for 30 minutes, to which a solution of 20.0 g of compound [3b] in 100 ml of toluene was added dropwise, while keeping the reaction mixture below 40° C. After completion of the addition, the reaction mixture was stirred at room temperature for 2 hours and then poured into water, which was neutralized with diluted hydrochloric acid and then extracted with diethyl ether. The organic layer was dried over magnesium sulfate and then concentrated. The crystals thus obtained were washed with a mixed solvent of hexane and diethyl ether (1:1) to give 8.2 g of compound [24a] (m.p., 213.7° C.).

Then, 2.5 g of triethylamine was added to a solution of 8.2 g of compound [24a] in 50 ml of N,N-dimethylformamide, followed by stirring for 30 minutes and addition of 4.4 g of iodomethane. The reaction mixture was stirred for 1 hour and then poured into water, which was neutralized with diluted hydrochloric acid and then extracted with diethyl ether. The organic layer was dried over magnesium sulfate and then concentrated to give 8.3 g of compound [24b] (m.p., 109.3° C.).

Then, 14.0 g of m-chloroperbenzoic acid was added to a solution of 8.2 g of compound [24b] in 100 ml of chloroform. The reaction mixture was stirred for 18 hours and then filtered. The filtrate was washed with aqueous sodium thiosulfate solution and then with aqueous potassium carbonate solution, dried over magnesium sulfate, and then concentrated to give 8.1 g of compound [24c] (m.p., 131.4° C.).

Then, 8.2 g of compound [24c] was suspended in 75 ml of 2-methyl-2-propanol, into which ammonia gas was blown for 30 minutes, and the reaction mixture was poured into water. The precipitated crystals were collected by filtration, washed with water, and then dried to give 5.4 g of compound [24d] (m.p., 261.3° C.).

Then, 6.0 g of 2-bromo-1,1-dimethoxyethane was added to a mixed solution of 3.0 g of concentrated hydrochloric acid and 12.0 g of acetic acid, followed by stirring at room temperature for 15 minutes and addition of 5.4 g of compound [24d]. The reaction mixture was heated under reflux for 14 hours and then poured into water, which was extracted with diethyl ether. The organic layer was washed with saturated aqueous sodium hydrogencarbonate solution, dried over magnesium sulfate, and then concentrated. The residue was subjected to silica gel chromatography (eluent, hexane:ethyl acetate=5:1), which afforded 2.9 g of compound [24e] (m.p., 112.6° C.).

Finally, 2.5 g of compound [24e] was added to 50 ml of concentrated sulfuric acid. The reaction mixture was stirred for 2 hours and then poured into ice water, which was stirred for another 1 hour and then extracted with diethyl ether. The organic layer was dried over magnesium sulfate and then concentrated, which afforded 1.4 g of compound [24f].

$^1$H-NMR (250 MHz, CDCl$_3$, TMS) δ (ppm): 6.68 (1H, s), 6.75 (1H, d, J=6.5 Hz), 7.20 (1H, d, J=1.9 Hz), 7.32 (1H, d, J=9.0 Hz), 7.38 (1H, d, J=1.9 Hz)

Some examples of the present compounds are shown, together with their compound numbers, in Tables 1 to 92. In these tables, "n", "i", "s", and "c" means "normal-", "iso-", "secondary-", and "cyclo-", respectively.

Compounds of the general formula:

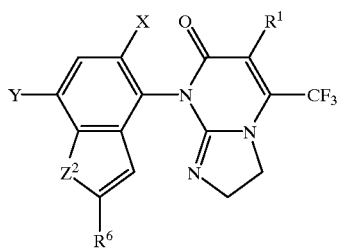

TABLE 1

| | X | Y | Z$^2$ | R$^1$ | R$^6$ |
|---|---|---|---|---|---|
| 3-1 | H | F | O | H | CH$_3$ |
| 3-2 | H | Cl | O | H | CH$_3$ |
| 3-3 | H | Br | O | H | CH$_3$ |
| 3-4 | F | F | O | H | CH$_3$ |
| 3-5 | F | Cl | O | H | CH$_3$ |
| 3-6 | F | Br | O | H | CH$_3$ |
| 3-7 | Cl | F | O | H | CH$_3$ |
| 3-8 | Cl | Cl | O | H | CH$_3$ |
| 3-9 | Cl | Br | O | H | CH$_3$ |
| 3-10 | H | F | O | H | C$_2$H$_5$ |
| 3-11 | H | Cl | O | H | C$_2$H$_5$ |
| 3-12 | H | Br | O | H | C$_2$H$_5$ |
| 3-13 | F | F | O | H | C$_2$H$_5$ |
| 3-14 | F | Cl | O | H | C$_2$H$_5$ |
| 3-15 | F | Br | O | H | C$_2$H$_5$ |
| 3-16 | Cl | F | O | H | C$_2$H$_5$ |
| 3-17 | Cl | Cl | O | H | C$_2$H$_5$ |
| 3-18 | Cl | Br | O | H | C$_2$H$_5$ |
| 3-19 | H | F | O | H | CH$_2$Br |
| 3-20 | H | Cl | O | H | CH$_2$Br |
| 3-21 | F | F | O | H | CH$_2$Br |
| 3-22 | F | Cl | O | H | CH$_2$Br |
| 3-23 | Cl | F | O | H | CH$_2$Br |
| 3-24 | Cl | Cl | O | H | CH$_2$Br |
| 3-25 | H | F | O | H | CHBr$_2$ |

TABLE 2

| | X | Y | Z$^2$ | R$^1$ | R$^6$ |
|---|---|---|---|---|---|
| 3-26 | H | Cl | O | H | CHBr$_2$ |
| 3-27 | F | F | O | H | CHBr$_2$ |
| 3-28 | F | Cl | O | H | CHBr$_2$ |
| 3-29 | Cl | F | O | H | CHBr$_2$ |
| 3-30 | Cl | Cl | O | H | CHBr$_2$ |
| 3-31 | H | F | O | H | CBr$_3$ |
| 3-32 | H | Cl | O | H | CBr$_3$ |
| 3-33 | F | F | O | H | CBr$_3$ |
| 3-34 | F | Cl | O | H | CBr$_3$ |
| 3-35 | Cl | F | O | H | CBr$_3$ |
| 3-36 | Cl | Cl | O | H | CBr$_3$ |
| 3-37 | H | F | O | H | CHO |
| 3-38 | H | Cl | O | H | CHO |
| 3-39 | F | F | O | H | CHO |
| 3-40 | F | Cl | O | H | CHO |
| 3-41 | Cl | F | O | H | CHO |

TABLE 2-continued

| | X | Y | Z$^2$ | R$^1$ | R$^6$ |
|---|---|---|---|---|---|
| 3-42 | Cl | Cl | O | H | CHO |
| 3-43 | H | F | O | H | CN |
| 3-44 | H | Cl | O | H | CN |
| 3-45 | F | F | O | H | CN |
| 3-46 | F | Cl | O | H | CN |
| 3-47 | Cl | F | O | H | CN |
| 3-48 | Cl | Cl | O | H | CN |
| 3-49 | H | F | O | H | CH$_2$OH |
| 3-50 | H | Cl | O | H | CH$_2$OH |

TABLE 3

| | X | Y | Z$^2$ | R$^1$ | R$^6$ |
|---|---|---|---|---|---|
| 3-51 | F | F | O | H | CH$_2$OH |
| 3-52 | F | Cl | O | H | CH$_2$OH |
| 3-53 | Cl | F | O | H | CH$_2$OH |
| 3-54 | Cl | Cl | O | H | CH$_2$OH |
| 3-55 | H | F | O | H | CH$_2$OCH$_3$ |
| 3-56 | H | Cl | O | H | CH$_2$OCH$_3$ |
| 3-57 | F | F | O | H | CH$_2$OCH$_3$ |
| 3-58 | F | Cl | O | H | CH$_2$OCH$_3$ |
| 3-59 | Cl | F | O | H | CH$_2$OCH$_3$ |
| 3-60 | Cl | Cl | O | H | CH$_2$OCH$_3$ |
| 3-61 | H | F | O | H | CH$_2$OC$_2$H$_5$ |
| 3-62 | H | Cl | O | H | CH$_2$OC$_2$H$_5$ |
| 3-63 | F | F | O | H | CH$_2$OC$_2$H$_5$ |
| 3-64 | F | Cl | O | H | CH$_2$OC$_2$H$_5$ |
| 3-65 | Cl | F | O | H | CH$_2$OC$_2$H$_5$ |
| 3-66 | Cl | Cl | O | H | CH$_2$OC$_2$H$_5$ |
| 3-67 | H | F | O | H | CH$_2$OiC$_3$H$_7$ |
| 3-68 | H | Cl | O | H | CH$_2$OiC$_3$H$_7$ |
| 3-69 | F | F | O | H | CH$_2$OiC$_3$H$_7$ |
| 3-70 | F | Cl | O | H | CH$_2$OiC$_3$H$_7$ |
| 3-71 | Cl | F | O | H | CH$_2$OiC$_3$H$_7$ |
| 3-72 | Cl | Cl | O | H | CH$_2$OiC$_3$H$_7$ |
| 3-73 | H | F | O | H | CH$_2$OCH$_2$OCH$_3$ |
| 3-74 | H | Cl | O | H | CH$_2$OCH$_2$OCH$_3$ |
| 3-75 | F | F | O | H | CH$_2$OCH$_2$OCH$_3$ |

TABLE 4

| | X | Y | Z$^2$ | R$^1$ | R$^6$ |
|---|---|---|---|---|---|
| 3-76 | F | Cl | O | H | CH$_2$OCH$_2$OCH$_3$ |
| 3-77 | Cl | F | O | H | CH$_2$OCH$_2$OCH$_3$ |
| 3-78 | Cl | Cl | O | H | CH$_2$OCH$_2$OCH$_3$ |
| 3-79 | H | F | O | H | CH$_2$OCH$_2$OC$_2$H$_5$ |
| 3-80 | H | Cl | O | H | CH$_2$OCH$_2$OC$_2$H$_5$ |
| 3-81 | F | F | O | H | CH$_2$OCH$_2$OC$_2$H$_5$ |
| 3-82 | F | Cl | O | H | CH$_2$OCH$_2$OC$_2$H$_5$ |
| 3-83 | Cl | F | O | H | CH$_2$OCH$_2$OC$_2$H$_5$ |
| 3-84 | Cl | Cl | O | H | CH$_2$OCH$_2$OC$_2$H$_5$ |
| 3-85 | H | F | O | H | CH$_2$OCOCH$_3$ |
| 3-86 | H | Cl | O | H | CH$_2$OCOCH$_3$ |
| 3-87 | F | F | O | H | CH$_2$OCOCH$_3$ |
| 3-88 | F | Cl | O | H | CH$_2$OCOCH$_3$ |
| 3-89 | Cl | F | O | H | CH$_2$OCOCH$_3$ |
| 3-90 | Cl | Cl | O | H | CH$_2$OCOCH$_3$ |
| 3-91 | H | F | O | H | CH$_2$OCOC$_2$H$_5$ |
| 3-92 | H | Cl | O | H | CH$_2$OCOC$_2$H$_5$ |
| 3-93 | F | F | O | H | CH$_2$OCOC$_2$H$_5$ |
| 3-94 | F | Cl | O | H | CH$_2$OCOC$_2$H$_5$ |
| 3-95 | Cl | F | O | H | CH$_2$OCOC$_2$H$_5$ |
| 3-96 | Cl | Cl | O | H | CH$_2$OCOC$_2$H$_5$ |
| 3-97 | H | F | O | H | CH$_2$OCOiC$_3$H$_7$ |
| 3-98 | H | Cl | O | H | CH$_2$OCOiC$_3$H$_7$ |
| 3-99 | F | F | O | H | CH$_2$OCOiC$_3$H$_7$ |
| 3-100 | F | Cl | O | H | CH$_2$OCOiC$_3$H$_7$ |

TABLE 5

| | X | Y | Z² | R¹ | R⁶ |
|---|---|---|---|---|---|
| 3-101 | Cl | F | O | H | $CH_2OCOiC_3H_7$ |
| 3-102 | Cl | Cl | O | H | $CH_2OCOiC_3H_7$ |
| 3-103 | H | F | O | H | $CH_2OCOCH_2Cl$ |
| 3-104 | H | Cl | O | H | $CH_2OCOCH_2Cl$ |
| 3-105 | F | F | O | H | $CH_2OCOCH_2Cl$ |
| 3-106 | F | Cl | O | H | $CH_2OCOCH_2Cl$ |
| 3-107 | Cl | F | O | H | $CH_2OCOCH_2Cl$ |
| 3-108 | Cl | Cl | O | H | $CH_2OCOCH_2Cl$ |
| 3-109 | H | F | O | H | $CH_2OCOCCl_3$ |
| 3-110 | H | Cl | O | H | $CH_2OCOCCl_3$ |
| 3-111 | F | F | O | H | $CH_2OCOCCl_3$ |
| 3-112 | F | Cl | O | H | $CH_2OCOCCl_3$ |
| 3-113 | Cl | F | O | H | $CH_2OCOCCl_3$ |
| 3-114 | Cl | Cl | O | H | $CH_2OCOCCl_3$ |
| 3-115 | H | F | O | H | $CH_2OCOCF_3$ |
| 3-116 | H | Cl | O | H | $CH_2OCOCF_3$ |
| 3-117 | F | F | O | H | $CH_2OCOCF_3$ |
| 3-118 | F | Cl | O | H | $CH_2OCOCF_3$ |
| 3-119 | Cl | F | O | H | $CH_2OCOCF_3$ |
| 3-120 | Cl | Cl | O | H | $CH_2OCOCF_3$ |
| 3-121 | H | F | O | H | COOH |
| 3-122 | H | Cl | O | H | COOH |
| 3-123 | F | F | O | H | COOH |
| 3-124 | F | Cl | O | H | COOH |
| 3-125 | Cl | F | O | H | COOH |

TABLE 6

| | X | Y | Z² | R¹ | R⁶ |
|---|---|---|---|---|---|
| 3-126 | Cl | Cl | O | H | COOH |
| 3-127 | H | F | O | H | $COOCH_3$ |
| 3-128 | H | Cl | O | H | $COOCH_3$ |
| 3-129 | F | F | O | H | $COOCH_3$ |
| 3-130 | F | Cl | O | H | $COOCH_3$ |
| 3-131 | Cl | F | O | H | $COOCH_3$ |
| 3-132 | Cl | Cl | O | H | $COOCH_3$ |
| 3-133 | H | F | O | H | $COOC_2H_5$ |
| 3-134 | H | Cl | O | H | $COOC_2H_5$ |
| 3-135 | F | F | O | H | $COOC_2H_5$ |
| 3-136 | F | Cl | O | H | $COOC_2H_5$ |
| 3-137 | Cl | F | O | H | $COOC_2H_5$ |
| 3-138 | Cl | Cl | O | H | $COOC_2H_5$ |
| 3-139 | H | F | O | H | $COOnC_3H_7$ |
| 3-140 | H | Cl | O | H | $COOnC_3H_7$ |
| 3-141 | F | F | O | H | $COOnC_3H_7$ |
| 3-142 | F | Cl | O | H | $COOnC_3H_7$ |
| 3-143 | Cl | F | O | H | $COOnC_3H_7$ |
| 3-144 | Cl | Cl | O | H | $COOnC_3H_7$ |
| 3-145 | H | F | O | H | $COOnC_4H_9$ |
| 3-146 | H | Cl | O | H | $COOnC_4H_9$ |
| 3-147 | F | F | O | H | $COOnC_4H_9$ |
| 3-148 | F | Cl | O | H | $COOnC_4H_9$ |
| 3-149 | Cl | F | O | H | $COOnC_4H_9$ |
| 3-150 | Cl | Cl | O | H | $COOnC_4H_9$ |

TABLE 7

| | X | Y | Z² | R¹ | R⁶ |
|---|---|---|---|---|---|
| 3-151 | H | F | O | H | $COOnC_5H_{11}$ |
| 3-152 | H | Cl | O | H | $COOnC_5H_{11}$ |
| 3-153 | F | F | O | H | $COOnC_5H_{11}$ |
| 3-154 | F | Cl | O | H | $COOnC_5H_{11}$ |
| 3-155 | Cl | F | O | H | $COOnC_5H_{11}$ |
| 3-156 | Cl | Cl | O | H | $COOnC_5H_{11}$ |
| 3-157 | H | F | O | H | $COOiC_3H_7$ |
| 3-158 | H | Cl | O | H | $COOiC_3H_7$ |
| 3-159 | F | F | O | H | $COOiC_3H_7$ |
| 3-160 | F | Cl | O | H | $COOiC_3H_7$ |

TABLE 7-continued

| | X | Y | Z² | R¹ | R⁶ |
|---|---|---|---|---|---|
| 3-161 | Cl | F | O | H | $COOiC_3H_7$ |
| 3-162 | Cl | Cl | O | H | $COOiC_3H_7$ |

Compounds of the general formula:

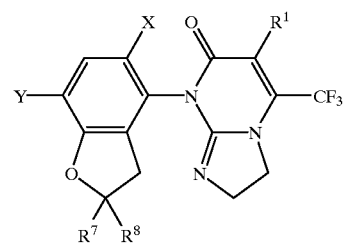

TABLE 8

| | X | Y | R¹ | R⁷ | R⁸ |
|---|---|---|---|---|---|
| 4-1 | H | F | H | H | $CH_3$ |
| 4-2 | H | Cl | H | H | $CH_3$ |
| 4-3 | H | Br | H | H | $CH_3$ |
| 4-4 | F | F | H | H | $CH_3$ |
| 4-5 | F | Cl | H | H | $CH_3$ |
| 4-6 | F | Br | H | H | $CH_3$ |
| 4-7 | Cl | F | H | H | $CH_3$ |
| 4-8 | Cl | Cl | H | H | $CH_3$ |
| 4-9 | Cl | Br | H | H | $CH_3$ |
| 4-10 | H | F | H | H | $CH_2OH$ |
| 4-11 | H | Cl | H | H | $CH_2OH$ |
| 4-12 | H | Br | H | H | $CH_2OH$ |
| 4-13 | F | F | H | H | $CH_2OH$ |
| 4-14 | F | Cl | H | H | $CH_2OH$ |
| 4-15 | F | Br | H | H | $CH_2OH$ |
| 4-16 | Cl | F | H | H | $CH_2OH$ |
| 4-17 | Cl | Cl | H | H | $CH_2OH$ |
| 4-18 | Cl | Br | H | H | $CH_2OH$ |
| 4-19 | H | F | H | H | $CH_2Cl$ |
| 4-20 | H | Cl | H | H | $CH_2Cl$ |
| 4-21 | F | F | H | H | $CH_2Cl$ |
| 4-22 | F | Cl | H | H | $CH_2Cl$ |
| 4-23 | Cl | F | H | H | $CH_2Cl$ |
| 4-24 | Cl | Cl | H | H | $CH_2Cl$ |
| 4-25 | H | F | H | H | $CH_2Br$ |

TABLE 9

| | X | Y | R¹ | R⁷ | R⁸ |
|---|---|---|---|---|---|
| 4-26 | H | Cl | H | H | $CH_2Br$ |
| 4-27 | F | F | H | H | $CH_2Br$ |
| 4-28 | F | Cl | H | H | $CH_2Br$ |
| 4-29 | Cl | F | H | H | $CH_2Br$ |
| 4-30 | Cl | Cl | H | H | $CH_2Br$ |
| 4-31 | H | F | H | H | $CH_2OCH_3$ |
| 4-32 | H | Cl | H | H | $CH_2OCH_3$ |
| 4-33 | F | F | H | H | $CH_2OCH_3$ |
| 4-34 | F | Cl | H | H | $CH_2OCH_3$ |
| 4-35 | Cl | F | H | H | $CH_2OCH_3$ |
| 4-36 | Cl | Cl | H | H | $CH_2OCH_3$ |
| 4-37 | H | F | H | H | $CH_2OC_2H_5$ |
| 4-38 | H | Cl | H | H | $CH_2OC_2H_5$ |
| 4-39 | F | F | H | H | $CH_2OC_2H_5$ |
| 4-40 | F | Cl | H | H | $CH_2OC_2H_5$ |
| 4-41 | Cl | F | H | H | $CH_2OC_2H_5$ |
| 4-42 | Cl | Cl | H | H | $CH_2OC_2H_5$ |
| 4-43 | H | F | H | H | $CH_2OiC_3H_7$ |
| 4-44 | H | Cl | H | H | $CH_2OiC_3H_7$ |

TABLE 9-continued

|  | X | Y | R$^1$ | R$^7$ | R$^8$ |
|---|---|---|---|---|---|
| 4-45 | F | F | H | H | CH$_2$OiC$_3$H$_7$ |
| 4-46 | F | Cl | H | H | CH$_2$OiC$_3$H$_7$ |
| 4-47 | Cl | F | H | H | CH$_2$OiC$_3$H$_7$ |
| 4-48 | Cl | Cl | H | H | CH$_2$OiC$_3$H$_7$ |
| 4-49 | H | F | H | H | CH$_2$OCH$_2$OCH$_3$ |
| 4-50 | H | Cl | H | H | CH$_2$OCH$_2$OCH$_3$ |

TABLE 10

|  | X | Y | R$^1$ | R$^7$ | R$^8$ |
|---|---|---|---|---|---|
| 4-51 | F | F | H | H | CH$_2$OCH$_2$OCH$_3$ |
| 4-52 | F | Cl | H | H | CH$_2$OCH$_2$OCH$_3$ |
| 4-53 | Cl | F | H | H | CH$_2$OCH$_2$OCH$_3$ |
| 4-54 | Cl | Cl | H | H | CH$_2$OCH$_2$OCH$_3$ |
| 4-55 | H | F | H | H | CH$_2$OCH$_2$OC$_2$H$_5$ |
| 4-56 | H | Cl | H | H | CH$_2$OCH$_2$OC$_2$H$_5$ |
| 4-57 | F | F | H | H | CH$_2$OCH$_2$OC$_2$H$_5$ |
| 4-58 | F | Cl | H | H | CH$_2$OCH$_2$OC$_2$H$_5$ |
| 4-59 | Cl | F | H | H | CH$_2$OCH$_2$OC$_2$H$_5$ |
| 4-60 | Cl | Cl | H | H | CH$_2$OCH$_2$OC$_2$H$_5$ |
| 4-61 | H | F | H | H | CH$_2$OCOCH$_3$ |
| 4-62 | H | Cl | H | H | CH$_2$OCOCH$_3$ |
| 4-63 | F | F | H | H | CH$_2$OCOCH$_3$ |
| 4-64 | F | Cl | H | H | CH$_2$OCOCH$_3$ |
| 4-65 | Cl | F | H | H | CH$_2$OCOCH$_3$ |
| 4-66 | Cl | Cl | H | H | CH$_2$OCOCH$_3$ |
| 4-67 | H | F | H | H | CH$_2$OCOC$_2$H$_5$ |
| 4-68 | H | Cl | H | H | CH$_2$OCOC$_2$H$_5$ |
| 4-69 | F | F | H | H | CH$_2$OCOC$_2$H$_5$ |
| 4-70 | F | Cl | H | H | CH$_2$OCOC$_2$H$_5$ |
| 4-71 | Cl | F | H | H | CH$_2$OCOC$_2$H$_5$ |
| 4-72 | Cl | Cl | H | H | CH$_2$OCOC$_2$H$_5$ |
| 4-73 | H | F | H | H | CH$_2$OCOiC$_3$H$_7$ |
| 4-74 | H | Cl | H | H | CH$_2$OCOiC$_3$H$_7$ |
| 4-75 | F | F | H | H | CH$_2$OCOiC$_3$H$_7$ |

TABLE 11

|  | X | Y | R$^1$ | R$^7$ | R$^8$ |
|---|---|---|---|---|---|
| 4-76 | F | Cl | H | H | CH$_2$OCOiC$_3$H$_7$ |
| 4-77 | Cl | F | H | H | CH$_2$OCOiC$_3$H$_7$ |
| 4-78 | Cl | Cl | H | H | CH$_2$OCOiC$_3$H$_7$ |
| 4-79 | H | F | H | H | CH$_2$OCOCH$_2$Cl |
| 4-80 | H | Cl | H | H | CH$_2$OCOCH$_2$Cl |
| 4-81 | F | F | H | H | CH$_2$OCOCH$_2$Cl |
| 4-82 | F | Cl | H | H | CH$_2$OCOCH$_2$Cl |
| 4-83 | Cl | F | H | H | CH$_2$OCOCH$_2$Cl |
| 4-84 | Cl | Cl | H | H | CH$_2$OCOCH$_2$Cl |
| 4-85 | H | F | H | H | CH$_2$OCOCCl$_3$ |
| 4-86 | H | Cl | H | H | CH$_2$OCOCCl$_3$ |
| 4-87 | F | F | H | H | CH$_2$OCOCCl$_3$ |
| 4-88 | F | Cl | H | H | CH$_2$OCOCCl$_3$ |
| 4-89 | Cl | F | H | H | CH$_2$OCOCCl$_3$ |
| 4-90 | Cl | Cl | H | H | CH$_2$OCOCCl$_3$ |
| 4-91 | H | F | H | H | CH$_2$OCOCF$_3$ |
| 4-92 | H | Cl | H | H | CH$_2$OCOCF$_3$ |
| 4-93 | F | F | H | H | CH$_2$OCOCF$_3$ |
| 4-94 | F | Cl | H | H | CH$_2$OCOCF$_3$ |
| 4-95 | Cl | F | H | H | CH$_2$OCOCF$_3$ |
| 4-96 | Cl | Cl | H | H | CH$_2$OCOCF$_3$ |
| 4-97 | H | F | H | H | COOH |
| 4-98 | H | Cl | H | H | COOH |
| 4-99 | F | F | H | H | COOH |
| 4-100 | F | Cl | H | H | COOH |

TABLE 12

|  | X | Y | R$^1$ | R$^7$ | R$^8$ |
|---|---|---|---|---|---|
| 4-101 | Cl | F | H | H | COOH |
| 4-102 | Cl | Cl | H | H | COOH |
| 4-103 | H | F | H | H | COOCH$_3$ |
| 4-104 | H | Cl | H | H | COOCH$_3$ |
| 4-105 | F | F | H | H | COOCH$_3$ |
| 4-106 | F | Cl | H | H | COOCH$_3$ |
| 4-107 | Cl | F | H | H | COOCH$_3$ |
| 4-108 | Cl | Cl | H | H | COOCH$_3$ |
| 4-109 | H | F | H | H | COOC$_2$H$_5$ |
| 4-110 | H | Cl | H | H | COOC$_2$H$_5$ |
| 4-111 | F | F | H | H | COOC$_2$H$_5$ |
| 4-112 | F | Cl | H | H | COOC$_2$H$_5$ |
| 4-113 | Cl | F | H | H | COOC$_2$H$_5$ |
| 4-114 | Cl | Cl | H | H | COOC$_2$H$_5$ |
| 4-115 | H | F | H | H | COOnC$_3$H$_7$ |
| 4-116 | H | Cl | H | H | COOnC$_3$H$_7$ |
| 4-117 | F | F | H | H | COOnC$_3$H$_7$ |
| 4-118 | F | Cl | H | H | COOnC$_3$H$_7$ |
| 4-119 | Cl | F | H | H | COOnC$_3$H$_7$ |
| 4-120 | Cl | Cl | H | H | COOnC$_3$H$_7$ |
| 4-121 | H | F | H | H | COOnC$_4$H$_9$ |
| 4-122 | H | Cl | H | H | COOnC$_4$H$_9$ |
| 4-123 | F | F | H | H | COOnC$_4$H$_9$ |
| 4-124 | F | Cl | H | H | COOnC$_4$H$_9$ |
| 4-125 | Cl | F | H | H | COOnC$_4$H$_9$ |

TABLE 13

|  | X | Y | R$^1$ | R$^7$ | R$^8$ |
|---|---|---|---|---|---|
| 4-126 | Cl | Cl | H | H | COOnC$_4$H$_9$ |
| 4-127 | H | F | H | H | COOnC$_5$H$_{11}$ |
| 4-128 | H | Cl | H | H | COOnC$_5$H$_{11}$ |
| 4-129 | F | F | H | H | COOnC$_5$H$_{11}$ |
| 4-130 | F | Cl | H | H | COOnC$_5$H$_{11}$ |
| 4-131 | Cl | F | H | H | COOnC$_5$H$_{11}$ |
| 4-132 | Cl | Cl | H | H | COOnC$_5$H$_{11}$ |
| 4-133 | H | F | H | H | COOiC$_3$H$_7$ |
| 4-134 | H | Cl | H | H | COOiC$_3$H$_7$ |
| 4-135 | F | F | H | H | COOiC$_3$H$_7$ |
| 4-136 | F | Cl | H | H | COOiC$_3$H$_7$ |
| 4-137 | Cl | F | H | H | COOiC$_3$H$_7$ |
| 4-138 | Cl | Cl | H | H | COOiC$_3$H$_7$ |
| 4-139 | H | F | H | H | COOcC$_5$H$_9$ |
| 4-140 | H | Cl | H | H | COOcC$_5$H$_9$ |
| 4-141 | F | F | H | H | COOcC$_5$H$_9$ |
| 4-142 | F | Cl | H | H | COOcC$_5$H$_9$ |
| 4-143 | Cl | F | H | H | COOcC$_5$H$_9$ |
| 4-144 | Cl | Cl | H | H | COOcC$_5$H$_9$ |
| 4-145 | H | F | H | H | COOcC$_6$H$_{11}$ |
| 4-146 | H | Cl | H | H | COOcC$_6$H$_{11}$ |
| 4-147 | F | F | H | H | COOcC$_6$H$_{11}$ |
| 4-148 | F | Cl | H | H | COOcC$_6$H$_{11}$ |
| 4-149 | Cl | F | H | H | COOcC$_6$H$_{11}$ |
| 4-150 | Cl | Cl | H | H | COOcC$_6$H$_{11}$ |

TABLE 14

|  | X | Y | R$^1$ | R$^7$ | R$^8$ |
|---|---|---|---|---|---|
| 4-151 | H | F | H | H | COOCH$_2$CH=CH$_2$ |
| 4-152 | H | Cl | H | H | COOCH$_2$CH=CH$_2$ |
| 4-153 | F | F | H | H | COOCH$_2$CH=CH$_2$ |
| 4-154 | F | Cl | H | H | COOCH$_2$CH=CH$_2$ |
| 4-155 | Cl | F | H | H | COOCH$_2$CH=CH$_2$ |
| 4-156 | Cl | Cl | H | H | COOCH$_2$CH=CH$_2$ |
| 4-157 | H | F | H | H | COOCH$_2$C≡CH |
| 4-158 | H | Cl | H | H | COOCH$_2$C≡CH |
| 4-159 | F | F | H | H | COOCH$_2$C≡CH |
| 4-160 | F | Cl | H | H | COOCH$_2$C≡CH |
| 4-161 | Cl | F | H | H | COOCH$_2$C≡CH |
| 4-162 | Cl | Cl | H | H | COOCH$_2$C≡CH |

TABLE 14-continued

|  | X | Y | $R^1$ | $R^7$ | $R^8$ |
|---|---|---|---|---|---|
| 4-163 | H | F | H | H | $CONH_2$ |
| 4-164 | H | Cl | H | H | $CONH_2$ |
| 4-165 | F | F | H | H | $CONH_2$ |
| 4-166 | F | Cl | H | H | $CONH_2$ |
| 4-167 | Cl | F | H | H | $CONH_2$ |
| 4-168 | Cl | Cl | H | H | $CONH_2$ |
| 4-169 | H | F | H | H | $CONHCH_3$ |
| 4-170 | H | Cl | H | H | $CONHCH_3$ |
| 4-171 | F | F | H | H | $CONHCH_3$ |
| 4-172 | F | Cl | H | H | $CONHCH_3$ |
| 4-173 | Cl | F | H | H | $CONHCH_3$ |
| 4-174 | Cl | Cl | H | H | $CONHCH_3$ |
| 4-175 | H | F | H | H | $CONHC_2H_5$ |

TABLE 15

|  | X | Y | $R^1$ | $R^7$ | $R^8$ |
|---|---|---|---|---|---|
| 4-176 | H | Cl | H | H | $CONHC_2H_5$ |
| 4-177 | F | F | H | H | $CONHC_2H_5$ |
| 4-178 | F | Cl | H | H | $CONHC_2H_5$ |
| 4-179 | Cl | F | H | H | $CONHC_2H_5$ |
| 4-180 | Cl | Cl | H | H | $CONHC_2H_5$ |
| 4-181 | H | F | H | H | $CON(CH_3)_2$ |
| 4-182 | H | Cl | H | H | $CON(CH_3)_2$ |
| 4-183 | F | F | H | H | $CON(CH_3)_2$ |
| 4-184 | F | Cl | H | H | $CON(CH_3)_2$ |
| 4-185 | Cl | F | H | H | $CON(CH_3)_2$ |
| 4-186 | Cl | Cl | H | H | $CON(CH_3)_2$ |
| 4-187 | H | F | H | H | $CON(C_2H_5)_2$ |
| 4-188 | H | Cl | H | H | $CON(C_2H_5)_2$ |
| 4-189 | F | F | H | H | $CON(C_2H_5)_2$ |
| 4-190 | F | Cl | H | H | $CON(C_2H_5)_2$ |
| 4-191 | Cl | F | H | H | $CON(C_2H_5)_2$ |
| 4-192 | Cl | Cl | H | H | $CON(C_2H_5)_2$ |
| 4-193 | H | F | H | $CH_3$ | $CH_3$ |
| 4-194 | H | Cl | H | $CH_3$ | $CH_3$ |
| 4-195 | H | Br | H | $CH_3$ | $CH_3$ |
| 4-196 | F | F | H | $CH_3$ | $CH_3$ |
| 4-197 | F | Cl | H | $CH_3$ | $CH_3$ |
| 4-198 | F | Br | H | $CH_3$ | $CH_3$ |
| 4-199 | Cl | F | H | $CH_3$ | $CH_3$ |
| 4-200 | Cl | Cl | H | $CH_3$ | $CH_3$ |

TABLE 16

|  | X | Y | $R^1$ | $R^7$ | $R^8$ |
|---|---|---|---|---|---|
| 4-201 | Cl | Br | H | $CH_3$ | $CH_3$ |
| 4-202 | H | F | H | $CH_3$ | $CH_2OH$ |
| 4-203 | H | Cl | H | $CH_3$ | $CH_2OH$ |
| 4-204 | H | Br | H | $CH_3$ | $CH_2OH$ |
| 4-205 | F | F | H | $CH_3$ | $CH_2OH$ |
| 4-206 | F | Cl | H | $CH_3$ | $CH_2OH$ |
| 4-207 | F | Br | H | $CH_3$ | $CH_2OH$ |
| 4-208 | Cl | F | H | $CH_3$ | $CH_2OH$ |
| 4-209 | Cl | Cl | H | $CH_3$ | $CH_2OH$ |
| 4-210 | Cl | Br | H | $CH_3$ | $CH_2OH$ |
| 4-211 | H | F | H | $CH_3$ | $CH_2Cl$ |
| 4-212 | H | Cl | H | $CH_3$ | $CH_2Cl$ |
| 4-213 | F | F | H | $CH_3$ | $CH_2Cl$ |
| 4-214 | F | Cl | H | $CH_3$ | $CH_2Cl$ |
| 4-215 | Cl | F | H | $CH_3$ | $CH_2Cl$ |
| 4-216 | Cl | Cl | H | $CH_3$ | $CH_2Cl$ |
| 4-217 | H | F | H | $CH_3$ | $CH_2Br$ |
| 4-218 | H | Cl | H | $CH_3$ | $CH_2Br$ |
| 4-219 | F | F | H | $CH_3$ | $CH_2Br$ |
| 4-220 | F | Cl | H | $CH_3$ | $CH_2Br$ |
| 4-221 | Cl | F | H | $CH_3$ | $CH_2Br$ |
| 4-222 | Cl | Cl | H | $CH_3$ | $CH_2Br$ |
| 4-223 | H | F | H | $CH_3$ | $CH_2OCH_3$ |

TABLE 16-continued

|  | X | Y | $R^1$ | $R^7$ | $R^8$ |
|---|---|---|---|---|---|
| 4-224 | H | Cl | H | $CH_3$ | $CH_2OCH_3$ |
| 4-225 | F | F | H | $CH_3$ | $CH_2OCH_3$ |

TABLE 17

|  | X | Y | $R^1$ | $R^7$ | $R^8$ |
|---|---|---|---|---|---|
| 4-226 | F | Cl | H | $CH_3$ | $CH_2OCH_3$ |
| 4-227 | Cl | F | H | $CH_3$ | $CH_2OCH_3$ |
| 4-228 | Cl | Cl | H | $CH_3$ | $CH_2OCH_3$ |
| 4-229 | H | F | H | $CH_3$ | $CH_2OC_2H_5$ |
| 4-230 | H | Cl | H | $CH_3$ | $CH_2OC_2H_5$ |
| 4-231 | F | F | H | $CH_3$ | $CH_2OC_2H_5$ |
| 4-232 | F | Cl | H | $CH_3$ | $CH_2OC_2H_5$ |
| 4-233 | Cl | F | H | $CH_3$ | $CH_2OC_2H_5$ |
| 4-234 | Cl | Cl | H | $CH_3$ | $CH_2OC_2H_5$ |
| 4-235 | H | F | H | $CH_3$ | $CH_2OiC_3H_7$ |
| 4-236 | H | Cl | H | $CH_3$ | $CH_2OiC_3H_7$ |
| 4-237 | F | F | H | $CH_3$ | $CH_2OiC_3H_7$ |
| 4-238 | F | Cl | H | $CH_3$ | $CH_2OiC_3H_7$ |
| 4-239 | Cl | F | H | $CH_3$ | $CH_2OiC_3H_7$ |
| 4-240 | Cl | Cl | H | $CH_3$ | $CH_2OiC_3H_7$ |
| 4-241 | H | F | H | $CH_3$ | $CH_2OCH_2OCH_3$ |
| 4-242 | H | Cl | H | $CH_3$ | $CH_2OCH_2OCH_3$ |
| 4-243 | F | F | H | $CH_3$ | $CH_2OCH_2OCH_3$ |
| 4-244 | F | Cl | H | $CH_3$ | $CH_2OCH_2OCH_3$ |
| 4-245 | Cl | F | H | $CH_3$ | $CH_2OCH_2OCH_3$ |
| 4-246 | Cl | Cl | H | $CH_3$ | $CH_2OCH_2OCH_3$ |
| 4-247 | H | F | H | $CH_3$ | $CH_2OCH_2OC_2H_5$ |
| 4-248 | H | Cl | H | $CH_3$ | $CH_2OCH_2OC_2H_5$ |
| 4-249 | F | F | H | $CH_3$ | $CH_2OCH_2OC_2H_5$ |
| 4-250 | F | Cl | H | $CH_3$ | $CH_2OCH_2OC_2H_5$ |

TABLE 18

|  | X | Y | $R^1$ | $R^7$ | $R^8$ |
|---|---|---|---|---|---|
| 4-251 | Cl | F | H | $CH_3$ | $CH_2OCH_2OC_2H_5$ |
| 4-252 | Cl | Cl | H | $CH_3$ | $CH_2OCH_2OC_2H_5$ |
| 4-253 | H | F | H | $CH_3$ | $CH_2OCOCH_3$ |
| 4-254 | H | Cl | H | $CH_3$ | $CH_2OCOCH_3$ |
| 4-255 | F | F | H | $CH_3$ | $CH_2OCOCH_3$ |
| 4-256 | F | Cl | H | $CH_3$ | $CH_2OCOCH_3$ |
| 4-257 | Cl | F | H | $CH_3$ | $CH_2OCOCH_3$ |
| 4-258 | Cl | Cl | H | $CH_3$ | $CH_2OCOCH_3$ |
| 4-259 | H | F | H | $CH_3$ | $CH_2OCOC_2H_5$ |
| 4-260 | H | Cl | H | $CH_3$ | $CH_2OCOC_2H_5$ |
| 4-261 | F | F | H | $CH_3$ | $CH_2OCOC_2H_5$ |
| 4-262 | F | Cl | H | $CH_3$ | $CH_2OCOC_2H_5$ |
| 4-263 | Cl | F | H | $CH_3$ | $CH_2OCOC_2H_5$ |
| 4-264 | Cl | Cl | H | $CH_3$ | $CH_2OCOC_2H_5$ |
| 4-265 | H | F | H | $CH_3$ | $CH_2OCOiC_3H_7$ |
| 4-266 | H | Cl | H | $CH_3$ | $CH_2OCOiC_3H_7$ |
| 4-267 | F | F | H | $CH_3$ | $CH_2OCOiC_3H_7$ |
| 4-268 | F | Cl | H | $CH_3$ | $CH_2OCOiC_3H_7$ |
| 4-269 | Cl | F | H | $CH_3$ | $CH_2OCOiC_3H_7$ |
| 4-270 | Cl | Cl | H | $CH_3$ | $CH_2OCOiC_3H_7$ |
| 4-271 | H | F | H | $CH_3$ | $CH_2OCOCH_2Cl$ |
| 4-272 | H | Cl | H | $CH_3$ | $CH_2OCOCH_2Cl$ |
| 4-273 | F | F | H | $CH_3$ | $CH_2OCOCH_2Cl$ |
| 4-274 | F | Cl | H | $CH_3$ | $CH_2OCOCH_2Cl$ |
| 4-275 | Cl | F | H | $CH_3$ | $CH_2OCOCH_2Cl$ |

TABLE 19

|  | X | Y | $R^1$ | $R^7$ | $R^8$ |
|---|---|---|---|---|---|
| 4-276 | Cl | Cl | H | $CH_3$ | $CH_2OCOCH_2Cl$ |
| 4-277 | H | F | H | $CH_3$ | $CH_2OCOCCl_3$ |
| 4-278 | H | Cl | H | $CH_3$ | $CH_2OCOCCl_3$ |

TABLE 19-continued

|  | X | Y | R$^1$ | R$^7$ | R$^8$ |
|---|---|---|---|---|---|
| 4-279 | F | F | H | CH$_3$ | CH$_2$OCOCCl$_3$ |
| 4-280 | F | Cl | H | CH$_3$ | CH$_2$OCOCCl$_3$ |
| 4-281 | Cl | F | H | CH$_3$ | CH$_2$OCOCCl$_3$ |
| 4-282 | Cl | Cl | H | CH$_3$ | CH$_2$OCOCCl$_3$ |
| 4-283 | H | F | H | CH$_3$ | CH$_2$OCOCF$_3$ |
| 4-284 | H | Cl | H | CH$_3$ | CH$_2$OCOCF$_3$ |
| 4-285 | F | F | H | CH$_3$ | CH$_2$OCOCF$_3$ |
| 4-286 | F | Cl | H | CH$_3$ | CH$_2$OCOCF$_3$ |
| 4-287 | Cl | F | H | CH$_3$ | CH$_2$OCOCF$_3$ |
| 4-288 | Cl | Cl | H | CH$_3$ | CH$_2$OCOCF$_3$ |
| 4-289 | H | F | H | CH$_3$ | COOH |
| 4-290 | H | Cl | H | CH$_3$ | COOH |
| 4-291 | F | F | H | CH$_3$ | COOH |
| 4-292 | F | Cl | H | CH$_3$ | COOH |
| 4-293 | Cl | F | H | CH$_3$ | COOH |
| 4-294 | Cl | Cl | H | CH$_3$ | COOH |
| 4-295 | H | F | H | CH$_3$ | COOCH$_3$ |
| 4-296 | H | Cl | H | CH$_3$ | COOCH$_3$ |
| 4-297 | F | F | H | CH$_3$ | COOCH$_3$ |
| 4-298 | F | Cl | H | CH$_3$ | COOCH$_3$ |
| 4-299 | Cl | F | H | CH$_3$ | COOCH$_3$ |
| 4-300 | Cl | Cl | H | CH$_3$ | COOCH$_3$ |

TABLE 20

|  | X | Y | R$^1$ | R$^7$ | R$^8$ |
|---|---|---|---|---|---|
| 4-301 | H | F | H | CH$_3$ | COOC$_2$H$_5$ |
| 4-302 | H | Cl | H | CH$_3$ | COOC$_2$H$_5$ |
| 4-303 | F | F | H | CH$_3$ | COOC$_2$H$_5$ |
| 4-304 | F | Cl | H | CH$_3$ | COOC$_2$H$_5$ |
| 4-305 | Cl | F | H | CH$_3$ | COOC$_2$H$_5$ |
| 4-306 | Cl | Cl | H | CH$_3$ | COOC$_2$H$_5$ |
| 4-307 | H | F | H | CH$_3$ | COOnC$_3$H$_7$ |
| 4-308 | H | Cl | H | CH$_3$ | COOnC$_3$H$_7$ |
| 4-309 | F | F | H | CH$_3$ | COOnC$_3$H$_7$ |
| 4-310 | F | Cl | H | CH$_3$ | COOnC$_3$H$_7$ |
| 4-311 | Cl | F | H | CH$_3$ | COOnC$_3$H$_7$ |
| 4-312 | Cl | Cl | H | CH$_3$ | COOnC$_3$H$_7$ |
| 4-313 | H | F | H | CH$_3$ | COOnC$_4$H$_9$ |
| 4-314 | H | Cl | H | CH$_3$ | COOnC$_4$H$_9$ |
| 4-315 | F | F | H | CH$_3$ | COOnC$_4$H$_9$ |
| 4-316 | F | Cl | H | CH$_3$ | COOnC$_4$H$_9$ |
| 4-317 | Cl | F | H | CH$_3$ | COOnC$_4$H$_9$ |
| 4-318 | Cl | Cl | H | CH$_3$ | COOnC$_4$H$_9$ |
| 4-319 | H | F | H | CH$_3$ | COOnC$_5$H$_{11}$ |
| 4-320 | H | Cl | H | CH$_3$ | COOnC$_5$H$_{11}$ |
| 4-321 | F | F | H | CH$_3$ | COOnC$_5$H$_{11}$ |
| 4-322 | F | Cl | H | CH$_3$ | COOnC$_5$H$_{11}$ |
| 4-323 | Cl | F | H | CH$_3$ | COOnC$_5$H$_{11}$ |
| 4-324 | Cl | Cl | H | CH$_3$ | COOnC$_5$H$_{11}$ |
| 4-325 | H | F | H | CH$_3$ | COOiC$_3$H$_7$ |

TABLE 21

|  | X | Y | R$^1$ | R$^7$ | R$^8$ |
|---|---|---|---|---|---|
| 4-326 | H | Cl | H | CH$_3$ | COOiC$_3$H$_7$ |
| 4-327 | F | F | H | CH$_3$ | COOiC$_3$H$_7$ |
| 4-328 | F | Cl | H | CH$_3$ | COOiC$_3$H$_7$ |
| 4-329 | Cl | F | H | CH$_3$ | COOiC$_3$H$_7$ |
| 4-330 | Cl | Cl | H | CH$_3$ | COOiC$_3$H$_7$ |
| 4-331 | H | F | H | CH$_3$ | COOcC$_5$H$_9$ |
| 4-332 | H | Cl | H | CH$_3$ | COOcC$_5$H$_9$ |
| 4-333 | F | F | H | CH$_3$ | COOcC$_5$H$_9$ |
| 4-334 | F | Cl | H | CH$_3$ | COOcC$_5$H$_9$ |
| 4-335 | Cl | F | H | CH$_3$ | COOcC$_5$H$_9$ |
| 4-336 | Cl | Cl | H | CH$_3$ | COOcC$_5$H$_9$ |
| 4-337 | H | F | H | CH$_3$ | COOcC$_6$H$_{11}$ |
| 4-338 | H | Cl | H | CH$_3$ | COOcC$_6$H$_{11}$ |
| 4-339 | F | F | H | CH$_3$ | COOcC$_6$H$_{11}$ |
| 4-340 | F | Cl | H | CH$_3$ | COOcC$_6$H$_{11}$ |

TABLE 21-continued

|  | X | Y | R$^1$ | R$^7$ | R$^8$ |
|---|---|---|---|---|---|
| 4-341 | Cl | F | H | CH$_3$ | COOcC$_6$H$_{11}$ |
| 4-342 | Cl | Cl | H | CH$_3$ | COOcC$_6$H$_{11}$ |
| 4-343 | H | F | H | CH$_3$ | COOCH$_2$CH=CH$_2$ |
| 4-344 | H | Cl | H | CH$_3$ | COOCH$_2$CH=CH$_2$ |
| 4-345 | F | F | H | CH$_3$ | COOCH$_2$CH=CH$_2$ |
| 4-346 | F | Cl | H | CH$_3$ | COOCH$_2$CH=CH$_2$ |
| 4-347 | Cl | F | H | CH$_3$ | COOCH$_2$CH=CH$_2$ |
| 4-348 | Cl | Cl | H | CH$_3$ | COOCH$_2$CH=CH$_2$ |
| 4-349 | H | F | H | CH$_3$ | COOCH$_2$C≡CH |
| 4-350 | H | Cl | H | CH$_3$ | COOCH$_2$C≡CH |

TABLE 22

|  | X | Y | R$^1$ | R$^7$ | R$^8$ |
|---|---|---|---|---|---|
| 4-351 | F | F | H | CH$_3$ | COOCH$_2$C≡CH |
| 4-352 | F | Cl | H | CH$_3$ | COOCH$_2$C≡CH |
| 4-353 | Cl | F | H | CH$_3$ | COOCH$_2$C≡CH |
| 4-354 | Cl | Cl | H | CH$_3$ | COOCH$_2$C≡CH |
| 4-355 | H | F | H | CH$_3$ | CONH$_2$ |
| 4-356 | H | Cl | H | CH$_3$ | CONH$_2$ |
| 4-357 | F | F | H | CH$_3$ | CONH$_2$ |
| 4-358 | F | Cl | H | CH$_3$ | CONH$_2$ |
| 4-359 | Cl | F | H | CH$_3$ | CONH$_2$ |
| 4-360 | Cl | Cl | H | CH$_3$ | CONH$_2$ |
| 4-361 | H | F | H | CH$_3$ | CONHCH$_3$ |
| 4-362 | H | Cl | H | CH$_3$ | CONHCH$_3$ |
| 4-363 | F | F | H | CH$_3$ | CONHCH$_3$ |
| 4-364 | F | Cl | H | CH$_3$ | CONHCH$_3$ |
| 4-365 | Cl | F | H | CH$_3$ | CONHCH$_3$ |
| 4-366 | Cl | Cl | H | CH$_3$ | CONHCH$_3$ |
| 4-367 | H | F | H | CH$_3$ | CONHC$_2$H$_5$ |
| 4-368 | H | Cl | H | CH$_3$ | CONHC$_2$H$_5$ |
| 4-369 | F | F | H | CH$_3$ | CONHC$_2$H$_5$ |
| 4-370 | F | Cl | H | CH$_3$ | CONHC$_2$H$_5$ |
| 4-371 | Cl | F | H | CH$_3$ | CONHC$_2$H$_5$ |
| 4-372 | Cl | Cl | H | CH$_3$ | CONHC$_2$H$_5$ |
| 4-373 | H | F | H | CH$_3$ | CON(CH$_3$)$_2$ |
| 4-374 | H | Cl | H | CH$_3$ | CON(CH$_3$)$_2$ |
| 4-375 | F | F | H | CH$_3$ | CON(CH$_3$)$_2$ |

TABLE 23

|  | X | Y | R$^1$ | R$^7$ | R$^8$ |
|---|---|---|---|---|---|
| 4-376 | F | Cl | H | CH$_3$ | CON(CH$_3$)$_2$ |
| 4-377 | Cl | F | H | CH$_3$ | CON(CH$_3$)$_2$ |
| 4-378 | Cl | Cl | H | CH$_3$ | CON(CH$_3$)$_2$ |
| 4-379 | H | F | H | CH$_3$ | CON(C$_2$H$_5$)$_2$ |
| 4-380 | H | Cl | H | CH$_3$ | CON(C$_2$H$_5$)$_2$ |
| 4-381 | F | F | H | CH$_3$ | CON(C$_2$H$_5$)$_2$ |
| 4-382 | F | Cl | H | CH$_3$ | CON(C$_2$H$_5$)$_2$ |
| 4-383 | Cl | F | H | CH$_3$ | CON(C$_2$H$_5$)$_2$ |
| 4-384 | Cl | Cl | H | CH$_3$ | CON(C$_2$H$_5$)$_2$ |

Compounds of the general formula:

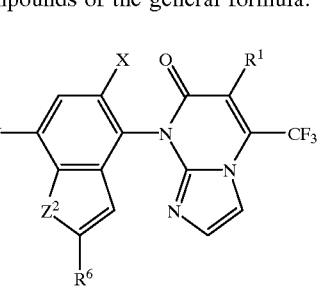

TABLE 24

|      | X  | Y  | $Z^2$ | $R^1$ | $R^6$ |
|------|----|----|----|----|------|
| 8-1  | H  | F  | O  | H  | $CH_3$ |
| 8-2  | H  | Cl | O  | H  | $CH_3$ |
| 8-3  | H  | Br | O  | H  | $CH_3$ |
| 8-4  | F  | F  | O  | H  | $CH_3$ |
| 8-5  | F  | Cl | O  | H  | $CH_3$ |
| 8-6  | F  | Br | O  | H  | $CH_3$ |
| 8-7  | Cl | F  | O  | H  | $CH_3$ |
| 8-8  | Cl | Cl | O  | H  | $CH_3$ |
| 8-9  | Cl | Br | O  | H  | $CH_3$ |
| 8-10 | H  | F  | O  | H  | $C_2H_5$ |
| 8-11 | H  | Cl | O  | H  | $C_2H_5$ |
| 8-12 | H  | Br | O  | H  | $C_2H_5$ |
| 8-13 | F  | F  | O  | H  | $C_2H_5$ |
| 8-14 | F  | Cl | O  | H  | $C_2H_5$ |
| 8-15 | F  | Br | O  | H  | $C_2H_5$ |
| 8-16 | Cl | F  | O  | H  | $C_2H_5$ |
| 8-17 | Cl | Cl | O  | H  | $C_2H_5$ |
| 8-18 | Cl | Br | O  | H  | $C_2H_5$ |
| 8-19 | H  | F  | O  | H  | $CH_2Br$ |
| 8-20 | H  | Cl | O  | H  | $CH_2Br$ |
| 8-21 | F  | F  | O  | H  | $CH_2Br$ |
| 8-22 | F  | Cl | O  | H  | $CH_2Br$ |
| 8-23 | Cl | F  | O  | H  | $CH_2Br$ |
| 8-24 | Cl | Cl | O  | H  | $CH_2Br$ |
| 8-25 | H  | F  | O  | H  | $CHBr_2$ |

TABLE 25

|      | X  | Y  | $Z^2$ | $R^1$ | $R^6$ |
|------|----|----|----|----|------|
| 8-26 | H  | Cl | O  | H  | $CHBr_2$ |
| 8-27 | F  | F  | O  | H  | $CHBr_2$ |
| 8-28 | F  | Cl | O  | H  | $CHBr_2$ |
| 8-29 | Cl | F  | O  | H  | $CHBr_2$ |
| 8-30 | Cl | Cl | O  | H  | $CHBr_2$ |
| 8-31 | H  | F  | O  | H  | $CBr_3$ |
| 8-32 | H  | Cl | O  | H  | $CBr_3$ |
| 8-33 | F  | F  | O  | H  | $CBr_3$ |
| 8-34 | F  | Cl | O  | H  | $CBr_3$ |
| 8-35 | Cl | F  | O  | H  | $CBr_3$ |
| 8-36 | Cl | Cl | O  | H  | $CBr_3$ |
| 8-37 | H  | F  | O  | H  | CHO |
| 8-38 | H  | Cl | O  | H  | CHO |
| 8-39 | F  | F  | O  | H  | CHO |
| 8-40 | F  | Cl | O  | H  | CHO |
| 8-41 | Cl | F  | O  | H  | CHO |
| 8-42 | Cl | Cl | O  | H  | CHO |
| 8-43 | H  | F  | O  | H  | CN |
| 8-44 | H  | Cl | O  | H  | CN |
| 8-45 | F  | F  | O  | H  | CN |
| 8-46 | F  | Cl | O  | H  | CN |
| 8-47 | Cl | F  | O  | H  | CN |
| 8-48 | Cl | Cl | O  | H  | CN |
| 8-49 | H  | F  | O  | H  | $CH_2OH$ |
| 8-50 | H  | Cl | O  | H  | $CH_2OH$ |

TABLE 26

|      | X  | Y  | $Z^2$ | $R^1$ | $R^6$ |
|------|----|----|----|----|------|
| 8-51 | F  | F  | O  | H  | $CH_2OH$ |
| 8-52 | F  | Cl | O  | H  | $CH_2OH$ |
| 8-53 | Cl | F  | O  | H  | $CH_2OH$ |
| 8-54 | Cl | Cl | O  | H  | $CH_2OH$ |
| 8-55 | H  | F  | O  | H  | $CH_2OCH_3$ |
| 8-56 | H  | Cl | O  | H  | $CH_2OCH_3$ |
| 8-57 | F  | F  | O  | H  | $CH_2OCH_3$ |
| 8-58 | F  | Cl | O  | H  | $CH_2OCH_3$ |
| 8-59 | Cl | F  | O  | H  | $CH_2OCH_3$ |
| 8-60 | Cl | Cl | O  | H  | $CH_2OCH_3$ |
| 8-61 | H  | F  | O  | H  | $CH_2OC_2H_5$ |
| 8-62 | H  | Cl | O  | H  | $CH_2OC_2H_5$ |

TABLE 26-continued

|      | X  | Y  | $Z^2$ | $R^1$ | $R^6$ |
|------|----|----|----|----|------|
| 8-63 | F  | F  | O  | H  | $CH_2OC_2H_5$ |
| 8-64 | F  | Cl | O  | H  | $CH_2OC_2H_5$ |
| 8-65 | Cl | F  | O  | H  | $CH_2OC_2H_5$ |
| 8-66 | Cl | Cl | O  | H  | $CH_2OC_2H_5$ |
| 8-67 | H  | F  | O  | H  | $CH_2OiC_3H_7$ |
| 8-68 | H  | Cl | O  | H  | $CH_2OiC_3H_7$ |
| 8-69 | F  | F  | O  | H  | $CH_2OiC_3H_7$ |
| 8-70 | F  | Cl | O  | H  | $CH_2OiC_3H_7$ |
| 8-71 | Cl | F  | O  | H  | $CH_2OiC_3H_7$ |
| 8-72 | Cl | Cl | O  | H  | $CH_2OiC_3H_7$ |
| 8-73 | H  | F  | O  | H  | $CH_2OCH_2OCH_3$ |
| 8-74 | H  | Cl | O  | H  | $CH_2OCH_2OCH_3$ |
| 8-75 | F  | F  | O  | H  | $CH_2OCH_2OCH_3$ |

TABLE 27

|       | X  | Y  | $Z^2$ | $R^1$ | $R^6$ |
|-------|----|----|----|----|------|
| 8-76  | F  | Cl | O  | H  | $CH_2OCH_2OCH_3$ |
| 8-77  | Cl | F  | O  | H  | $CH_2OCH_2OCH_3$ |
| 8-78  | Cl | Cl | O  | H  | $CH_2OCH_2OCH_3$ |
| 8-79  | H  | F  | O  | H  | $CH_2OCH_2OC_2H_5$ |
| 8-80  | H  | Cl | O  | H  | $CH_2OCH_2OC_2H_5$ |
| 8-81  | F  | F  | O  | H  | $CH_2OCH_2OC_2H_5$ |
| 8-82  | F  | Cl | O  | H  | $CH_2OCH_2OC_2H_5$ |
| 8-83  | Cl | F  | O  | H  | $CH_2OCH_2OC_2H_5$ |
| 8-84  | Cl | Cl | O  | H  | $CH_2OCH_2OC_2H_5$ |
| 8-85  | H  | F  | O  | H  | $CH_2OCOCH_3$ |
| 8-86  | H  | Cl | O  | H  | $CH_2OCOCH_3$ |
| 8-87  | F  | F  | O  | H  | $CH_2OCOCH_3$ |
| 8-88  | F  | Cl | O  | H  | $CH_2OCOCH_3$ |
| 8-89  | Cl | F  | O  | H  | $CH_2OCOCH_3$ |
| 8-90  | Cl | Cl | O  | H  | $CH_2OCOCH_3$ |
| 8-91  | H  | F  | O  | H  | $CH_2OCOC_2H_5$ |
| 8-92  | H  | Cl | O  | H  | $CH_2OCOC_2H_5$ |
| 8-93  | F  | F  | O  | H  | $CH_2OCOC_2H_5$ |
| 8-94  | F  | Cl | O  | H  | $CH_2OCOC_2H_5$ |
| 8-95  | Cl | F  | O  | H  | $CH_2OCOC_2H_5$ |
| 8-96  | Cl | Cl | O  | H  | $CH_2OCOC_2H_5$ |
| 8-97  | H  | F  | O  | H  | $CH_2OCOiC_3H_7$ |
| 8-98  | H  | Cl | O  | H  | $CH_2OCOiC_3H_7$ |
| 8-99  | F  | F  | O  | H  | $CH_2OCOiC_3H_7$ |
| 8-100 | F  | Cl | O  | H  | $CH_2OCOiC_3H_7$ |

TABLE 28

|       | X  | Y  | $Z^2$ | $R^1$ | $R^6$ |
|-------|----|----|----|----|------|
| 8-101 | Cl | F  | O  | H  | $CH_2OCOiC_3H_7$ |
| 8-102 | Cl | Cl | O  | H  | $CH_2OCOiC_3H_7$ |
| 8-103 | H  | F  | O  | H  | $CH_2OCOCH_2Cl$ |
| 8-104 | H  | Cl | O  | H  | $CH_2OCOCH_2Cl$ |
| 8-105 | F  | F  | O  | H  | $CH_2OCOCH_2Cl$ |
| 8-106 | F  | Cl | O  | H  | $CH_2OCOCH_2Cl$ |
| 8-107 | Cl | F  | O  | H  | $CH_2OCOCH_2Cl$ |
| 8-108 | Cl | Cl | O  | H  | $CH_2OCOCH_2Cl$ |
| 8-109 | H  | F  | O  | H  | $CH_2OCOCCl_3$ |
| 8-110 | H  | Cl | O  | H  | $CH_2OCOCCl_3$ |
| 8-111 | F  | F  | O  | H  | $CH_2OCOCCl_3$ |
| 8-112 | F  | Cl | O  | H  | $CH_2OCOCCl_3$ |
| 8-113 | Cl | F  | O  | H  | $CH_2OCOCCl_3$ |
| 8-114 | Cl | Cl | O  | H  | $CH_2OCOCCl_3$ |
| 8-115 | H  | F  | O  | H  | $CH_2OCOCF_3$ |
| 8-116 | H  | Cl | O  | H  | $CH_2OCOCF_3$ |
| 8-117 | F  | F  | O  | H  | $CH_2OCOCF_3$ |
| 8-118 | F  | Cl | O  | H  | $CH_2OCOCF_3$ |
| 8-119 | Cl | F  | O  | H  | $CH_2OCOCF_3$ |
| 8-120 | Cl | Cl | O  | H  | $CH_2OCOCF_3$ |
| 8-121 | H  | F  | O  | H  | COOH |
| 8-122 | H  | Cl | O  | H  | COOH |
| 8-123 | F  | F  | O  | H  | COOH |

TABLE 28-continued

| | X | Y | $Z^2$ | $R^1$ | $R^6$ |
|---|---|---|---|---|---|
| 8-124 | F | Cl | O | H | COOH |
| 8-125 | Cl | F | O | H | COOH |

TABLE 29

| | X | Y | $Z^2$ | $R^1$ | $R^6$ |
|---|---|---|---|---|---|
| 8-126 | Cl | Cl | O | H | COOH |
| 8-127 | H | F | O | H | $COOCH_3$ |
| 8-128 | H | Cl | O | H | $COOCH_3$ |
| 8-129 | F | F | O | H | $COOCH_3$ |
| 8-130 | F | Cl | O | H | $COOCH_3$ |
| 8-131 | Cl | F | O | H | $COOCH_3$ |
| 8-132 | Cl | Cl | O | H | $COOCH_3$ |
| 8-133 | H | F | O | H | $COOC_2H_5$ |
| 8-134 | H | Cl | O | H | $COOC_2H_5$ |
| 8-135 | F | F | O | H | $COOC_2H_5$ |
| 8-136 | F | Cl | O | H | $COOC_2H_5$ |
| 8-137 | Cl | F | O | H | $COOC_2H_5$ |
| 8-138 | Cl | Cl | O | H | $COOC_2H_5$ |
| 8-139 | H | F | O | H | $COOnC_3H_7$ |
| 8-140 | H | Cl | O | H | $COOnC_3H_7$ |
| 8-141 | F | F | O | H | $COOnC_3H_7$ |
| 8-142 | F | Cl | O | H | $COOnC_3H_7$ |
| 8-143 | Cl | F | O | H | $COOnC_3H_7$ |
| 8-144 | Cl | Cl | O | H | $COOnC_3H_7$ |
| 8-145 | H | F | O | H | $COOnC_4H_9$ |
| 8-146 | H | Cl | O | H | $COOnC_4H_9$ |
| 8-147 | F | F | O | H | $COOnC_4H_9$ |
| 8-148 | F | Cl | O | H | $COOnC_4H_9$ |
| 8-149 | Cl | F | O | H | $COOnC_4H_9$ |
| 8-150 | Cl | Cl | O | H | $COOnC_4H_9$ |

TABLE 30

| | X | Y | $Z^2$ | $R^1$ | $R^6$ |
|---|---|---|---|---|---|
| 8-151 | H | F | O | H | $COOnC_5H_{11}$ |
| 8-152 | H | Cl | O | H | $COOnC_5H_{11}$ |
| 8-153 | F | F | O | H | $COOnC_5H_{11}$ |
| 8-154 | F | Cl | O | H | $COOnC_5H_{11}$ |
| 8-155 | Cl | F | O | H | $COOnC_5H_{11}$ |
| 8-156 | Cl | Cl | O | H | $COOnC_5H_{11}$ |
| 8-157 | H | F | O | H | $COOiC_3H_7$ |
| 8-158 | H | Cl | O | H | $COOiC_3H_7$ |
| 8-159 | F | F | O | H | $COOiC_3H_7$ |
| 8-160 | F | Cl | O | H | $COOiC_3H_7$ |
| 8-161 | Cl | F | O | H | $COOiC_3H_7$ |
| 8-162 | Cl | Cl | O | H | $COOiC_3H_7$ |

Compounds of the general formula:

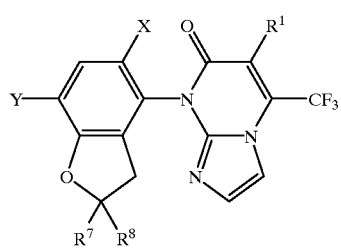

TABLE 31

| | X | Y | $R^1$ | $R^7$ | $R^8$ |
|---|---|---|---|---|---|
| 9-1 | H | F | H | H | $CH_3$ |
| 9-2 | H | Cl | H | H | $CH_3$ |
| 9-3 | H | Br | H | H | $CH_3$ |
| 9-4 | F | F | H | H | $CH_3$ |
| 9-5 | F | Cl | H | H | $CH_3$ |
| 9-6 | F | Br | H | H | $CH_3$ |
| 9-7 | Cl | F | H | H | $CH_3$ |
| 9-8 | Cl | Cl | H | H | $CH_3$ |
| 9-9 | Cl | Br | H | H | $CH_3$ |
| 9-10 | H | F | H | H | $CH_2OH$ |
| 9-11 | H | Cl | H | H | $CH_2OH$ |
| 9-12 | H | Br | H | H | $CH_2OH$ |
| 9-13 | F | F | H | H | $CH_2OH$ |
| 9-14 | F | Cl | H | H | $CH_2OH$ |
| 9-15 | F | Br | H | H | $CH_2OH$ |
| 9-16 | Cl | F | H | H | $CH_2OH$ |
| 9-17 | Cl | Cl | H | H | $CH_2OH$ |
| 9-18 | Cl | Br | H | H | $CH_2OH$ |
| 9-19 | H | F | H | H | $CH_2Cl$ |
| 9-20 | H | Cl | H | H | $CH_2Cl$ |
| 9-21 | F | F | H | H | $CH_2Cl$ |
| 9-22 | F | Cl | H | H | $CH_2Cl$ |
| 9-23 | Cl | F | H | H | $CH_2Cl$ |
| 9-24 | Cl | Cl | H | H | $CH_2Cl$ |
| 9-25 | H | F | H | H | $CH_2Br$ |

TABLE 32

| | X | Y | $R^1$ | $R^7$ | $R^8$ |
|---|---|---|---|---|---|
| 9-26 | H | Cl | H | H | $CH_2Br$ |
| 9-27 | F | F | H | H | $CH_2Br$ |
| 9-28 | F | Cl | H | H | $CH_2Br$ |
| 9-29 | Cl | F | H | H | $CH_2Br$ |
| 9-30 | Cl | Cl | H | H | $CH_2Br$ |
| 9-31 | H | F | H | H | $CH_2OCH_3$ |
| 9-32 | H | Cl | H | H | $CH_2OCH_3$ |
| 9-33 | F | F | H | H | $CH_2OCH_3$ |
| 9-34 | F | Cl | H | H | $CH_2OCH_3$ |
| 9-35 | Cl | F | H | H | $CH_2OCH_3$ |
| 9-36 | Cl | Cl | H | H | $CH_2OCH_3$ |
| 9-37 | H | F | H | H | $CH_2OC_2H_5$ |
| 9-38 | H | Cl | H | H | $CH_2OC_2H_5$ |
| 9-39 | F | F | H | H | $CH_2OC_2H_5$ |
| 9-40 | F | Cl | H | H | $CH_2OC_2H_5$ |
| 9-41 | Cl | F | H | H | $CH_2OC_2H_5$ |
| 9-42 | Cl | Cl | H | H | $CH_2OC_2H_5$ |
| 9-43 | H | F | H | H | $CH_2OiC_3H_7$ |
| 9-44 | H | Cl | H | H | $CH_2OiC_3H_7$ |
| 9-45 | F | F | H | H | $CH_2OiC_3H_7$ |
| 9-46 | F | Cl | H | H | $CH_2OiC_3H_7$ |
| 9-47 | Cl | F | H | H | $CH_2OiC_3H_7$ |
| 9-48 | Cl | Cl | H | H | $CH_2OiC_3H_7$ |
| 9-49 | H | F | H | H | $CH_2OCH_2OCH_3$ |
| 9-50 | H | Cl | H | H | $CH_2OCH_2OCH_3$ |

TABLE 33

| | X | Y | $R^1$ | $R^7$ | $R^8$ |
|---|---|---|---|---|---|
| 9-51 | F | F | H | H | $CH_2OCH_2OCH_3$ |
| 9-52 | F | Cl | H | H | $CH_2OCH_2OCH_3$ |
| 9-53 | Cl | F | H | H | $CH_2OCH_2OCH_3$ |
| 9-54 | Cl | Cl | H | H | $CH_2OCH_2OCH_3$ |
| 9-55 | H | F | H | H | $CH_2OCH_2OC_2H_5$ |
| 9-56 | H | Cl | H | H | $CH_2OCH_2OC_2H_5$ |
| 9-57 | F | F | H | H | $CH_2OCH_2OC_2H_5$ |
| 9-58 | F | Cl | H | H | $CH_2OCH_2OC_2H_5$ |
| 9-59 | Cl | F | H | H | $CH_2OCH_2OC_2H_5$ |
| 9-60 | Cl | Cl | H | H | $CH_2OCH_2OC_2H_5$ |
| 9-61 | H | F | H | H | $CH_2OCOCH_3$ |
| 9-62 | H | Cl | H | H | $CH_2OCOCH_3$ |

TABLE 33-continued

|  | X | Y | R¹ | R⁷ | R⁸ |
|---|---|---|---|---|---|
| 9-63 | F | F | H | H | $CH_2OCOCH_3$ |
| 9-64 | F | Cl | H | H | $CH_2OCOCH_3$ |
| 9-65 | Cl | F | H | H | $CH_2OCOCH_3$ |
| 9-66 | Cl | Cl | H | H | $CH_2OCOCH_3$ |
| 9-67 | H | F | H | H | $CH_2OCOC_2H_5$ |
| 9-68 | H | Cl | H | H | $CH_2OCOC_2H_5$ |
| 9-69 | F | F | H | H | $CH_2OCOC_2H_5$ |
| 9-70 | F | Cl | H | H | $CH_2OCOC_2H_5$ |
| 9-71 | Cl | F | H | H | $CH_2OCOC_2H_5$ |
| 9-72 | Cl | Cl | H | H | $CH_2OCOC_2H_5$ |
| 9-73 | H | F | H | H | $CH_2OCOiC_3H_7$ |
| 9-74 | H | Cl | H | H | $CH_2OCOiC_3H_7$ |
| 9-75 | F | F | H | H | $CH_2OCOiC_3H_7$ |

TABLE 34

|  | X | Y | R¹ | R⁷ | R⁸ |
|---|---|---|---|---|---|
| 9-76 | F | Cl | H | H | $CH_2OCOiC_3H_7$ |
| 9-77 | Cl | F | H | H | $CH_2OCOiC_3H_7$ |
| 9-78 | Cl | Cl | H | H | $CH_2OCOiC_3H_7$ |
| 9-79 | H | F | H | H | $CH_2OCOCH_2Cl$ |
| 9-80 | H | Cl | H | H | $CH_2OCOCH_2Cl$ |
| 9-81 | F | F | H | H | $CH_2OCOCH_2Cl$ |
| 9-82 | F | Cl | H | H | $CH_2OCOCH_2Cl$ |
| 9-83 | Cl | F | H | H | $CH_2OCOCH_2Cl$ |
| 9-84 | Cl | Cl | H | H | $CH_2OCOCH_2Cl$ |
| 9-85 | H | F | H | H | $CH_2OCOCCl_3$ |
| 9-86 | H | Cl | H | H | $CH_2OCOCCl_3$ |
| 9-87 | F | F | H | H | $CH_2OCOCCl_3$ |
| 9-88 | F | Cl | H | H | $CH_2OCOCCl_3$ |
| 9-89 | Cl | F | H | H | $CH_2OCOCCl_3$ |
| 9-90 | Cl | Cl | H | H | $CH_2OCOCCl_3$ |
| 9-91 | H | F | H | H | $CH_2OCOCF_3$ |
| 9-92 | H | Cl | H | H | $CH_2OCOCF_3$ |
| 9-93 | F | F | H | H | $CH_2OCOCF_3$ |
| 9-94 | F | Cl | H | H | $CH_2OCOCF_3$ |
| 9-95 | Cl | F | H | H | $CH_2OCOCF_3$ |
| 9-96 | Cl | Cl | H | H | $CH_2OCOCF_3$ |
| 9-97 | H | F | H | H | COOH |
| 9-98 | H | Cl | H | H | COOH |
| 9-99 | F | F | H | H | COOH |
| 9-100 | F | Cl | H | H | COOH |

TABLE 35

|  | X | Y | R¹ | R⁷ | R⁸ |
|---|---|---|---|---|---|
| 9-101 | Cl | F | H | H | COOH |
| 9-102 | Cl | Cl | H | H | COOH |
| 9-103 | H | F | H | H | $COOCH_3$ |
| 9-104 | H | Cl | H | H | $COOCH_3$ |
| 9-105 | F | F | H | H | $COOCH_3$ |
| 9-106 | F | Cl | H | H | $COOCH_3$ |
| 9-107 | Cl | F | H | H | $COOCH_3$ |
| 9-108 | Cl | Cl | H | H | $COOCH_3$ |
| 9-109 | H | F | H | H | $COOC_2H_5$ |
| 9-110 | H | Cl | H | H | $COOC_2H_5$ |
| 9-111 | F | F | H | H | $COOC_2H_5$ |
| 9-112 | F | Cl | H | H | $COOC_2H_5$ |
| 9-113 | Cl | F | H | H | $COOC_2H_5$ |
| 9-114 | Cl | Cl | H | H | $COOC_2H_5$ |
| 9-115 | H | F | H | H | $COOnC_3H_7$ |
| 9-116 | H | Cl | H | H | $COOnC_3H_7$ |
| 9-117 | F | F | H | H | $COOnC_3H_7$ |
| 9-118 | F | Cl | H | H | $COOnC_3H_7$ |
| 9-119 | Cl | F | H | H | $COOnC_3H_7$ |
| 9-120 | Cl | Cl | H | H | $COOnC_3H_7$ |
| 9-121 | H | F | H | H | $COOnC_4H_9$ |
| 9-122 | H | Cl | H | H | $COOnC_4H_9$ |
| 9-123 | F | F | H | H | $COOnC_4H_9$ |

TABLE 35-continued

|  | X | Y | R¹ | R⁷ | R⁸ |
|---|---|---|---|---|---|
| 9-124 | F | Cl | H | H | $COOnC_4H_9$ |
| 9-125 | Cl | F | H | H | $COOnC_4H_9$ |

TABLE 36

|  | X | Y | R¹ | R⁷ | R⁸ |
|---|---|---|---|---|---|
| 9-126 | Cl | Cl | H | H | $COOnC_4H_9$ |
| 9-127 | H | F | H | H | $COOnC_5H_{11}$ |
| 9-128 | H | Cl | H | H | $COOnC_5H_{11}$ |
| 9-129 | F | F | H | H | $COOnC_5H_{11}$ |
| 9-130 | F | Cl | H | H | $COOnC_5H_{11}$ |
| 9-131 | Cl | F | H | H | $COOnC_5H_{11}$ |
| 9-132 | Cl | Cl | H | H | $COOnC_5H_{11}$ |
| 9-133 | H | F | H | H | $COOiC_3H_7$ |
| 9-134 | H | Cl | H | H | $COOiC_3H_7$ |
| 9-135 | F | F | H | H | $COOiC_3H_7$ |
| 9-136 | F | Cl | H | H | $COOiC_3H_7$ |
| 9-137 | Cl | F | H | H | $COOiC_3H_7$ |
| 9-138 | Cl | Cl | H | H | $COOiC_3H_7$ |
| 9-139 | H | F | H | H | $COOcC_5H_9$ |
| 9-140 | H | Cl | H | H | $COOcC_5H_9$ |
| 9-141 | F | F | H | H | $COOcC_5H_9$ |
| 9-142 | F | Cl | H | H | $COOcC_5H_9$ |
| 9-143 | Cl | F | H | H | $COOcC_5H_9$ |
| 9-144 | Cl | Cl | H | H | $COOcC_5H_9$ |
| 9-145 | H | F | H | H | $COOcC_6H_{11}$ |
| 9-146 | H | Cl | H | H | $COOcC_6H_{11}$ |
| 9-147 | F | F | H | H | $COOcC_6H_{11}$ |
| 9-148 | F | Cl | H | H | $COOcC_6H_{11}$ |
| 9-149 | Cl | F | H | H | $COOcC_6H_{11}$ |
| 9-150 | Cl | Cl | H | H | $COOcC_6H_{11}$ |

TABLE 37

|  | X | Y | R¹ | R⁷ | R⁸ |
|---|---|---|---|---|---|
| 9-151 | H | F | H | H | $COOCH_2CH=CH_2$ |
| 9-152 | H | Cl | H | H | $COOCH_2CH=CH_2$ |
| 9-153 | F | F | H. | H | $COOCH_2CH=CH_2$ |
| 9-154 | F | Cl | H | H | $COOCH_2CH=CH_2$ |
| 9-155 | Cl | F | H | H | $COOCH_2CH=CH_2$ |
| 9-156 | Cl | Cl | H | H | $COOCH_2CH=CH_2$ |
| 9-157 | H | F | H | H | $COOCH_2C\equiv CH$ |
| 9-158 | H | Cl | H | H | $COOCH_2C\equiv CH$ |
| 9-159 | F | F | H | H | $COOCH_2C\equiv CH$ |
| 9-160 | F | Cl | H | H | $COOCH_2C\equiv CH$ |
| 9-161 | Cl | F | H | H | $COOCH_2C\equiv CH$ |
| 9-162 | Cl | Cl | H | H | $COOCH_2C\equiv CH$ |
| 9-163 | H | F | H | H | $CONH_2$ |
| 9-164 | H | Cl | H | H | $CONH_2$ |
| 9-165 | F | F | H | H | $CONH_2$ |
| 9-166 | F | Cl | H | H | $CONH_2$ |
| 9-167 | Cl | F | H | H | $CONH_2$ |
| 9-168 | Cl | Cl | H | H | $CONH_2$ |
| 9-169 | H | F | H | H | $CONHCH_3$ |
| 9-170 | H | Cl | H | H | $CONHCH_3$ |
| 9-171 | F | F | H | H | $CONHCH_3$ |
| 9-172 | F | Cl | H | H | $CONHCH_3$ |
| 9-173 | Cl | F | H | H | $CONHCH_3$ |
| 9-174 | Cl | Cl | H | H | $CONHCH_3$ |
| 9-175 | H | F | H | H | $CONHC_2H_5$ |

TABLE 38

|  | X | Y | R¹ | R⁷ | R⁸ |
|---|---|---|---|---|---|
| 9-176 | H | Cl | H | H | $CONHC_2H_5$ |
| 9-177 | F | F | H | H | $CONHC_2H_5$ |
| 9-178 | F | Cl | H | H | $CONHC_2H_5$ |

TABLE 38-continued

| | X | Y | R$^1$ | R$^7$ | R$^8$ |
|---|---|---|---|---|---|
| 9-179 | Cl | F | H | H | CONHC$_2$H$_5$ |
| 9-180 | Cl | Cl | H | H | CONHC$_2$H$_5$ |
| 9-181 | H | F | H | H | CON(CH$_3$)$_2$ |
| 9-182 | H | Cl | H | H | CON(CH$_3$)$_2$ |
| 9-183 | F | F | H | H | CON(CH$_3$)$_2$ |
| 9-184 | F | Cl | H | H | CON(CH$_3$)$_2$ |
| 9-185 | Cl | F | H | H | CON(CH$_3$)$_2$ |
| 9-186 | Cl | Cl | H | H | CON(CH$_3$)$_2$ |
| 9-187 | H | F | H | H | CON(C$_2$H$_5$)$_2$ |
| 9-188 | H | Cl | H | H | CON(C$_2$H$_5$)$_2$ |
| 9-189 | F | F | H | H | CON(C$_2$H$_5$)$_2$ |
| 9-190 | F | Cl | H | H | CON(C$_2$H$_5$)$_2$ |
| 9-191 | Cl | F | H | H | CON(C$_2$H$_5$)$_2$ |
| 9-192 | Cl | Cl | H | H | CON(C$_2$H$_5$)$_2$ |
| 9-193 | H | F | H | CH$_3$ | CH$_3$ |
| 9-194 | H | Cl | H | CH$_3$ | CH$_3$ |
| 9-195 | H | Br | H | CH$_3$ | CH$_3$ |
| 9-196 | F | F | H | CH$_3$ | CH$_3$ |
| 9-197 | F | Cl | H | CH$_3$ | CH$_3$ |
| 9-198 | F | Br | H | CH$_3$ | CH$_3$ |
| 9-199 | Cl | F | H | CH$_3$ | CH$_3$ |
| 9-200 | Cl | Cl | H | CH$_3$ | CH$_3$ |

TABLE 39

| | X | Y | R$^1$ | R$^7$ | R$^8$ |
|---|---|---|---|---|---|
| 9-201 | Cl | Br | H | CH$_3$ | CH$_3$ |
| 9-202 | H | F | H | CH$_3$ | CH$_2$OH |
| 9-203 | H | Cl | H | CH$_3$ | CH$_2$OH |
| 9-204 | H | Br | H | CH$_3$ | CH$_2$OH |
| 9-205 | F | F | H | CH$_3$ | CH$_2$OH |
| 9-206 | F | Cl | H | CH$_3$ | CH$_2$OH |
| 9-207 | F | Br | H | CH$_3$ | CH$_2$OH |
| 9-208 | Cl | F | H | CH$_3$ | CH$_2$OH |
| 9-209 | Cl | Cl | H | CH$_3$ | CH$_2$OH |
| 9-210 | Cl | Br | H | CH$_3$ | CH$_2$OH |
| 9-211 | H | F | H | CH$_3$ | CH$_2$Cl |
| 9-212 | H | Cl | H | CH$_3$ | CH$_2$Cl |
| 9-213 | F | F | H | CH$_3$ | CH$_2$Cl |
| 9-214 | F | Cl | H | CH$_3$ | CH$_2$Cl |
| 9-215 | Cl | F | H | CH$_3$ | CH$_2$Cl |
| 9-216 | Cl | Cl | H | CH$_3$ | CH$_2$Cl |
| 9-217 | H | F | H | CH$_3$ | CH$_2$Br |
| 9-218 | H | Cl | H | CH$_3$ | CH$_2$Br |
| 9-219 | F | F | H | CH$_3$ | CH$_2$Br |
| 9-220 | F | Cl | H | CH$_3$ | CH$_2$Br |
| 9-221 | Cl | F | H | CH$_3$ | CH$_2$Br |
| 9-222 | Cl | Cl | H | CH$_3$ | CH$_2$Br |
| 9-223 | H | F | H | CH$_3$ | CH$_2$OCH$_3$ |
| 9-224 | H | Cl | H | CH$_3$ | CH$_2$OCH$_3$ |
| 9-225 | F | F | H | CH$_3$ | CH$_2$OCH$_3$ |

TABLE 40

| | X | Y | R$^1$ | R$^7$ | R$^8$ |
|---|---|---|---|---|---|
| 9-226 | F | Cl | H | CH$_3$ | CH$_2$OCH$_3$ |
| 9-227 | Cl | F | H | CH$_3$ | CH$_2$OCH$_3$ |
| 9-228 | Cl | Cl | H | CH$_3$ | CH$_2$OCH$_3$ |
| 9-229 | H | F | H | CH$_3$ | CH$_2$OC$_2$H$_5$ |
| 9-230 | H | Cl | H | CH$_3$ | CH$_2$OC$_2$H$_5$ |
| 9-231 | F | F | H | CH$_3$ | CH$_2$OC$_2$H$_5$ |
| 9-232 | F | Cl | H | CH$_3$ | CH$_2$OC$_2$H$_5$ |
| 9-233 | Cl | F | H | CH$_3$ | CH$_2$OC$_2$H$_5$ |
| 9-234 | Cl | Cl | H | CH$_3$ | CH$_2$OC$_2$H$_5$ |
| 9-235 | H | F | H | CH$_3$ | CH$_2$OiC$_3$H$_7$ |
| 9-236 | H | Cl | H | CH$_3$ | CH$_2$OiC$_3$H$_7$ |
| 9-237 | F | F | H | CH$_3$ | CH$_2$OiC$_3$H$_7$ |
| 9-238 | F | Cl | H | CH$_3$ | CH$_2$OiC$_3$H$_7$ |
| 9-239 | Cl | F | H | CH$_3$ | CH$_2$OiC$_3$H$_7$ |
| 9-240 | Cl | Cl | H | CH$_3$ | CH$_2$OiC$_3$H$_7$ |

TABLE 40-continued

| | X | Y | R$^1$ | R$^7$ | R$^8$ |
|---|---|---|---|---|---|
| 9-241 | H | F | H | CH$_3$ | CH$_2$OCH$_2$OCH$_3$ |
| 9-242 | H | Cl | H | CH$_3$ | CH$_2$OCH$_2$OCH$_3$ |
| 9-243 | F | F | H | CH$_3$ | CH$_2$OCH$_2$OCH$_3$ |
| 9-244 | F | Cl | H | CH$_3$ | CH$_2$OCH$_2$OCH$_3$ |
| 9-245 | Cl | F | H | CH$_3$ | CH$_2$OCH$_2$OCH$_3$ |
| 9-246 | Cl | Cl | H | CH$_3$ | CH$_2$OCH$_2$OCH$_3$ |
| 9-247 | H | F | H | CH$_3$ | CH$_2$OCH$_2$OC$_2$H$_5$ |
| 9-248 | H | Cl | H | CH$_3$ | CH$_2$OCH$_2$OC$_2$H$_5$ |
| 9-249 | F | F | H | CH$_3$ | CH$_2$OCH$_2$OC$_2$H$_5$ |
| 9-250 | F | Cl | H | CH$_3$ | CH$_2$OCH$_2$OC$_2$H$_5$ |

TABLE 41

| | X | Y | R$^1$ | R$^7$ | R$^8$ |
|---|---|---|---|---|---|
| 9-251 | Cl | F | H | CH$_3$ | CH$_2$OCH$_2$OC$_2$H$_5$ |
| 9-252 | Cl | Cl | H | CH$_3$ | CH$_2$OCH$_2$OC$_2$H$_5$ |
| 9-253 | H | F | H | CH$_3$ | CH$_2$OCOCH$_3$ |
| 9-254 | H | Cl | H | CH$_3$ | CH$_2$OCOCH$_3$ |
| 9-255 | F | F | H | CH$_3$ | CH$_2$OCOCH$_3$ |
| 9-256 | F | Cl | H | CH$_3$ | CH$_2$OCOCH$_3$ |
| 9-257 | Cl | F | H | CH$_3$ | CH$_2$OCOCH$_3$ |
| 9-258 | Cl | Cl | H | CH$_3$ | CH$_2$OCOCH$_3$ |
| 9-259 | H | F | H | CH$_3$ | CH$_2$OCOC$_2$H$_5$ |
| 9-260 | H | Cl | H | CH$_3$ | CH$_2$OCOC$_2$H$_5$ |
| 9-261 | F | F | H | CH$_3$ | CH$_2$OCOC$_2$H$_5$ |
| 9-262 | F | Cl | H | CH$_3$ | CH$_2$OCOC$_2$H$_5$ |
| 9-263 | Cl | F | H | CH$_3$ | CH$_2$OCOC$_2$H$_5$ |
| 9-264 | Cl | Cl | H | CH$_3$ | CH$_2$OCOC$_2$H$_5$ |
| 9-265 | H | F | H | CH$_3$ | CH$_2$OCOiC$_3$H$_7$ |
| 9-266 | H | Cl | H | CH$_3$ | CH$_2$OCOiC$_3$H$_7$ |
| 9-267 | F | F | H | CH$_3$ | CH$_2$OCOiC$_3$H$_7$ |
| 9-268 | F | Cl | H | CH$_3$ | CH$_2$OCOiC$_3$H$_7$ |
| 9-269 | Cl | F | H | CH$_3$ | CH$_2$OCOiC$_3$H$_7$ |
| 9-270 | Cl | Cl | H | CH$_3$ | CH$_2$OCOiC$_3$H$_7$ |
| 9-271 | H | F | H | CH$_3$ | CH$_2$OCOCH$_2$Cl |
| 9-272 | H | Cl | H | CH$_3$ | CH$_2$OCOCH$_2$Cl |
| 9-273 | F | F | H | CH$_3$ | CH$_2$OCOCH$_2$Cl |
| 9-274 | F | Cl | H | CH$_3$ | CH$_2$OCOCH$_2$Cl |
| 9-275 | Cl | F | H | CH$_3$ | CH$_2$OCOCH$_2$Cl |

TABLE 42

| | X | Y | R$^1$ | R$^7$ | R$^8$ |
|---|---|---|---|---|---|
| 9-276 | Cl | Cl | H | CH$_3$ | CH$_2$OCOCH$_2$Cl |
| 9-277 | H | F | H | CH$_3$ | CH$_2$OCOCCl$_3$ |
| 9-278 | H | Cl | H | CH$_3$ | CH$_2$OCOCCl$_3$ |
| 9-279 | F | F | H | CH$_3$ | CH$_2$OCOCCl$_3$ |
| 9-280 | F | Cl | H | CH$_3$ | CH$_2$OCOCCl$_3$ |
| 9-281 | Cl | F | H | CH$_3$ | CH$_2$OCOCCl$_3$ |
| 9-282 | Cl | Cl | H | CH$_3$ | CH$_2$OCOCCl$_3$ |
| 9-283 | H | F | H | CH$_3$ | CH$_2$OCOCF$_3$ |
| 9-284 | H | Cl | H | CH$_3$ | CH$_2$OCOCF$_3$ |
| 9-285 | F | F | H | CH$_3$ | CH$_2$OCOCF$_3$ |
| 9-286 | F | Cl | H | CH$_3$ | CH$_2$OCOCF$_3$ |
| 9-287 | Cl | F | H | CH$_3$ | CH$_2$OCOCF$_3$ |
| 9-288 | Cl | Cl | H | CH$_3$ | CH$_2$OCOCF$_3$ |
| 9-289 | H | F | H | CH$_3$ | COOH |
| 9-290 | H | Cl | H | CH$_3$ | COOH |
| 9-291 | F | F | H | CH$_3$ | COOH |
| 9-292 | F | Cl | H | CH$_3$ | COOH |
| 9-293 | Cl | F | H | CH$_3$ | COOH |
| 9-294 | Cl | Cl | H | CH$_3$ | COOH |
| 9-295 | H | F | H | CH$_3$ | COOCH$_3$ |
| 9-296 | H | Cl | H | CH$_3$ | COOCH$_3$ |
| 9-297 | F | F | H | CH$_3$ | COOCH$_3$ |
| 9-298 | F | Cl | H | CH$_3$ | COOCH$_3$ |
| 9-299 | Cl | F | H | CH$_3$ | COOCH$_3$ |
| 9-300 | Cl | Cl | H | CH$_3$ | COOCH$_3$ |

TABLE 43

| | X | Y | R¹ | R⁷ | R⁸ |
|---|---|---|---|---|---|
| 9-301 | H | F | H | $CH_3$ | $COOC_2H_5$ |
| 9-302 | H | Cl | H | $CH_3$ | $COOC_2H_5$ |
| 9-303 | F | F | H | $CH_3$ | $COOC_2H_5$ |
| 9-304 | F | Cl | H | $CH_3$ | $COOC_2H_5$ |
| 9-305 | Cl | F | H | $CH_3$ | $COOC_2H_5$ |
| 9-306 | Cl | Cl | H | $CH_3$ | $COOC_2H_5$ |
| 9-307 | H | F | H | $CH_3$ | $COOnC_3H_7$ |
| 9-308 | H | Cl | H | $CH_3$ | $COOnC_3H_7$ |
| 9-309 | F | F | H | $CH_3$ | $COOnC_3H_7$ |
| 9-310 | F | Cl | H | $CH_3$ | $COOnC_3H_7$ |
| 9-311 | Cl | F | H | $CH_3$ | $COOnC_3H_7$ |
| 9-312 | Cl | Cl | H | $CH_3$ | $COOnC_3H_7$ |
| 9-313 | H | F | H | $CH_3$ | $COOnC_4H_9$ |
| 9-314 | H | Cl | H | $CH_3$ | $COOnC_4H_9$ |
| 9-315 | F | F | H | $CH_3$ | $COOnC_4H_9$ |
| 9-316 | F | Cl | H | $CH_3$ | $COOnC_4H_9$ |
| 9-317 | Cl | F | H | $CH_3$ | $COOnC_4H_9$ |
| 9-318 | Cl | Cl | H | $CH_3$ | $COOnC_4H_9$ |
| 9-319 | H | F | H | $CH_3$ | $COOnC_5H_{11}$ |
| 9-320 | H | Cl | H | $CH_3$ | $COOnC_5H_{11}$ |
| 9-321 | F | F | H | $CH_3$ | $COOnC_5H_{11}$ |
| 9-322 | F | Cl | H | $CH_3$ | $COOnC_5H_{11}$ |
| 9-323 | Cl | F | H | $CH_3$ | $COOnC_5H_{11}$ |
| 9-324 | Cl | Cl | H | $CH_3$ | $COOnC_5H_{11}$ |
| 9-325 | H | F | H | $CH_3$ | $COOiC_3H_7$ |

TABLE 44

| | X | Y | R¹ | R⁷ | R⁸ |
|---|---|---|---|---|---|
| 9-326 | H | Cl | H | $CH_3$ | $COOiC_3H_7$ |
| 9-327 | F | F | H | $CH_3$ | $COOiC_3H_7$ |
| 9-328 | F | Cl | H | $CH_3$ | $COOiC_3H_7$ |
| 9-329 | Cl | F | H | $CH_3$ | $COOiC_3H_7$ |
| 9-330 | Cl | Cl | H | $CH_3$ | $COOiC_3H_7$ |
| 9-331 | H | F | H | $CH_3$ | $COOcC_5H_9$ |
| 9-332 | H | Cl | H | $CH_3$ | $COOcC_5H_9$ |
| 9-333 | F | F | H | $CH_3$ | $COOcC_5H_9$ |
| 9-334 | F | Cl | H | $CH_3$ | $COOcC_5H_9$ |
| 9-335 | Cl | F | H | $CH_3$ | $COOcC_5H_9$ |
| 9-336 | Cl | Cl | H | $CH_3$ | $COOcC_5H_9$ |
| 9-337 | H | F | H | $CH_3$ | $COOcC_6H_{11}$ |
| 9-338 | H | Cl | H | $CH_3$ | $COOcC_6H_{11}$ |
| 9-339 | F | F | H | $CH_3$ | $COOcC_6H_{11}$ |
| 9-340 | F | Cl | H | $CH_3$ | $COOcC_6H_{11}$ |
| 9-341 | Cl | F | H | $CH_3$ | $COOcC_6H_{11}$ |
| 9-342 | Cl | Cl | H | $CH_3$ | $COOcC_6H_{11}$ |
| 9-343 | H | F | H | $CH_3$ | $COOCH_2CH=CH_2$ |
| 9-344 | H | Cl | H | $CH_3$ | $COOCH_2CH=CH_2$ |
| 9-345 | F | F | H | $CH_3$ | $COOCH_2CH=CH_2$ |
| 9-346 | F | Cl | H | $CH_3$ | $COOCH_2CH=CH_2$ |
| 9-347 | Cl | F | H | $CH_3$ | $COOCH_2CH=CH_2$ |
| 9-348 | Cl | Cl | H | $CH_3$ | $COOCH_2CH=CH_2$ |
| 9-349 | H | F | H | $CH_3$ | $COOCH_2C\equiv CH$ |
| 9-350 | H | Cl | H | $CH_3$ | $COOCH_2C\equiv CH$ |

TABLE 45

| | X | Y | R¹ | R⁷ | R⁸ |
|---|---|---|---|---|---|
| 9-351 | F | F | H | $CH_3$ | $COOCH_2C\equiv CH$ |
| 9-352 | F | Cl | H | $CH_3$ | $COOCH_2C\equiv CH$ |
| 9-353 | Cl | F | H | $CH_3$ | $COOCH_2C\equiv CH$ |
| 9-354 | Cl | Cl | H | $CH_3$ | $COOCH_2C\equiv CH$ |
| 9-355 | H | F | H | $CH_3$ | $CONH_2$ |
| 9-356 | H | Cl | H | $CH_3$ | $CONH_2$ |
| 9-357 | F | F | H | $CH_3$ | $CONH_2$ |
| 9-358 | F | Cl | H | $CH_3$ | $CONH_2$ |
| 9-359 | Cl | F | H | $CH_3$ | $CONH_2$ |
| 9-360 | Cl | Cl | H | $CH_3$ | $CONH_2$ |
| 9-361 | H | F | H | $CH_3$ | $CONHCH_3$ |
| 9-362 | H | Cl | H | $CH_3$ | $CONHCH_3$ |

TABLE 45-continued

| | X | Y | R¹ | R⁷ | R⁸ |
|---|---|---|---|---|---|
| 9-363 | F | F | H | $CH_3$ | $CONHCH_3$ |
| 9-364 | F | Cl | H | $CH_3$ | $CONHCH_3$ |
| 9-365 | Cl | F | H | $CH_3$ | $CONHCH_3$ |
| 9-366 | Cl | Cl | H | $CH_3$ | $CONHCH_3$ |
| 9-367 | H | F | H | $CH_3$ | $CONHC_2H_5$ |
| 9-368 | H | Cl | H | $CH_3$ | $CONHC_2H_5$ |
| 9-369 | F | F | H | $CH_3$ | $CONHC_2H_5$ |
| 9-370 | F | Cl | H | $CH_3$ | $CONHC_2H_5$ |
| 9-371 | Cl | F | H | $CH_3$ | $CONHC_2H_5$ |
| 9-372 | Cl | Cl | H | $CH_3$ | $CONHC_2H_5$ |
| 9-373 | H | F | H | $CH_3$ | $CON(CH_3)_2$ |
| 9-374 | H | Cl | H | $CH_3$ | $CON(CH_3)_2$ |
| 9-375 | F | F | H | $CH_3$ | $CON(CH_3)_2$ |

TABLE 46

| | X | Y | R¹ | R⁷ | R⁸ |
|---|---|---|---|---|---|
| 9-376 | F | Cl | H | $CH_3$ | $CON(CH_3)_2$ |
| 9-377 | Cl | F | H | $CH_3$ | $CON(CH_3)_2$ |
| 9-378 | Cl | Cl | H | $CH_3$ | $CON(CH_3)_2$ |
| 9-379 | H | F | H | $CH_3$ | $CON(C_2H_5)_2$ |
| 9-380 | H | Cl | H | $CH_3$ | $CON(C_2H_5)_2$ |
| 9-381 | F | F | H | $CH_3$ | $CON(C_2H_5)_2$ |
| 9-382 | F | Cl | H | $CH_3$ | $CON(C_2H_5)_2$ |
| 9-383 | Cl | F | H | $CH_3$ | $CON(C_2H_5)_2$ |
| 9-384 | Cl | Cl | H | $CH_3$ | $CON(C_2H_5)_2$ |

Compounds of the general formula:

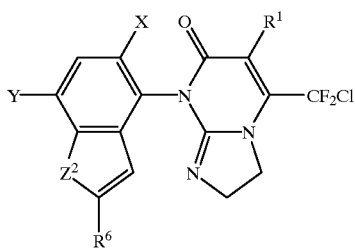

TABLE 47

| | X | Y | Z² | R¹ | R⁶ |
|---|---|---|---|---|---|
| 13-1 | H | F | O | H | $CH_3$ |
| 13-2 | H | Cl | O | H | $CH_3$ |
| 13-3 | H | Br | O | H | $CH_3$ |
| 13-4 | F | F | O | H | $CH_3$ |
| 13-5 | F | Cl | O | H | $CH_3$ |
| 13-6 | F | Br | O | H | $CH_3$ |
| 13-7 | Cl | F | O | H | $CH_3$ |
| 13-8 | Cl | Cl | O | H | $CH_3$ |
| 13-9 | Cl | Br | O | H | $CH_3$ |
| 13-10 | H | F | O | H | $C_2H_5$ |
| 13-11 | H | Cl | O | H | $C_2H_5$ |
| 13-12 | H | Br | O | H | $C_2H_5$ |
| 13-13 | F | F | O | H | $C_2H_5$ |
| 13-14 | F | Cl | O | H | $C_2H_5$ |
| 13-15 | F | Br | O | H | $C_2H_5$ |
| 13-16 | Cl | F | O | H | $C_2H_5$ |
| 13-17 | Cl | Cl | O | H | $C_2H_5$ |
| 13-18 | Cl | Br | O | H | $C_2H_5$ |
| 13-19 | H | F | O | H | $CH_2Br$ |
| 13-20 | H | Cl | O | H | $CH_2Br$ |
| 13-21 | F | F | O | H | $CH_2Br$ |
| 13-22 | F | Cl | O | H | $CH_2Br$ |
| 13-23 | Cl | F | O | H | $CH_2Br$ |

TABLE 47-continued

|  | X | Y | Z² | R¹ | R⁶ |
|---|---|---|---|---|---|
| 13-24 | Cl | Cl | O | H | $CH_2Br$ |
| 13-25 | H | F | O | H | $CHBr_2$ |

TABLE 48

|  | X | Y | Z² | R¹ | R⁶ |
|---|---|---|---|---|---|
| 13-26 | H | Cl | O | H | $CHBr_2$ |
| 13-27 | F | F | O | H | $CHBr_2$ |
| 13-28 | F | Cl | O | H | $CHBr_2$ |
| 13-29 | Cl | F | O | H | $CHBr_2$ |
| 13-30 | Cl | Cl | O | H | $CHBr_2$ |
| 13-31 | H | F | O | H | $CBr_3$ |
| 13-32 | H | Cl | O | H | $CBr_3$ |
| 13-33 | F | F | O | H | $CBr_3$ |
| 13-34 | F | Cl | O | H | $CBr_3$ |
| 13-35 | Cl | F | O | H | $CBr_3$ |
| 13-36 | Cl | Cl | O | H | $CBr_3$ |
| 13-37 | H | F | O | H | CHO |
| 13-38 | H | Cl | O | H | CHO |
| 13-39 | F | F | O | H | CHO |
| 13-40 | F | Cl | O | H | CHO |
| 13-41 | Cl | F | O | H | CHO |
| 13-42 | Cl | Cl | O | H | CHO |
| 13-43 | H | F | O | H | CN |
| 13-44 | H | Cl | O | H | CN |
| 13-45 | F | F | O | H | CN |
| 13-46 | F | Cl | O | H | CN |
| 13-47 | Cl | F | O | H | CN |
| 13-48 | Cl | Cl | O | H | CN |
| 13-49 | H | F | O | H | $CH_2OH$ |
| 13-50 | H | Cl | O | H | $CH_2OH$ |

TABLE 49

|  | X | Y | Z² | R¹ | R⁶ |
|---|---|---|---|---|---|
| 13-51 | F | F | O | H | $CH_2OH$ |
| 13-52 | F | Cl | O | H | $CH_2OH$ |
| 13-53 | Cl | F | O | H | $CH_2OH$ |
| 13-54 | Cl | Cl | O | H | $CH_2OH$ |
| 13-55 | H | F | O | H | $CH_2OCH_3$ |
| 13-56 | H | Cl | O | H | $CH_2OCH_3$ |
| 13-57 | F | F | O | H | $CH_2OCH_3$ |
| 13-58 | F | Cl | O | H | $CH_2OCH_3$ |
| 13-59 | Cl | F | O | H | $CH_2OCH_3$ |
| 13-60 | Cl | Cl | O | H | $CH_2OCH_3$ |
| 13-61 | H | F | O | H | $CH_2OC_2H_5$ |
| 13-62 | H | Cl | O | H | $CH_2OC_2H_5$ |
| 13-63 | F | F | O | H | $CH_2OC_2H_5$ |
| 13-64 | F | Cl | O | H | $CH_2OC_2H_5$ |
| 13-65 | Cl | F | O | H | $CH_2OC_2H_5$ |
| 13-66 | Cl | Cl | O | H | $CH_2OC_2H_5$ |
| 13-67 | H | F | O | H | $CH_2OiC_3H_7$ |
| 13-68 | H | Cl | O | H | $CH_2OiC_3H_7$ |
| 13-69 | F | F | O | H | $CH_2OiC_3H_7$ |
| 13-70 | F | Cl | O | H | $CH_2OiC_3H_7$ |
| 13-71 | Cl | F | O | H | $CH_2OiC_3H_7$ |
| 13-72 | Cl | Cl | O | H | $CH_2OiC_3H_7$ |
| 13-73 | H | F | O | H | $CH_2OCH_2OCH_3$ |
| 13-74 | H | Cl | O | H | $CH_2OCH_2OCH_3$ |
| 13-75 | F | F | O | H | $CH_2OCH_2OCH_3$ |

TABLE 50

|  | X | Y | Z² | R¹ | R⁶ |
|---|---|---|---|---|---|
| 13-76 | F | Cl | O | H | $CH_2OCH_2OCH_3$ |
| 13-77 | Cl | F | O | H | $CH_2OCH_2OCH_3$ |
| 13-78 | Cl | Cl | O | H | $CH_2OCH_2OCH_3$ |

TABLE 50-continued

|  | X | Y | Z² | R¹ | R⁶ |
|---|---|---|---|---|---|
| 13-79 | H | F | O | H | $CH_2OCH_2OC_2H_5$ |
| 13-80 | H | Cl | O | H | $CH_2OCH_2OC_2H_5$ |
| 13-81 | F | F | O | H | $CH_2OCH_2OC_2H_5$ |
| 13-82 | F | Cl | O | H | $CH_2OCH_2OC_2H_5$ |
| 13-83 | Cl | F | O | H | $CH_2OCH_2OC_2H_5$ |
| 13-84 | Cl | Cl | O | H | $CH_2OCH_2OC_2H_5$ |
| 13-85 | H | F | O | H | $CH_2OCOCH_3$ |
| 13-86 | H | Cl | O | H | $CH_2OCOCH_3$ |
| 13-87 | F | F | O | H | $CH_2OCOCH_3$ |
| 13-88 | F | Cl | O | H | $CH_2OCOCH_3$ |
| 13-89 | Cl | F | O | H | $CH_2OCOCH_3$ |
| 13-90 | Cl | Cl | O | H | $CH_2OCOCH_3$ |
| 13-91 | H | F | O | H | $CH_2OCOC_2H_5$ |
| 13-92 | H | Cl | O | H | $CH_2OCOC_2H_5$ |
| 13-93 | F | F | O | H | $CH_2OCOC_2H_5$ |
| 13-94 | F | Cl | O | H | $CH_2OCOC_2H_5$ |
| 13-95 | Cl | F | O | H | $CH_2OCOC_2H_5$ |
| 13-96 | Cl | Cl | O | H | $CH_2OCOC_2H_5$ |
| 13-97 | H | F | O | H | $CH_2OCOiC_3H_7$ |
| 13-98 | H | Cl | O | H | $CH_2OCOiC_3H_7$ |
| 13-99 | F | F | O | H | $CH_2OCOiC_3H_7$ |
| 13-100 | F | Cl | O | H | $CH_2OCOiC_3H_7$ |

TABLE 51

|  | X | Y | Z² | R¹ | R⁶ |
|---|---|---|---|---|---|
| 13-101 | Cl | F | O | H | $CH_2OCOiC_3H_7$ |
| 13-102 | Cl | Cl | O | H | $CH_2OCOiC_3H_7$ |
| 13-103 | H | F | O | H | $CH_2OCOCH_2Cl$ |
| 13-104 | H | Cl | O | H | $CH_2OCOCH_2Cl$ |
| 13-105 | F | F | O | H | $CH_2OCOCH_2Cl$ |
| 13-106 | F | Cl | O | H | $CH_2OCOCH_2Cl$ |
| 13-107 | Cl | F | O | H | $CH_2OCOCH_2Cl$ |
| 13-108 | Cl | Cl | O | H | $CH_2OCOCH_2Cl$ |
| 13-109 | H | F | O | H | $CH_2OCOCCl_3$ |
| 13-110 | H | Cl | O | H | $CH_2OCOCCl_3$ |
| 13-111 | F | F | O | H | $CH_2OCOCCl_3$ |
| 13-112 | F | Cl | O | H | $CH_2OCOCCl_3$ |
| 13-113 | Cl | F | O | H | $CH_2OCOCCl_3$ |
| 13-114 | Cl | Cl | O | H | $CH_2OCOCCl_3$ |
| 13-115 | H | F | O | H | $CH_2OCOCF_3$ |
| 13-116 | H | Cl | O | H | $CH_2OCOCF_3$ |
| 13-117 | F | F | O | H | $CH_2OCOCF_3$ |
| 13-118 | F | Cl | O | H | $CH_2OCOCF_3$ |
| 13-119 | Cl | F | O | H | $CH_2OCOCF_3$ |
| 13-120 | Cl | Cl | O | H | $CH_2OCOCF_3$ |
| 13-121 | H | F | O | H | COOH |
| 13-122 | H | Cl | O | H | COOH |
| 13-123 | F | F | O | H | COOH |
| 13-124 | F | Cl | O | H | COOH |
| 13-125 | Cl | F | O | H | COOH |

TABLE 52

|  | X | Y | Z² | R¹ | R⁶ |
|---|---|---|---|---|---|
| 13-126 | Cl | Cl | O | H | COOH |
| 13-127 | H | F | O | H | $COOCH_3$ |
| 13-128 | H | Cl | O | H | $COOCH_3$ |
| 13-129 | F | F | O | H | $COOCH_3$ |
| 13-130 | F | Cl | O | H | $COOCH_3$ |
| 13-131 | Cl | F | O | H | $COOCH_3$ |
| 13-132 | Cl | Cl | O | H | $COOCH_3$ |
| 13-133 | H | F | O | H | $COOC_2H_5$ |
| 13-134 | H | Cl | O | H | $COOC_2H_5$ |
| 13-135 | F | F | O | H | $COOC_2H_5$ |
| 13-136 | F | Cl | O | H | $COOC_2H_5$ |
| 13-137 | Cl | F | O | H | $COOC_2H_5$ |
| 13-138 | Cl | Cl | O | H | $COOC_2H_5$ |
| 13-139 | H | F | O | H | $COOnC_3H_7$ |
| 13-140 | H | Cl | O | H | $COOnC_3H_7$ |

TABLE 52-continued

|  | X | Y | $Z^2$ | $R^1$ | $R^6$ |
|---|---|---|---|---|---|
| 13-141 | F | F | O | H | $COOnC_3H_7$ |
| 13-142 | F | Cl | O | H | $COOnC_3H_7$ |
| 13-143 | Cl | F | O | H | $COOnC_3H_7$ |
| 13-144 | Cl | Cl | O | H | $COOnC_3H_7$ |
| 13-145 | H | F | O | H | $COOnC_4H_9$ |
| 13-146 | H | Cl | O | H | $COOnC_4H_9$ |
| 13-147 | F | F | O | H | $COOnC_4H_9$ |
| 13-148 | F | Cl | O | H | $COOnC_4H_9$ |
| 13-149 | Cl | F | O | H | $COOnC_4H_9$ |
| 13-150 | Cl | Cl | O | H | $COOnC_4H_9$ |

TABLE 53

|  | X | Y | $Z^2$ | $R^1$ | $R^6$ |
|---|---|---|---|---|---|
| 13-151 | H | F | O | H | $COOnC_5H_{11}$ |
| 13-152 | H | Cl | O | H | $COOnC_5H_{11}$ |
| 13-153 | F | F | O | H | $COOnC_5H_{11}$ |
| 13-154 | F | Cl | O | H | $COOnC_5H_{11}$ |
| 13-155 | Cl | F | O | H | $COOnC_5H_{11}$ |
| 13-156 | Cl | Cl | O | H | $COOnC_5H_{11}$ |
| 13-157 | H | F | O | H | $COOiC_3H_7$ |
| 13-158 | H | Cl | O | H | $COOiC_3H_7$ |
| 13-159 | F | F | O | H | $COOiC_3H_7$ |
| 13-160 | F | Cl | O | H | $COOiC_3H_7$ |
| 13-161 | Cl | F | O | H | $COOiC_3H_7$ |
| 13-162 | Cl | Cl | O | H | $COOiC_3H_7$ |

Compounds of the general formula:

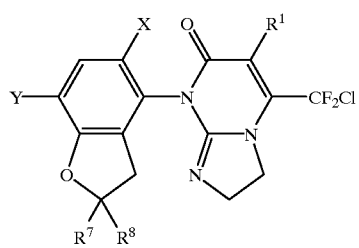

TABLE 54

|  | X | Y | $R^1$ | $R^7$ | $R^8$ |
|---|---|---|---|---|---|
| 14-1 | H | F | H | H | $CH_3$ |
| 14-2 | H | Cl | H | H | $CH_3$ |
| 14-3 | H | Br | H | H | $CH_3$ |
| 14-4 | F | F | H | H | $CH_3$ |
| 14-5 | F | Cl | H | H | $CH_3$ |
| 14-6 | F | Br | H | H | $CH_3$ |
| 14-7 | Cl | F | H | H | $CH_3$ |
| 14-8 | Cl | Cl | H | H | $CH_3$ |
| 14-9 | Cl | Br | H | H | $CH_3$ |
| 14-10 | H | F | H | H | $CH_2OH$ |
| 14-11 | H | Cl | H | H | $CH_2OH$ |
| 14-12 | H | Br | H | H | $CH_2OH$ |
| 14-13 | F | F | H | H | $CH_2OH$ |
| 14-14 | F | Cl | H | H | $CH_2OH$ |
| 14-15 | F | Br | H | H | $CH_2OH$ |
| 14-16 | Cl | F | H | H | $CH_2OH$ |
| 14-17 | Cl | Cl | H | H | $CH_2OH$ |
| 14-18 | Cl | Br | H | H | $CH_2OH$ |
| 14-19 | H | F | H | H | $CH_2Cl$ |
| 14-20 | H | Cl | H | H | $CH_2Cl$ |
| 14-21 | F | F | H | H | $CH_2Cl$ |
| 14-22 | F | Cl | H | H | $CH_2Cl$ |
| 14-23 | Cl | F | H | H | $CH_2Cl$ |

TABLE 54-continued

|  | X | Y | $R^1$ | $R^7$ | $R^8$ |
|---|---|---|---|---|---|
| 14-24 | Cl | Cl | H | H | $CH_2Cl$ |
| 14-25 | H | F | H | H | $CH_2Br$ |

TABLE 55

|  | X | Y | $R^1$ | $R^7$ | $R^8$ |
|---|---|---|---|---|---|
| 14-26 | H | Cl | H | H | $CH_2Br$ |
| 14-27 | F | F | H | H | $CH_2Br$ |
| 14-28 | F | Cl | H | H | $CH_2Br$ |
| 14-29 | Cl | F | H | H | $CH_2Br$ |
| 14-30 | Cl | Cl | H | H | $CH_2Br$ |
| 14-31 | H | F | H | H | $CH_2OCH_3$ |
| 14-32 | H | Cl | H | H | $CH_2OCH_3$ |
| 14-33 | F | F | H | H | $CH_2OCH_3$ |
| 14-34 | F | Cl | H | H | $CH_2OCH_3$ |
| 14-35 | Cl | F | H | H | $CH_2OCH_3$ |
| 14-36 | Cl | Cl | H | H | $CH_2OCH_3$ |
| 14-37 | H | F | H | H | $CH_2OC_2H_5$ |
| 14-38 | H | Cl | H | H | $CH_2OC_2H_5$ |
| 14-39 | F | F | H | H | $CH_2OC_2H_5$ |
| 14-40 | F | Cl | H | H | $CH_2OC_2H_5$ |
| 14-41 | Cl | F | H | H | $CH_2OC_2H_5$ |
| 14-42 | Cl | Cl | H | H | $CH_2OC_2H_5$ |
| 14-43 | H | F | H | H | $CH_2OiC_3H_7$ |
| 14-44 | H | Cl | H | H | $CH_2OiC_3H_7$ |
| 14-45 | F | F | H | H | $CH_2OiC_3H_7$ |
| 14-46 | F | Cl | H | H | $CH_2OiC_3H_7$ |
| 14-47 | Cl | F | H | H | $CH_2OiC_3H_7$ |
| 14-48 | Cl | Cl | H | H | $CH_2OiC_3H_7$ |
| 14-49 | H | F | H | H | $CH_2OCH_2OCH_3$ |
| 14-50 | H | Cl | H | H | $CH_2OCH_2OCH_3$ |

TABLE 56

|  | X | Y | $R^1$ | $R^7$ | $R^8$ |
|---|---|---|---|---|---|
| 14-51 | F | F | H | H | $CH_2OCH_2OCH_3$ |
| 14-52 | F | Cl | H | H | $CH_2OCH_2OCH_3$ |
| 14-53 | Cl | F | H | H | $CH_2OCH_2OCH_3$ |
| 14-54 | Cl | Cl | H | H | $CH_2OCH_2OCH_3$ |
| 14-55 | H | F | H | H | $CH_2OCH_2OC_2H_5$ |
| 14-56 | H | Cl | H | H | $CH_2OCH_2OC_2H_5$ |
| 14-57 | F | F | H | H | $CH_2OCH_2OC_2H_5$ |
| 14-58 | F | Cl | H | H | $CH_2OCH_2OC_2H_5$ |
| 14-59 | Cl | F | H | H | $CH_2OCH_2OC_2H_5$ |
| 14-60 | Cl | Cl | H | H | $CH_2OCH_2OC_2H_5$ |
| 14-61 | H | F | H | H | $CH_2OCOCH_3$ |
| 14-62 | H | Cl | H | H | $CH_2OCOCH_3$ |
| 14-63 | F | F | H | H | $CH_2OCOCH_3$ |
| 14-64 | F | Cl | H | H | $CH_2OCOCH_3$ |
| 14-65 | Cl | F | H | H | $CH_2OCOCH_3$ |
| 14-66 | Cl | Cl | H | H | $CH_2OCOCH_3$ |
| 14-67 | H | F | H | H | $CH_2OCOC_2H_5$ |
| 14-68 | H | Cl | H | H | $CH_2OCOC_2H_5$ |
| 14-69 | F | F | H | H | $CH_2OCOC_2H_5$ |
| 14-70 | F | Cl | H | H | $CH_2OCOC_2H_5$ |
| 14-71 | Cl | F | H | H | $CH_2OCOC_2H_5$ |
| 14-72 | Cl | Cl | H | H | $CH_2OCOC_2H_5$ |
| 14-73 | H | F | H | H | $CH_2OCOiC_3H_7$ |
| 14-74 | H | Cl | H | H | $CH_2OCOiC_3H_7$ |
| 14-75 | F | F | H | H | $CH_2OCOiC_3H_7$ |

TABLE 57

|  | X | Y | $R^1$ | $R^7$ | $R^8$ |
|---|---|---|---|---|---|
| 14-76 | F | Cl | H | H | $CH_2OCOiC_3H_7$ |
| 14-77 | Cl | F | H | H | $CH_2OCOiC_3H_7$ |
| 14-78 | Cl | Cl | H | H | $CH_2OCOiC_3H_7$ |

TABLE 57-continued

| | X | Y | $R^1$ | $R^7$ | $R^8$ |
|---|---|---|---|---|---|
| 14-79 | H | F | H | H | $CH_2OCOCH_2Cl$ |
| 14-80 | H | Cl | H | H | $CH_2OCOCH_2Cl$ |
| 14-81 | F | F | H | H | $CH_2OCOCH_2Cl$ |
| 14-82 | F | Cl | H | H | $CH_2OCOCH_2Cl$ |
| 14-83 | Cl | F | H | H | $CH_2OCOCH_2Cl$ |
| 14-84 | Cl | Cl | H | H | $CH_2OCOCH_2Cl$ |
| 14-85 | H | F | H | H | $CH_2OCOCCl_3$ |
| 14-86 | H | Cl | H | H | $CH_2OCOCCl_3$ |
| 14-87 | F | F | H | H | $CH_2OCOCCl_3$ |
| 14-88 | F | Cl | H | H | $CH_2OCOCCl_3$ |
| 14-89 | Cl | F | H | H | $CH_2OCOCCl_3$ |
| 14-90 | Cl | Cl | H | H | $CH_2OCOCCl_3$ |
| 14-91 | H | F | H | H | $CH_2OCOCF_3$ |
| 14-92 | H | Cl | H | H | $CH_2OCOCF_3$ |
| 14-93 | F | F | H | H | $CH_2OCOCF_3$ |
| 14-94 | F | Cl | H | H | $CH_2OCOCF_3$ |
| 14-95 | Cl | F | H | H | $CH_2OCOCF_3$ |
| 14-96 | Cl | Cl | H | H | $CH_2OCOCF_3$ |
| 14-97 | H | F | H | H | COOH |
| 14-98 | H | Cl | H | H | COOH |
| 14-99 | F | F | H | H | COOH |
| 14-100 | F | Cl | H | H | COOH |

TABLE 58

| | X | Y | $R^1$ | $R^7$ | $R^8$ |
|---|---|---|---|---|---|
| 14-101 | Cl | F | H | H | COOH |
| 14-102 | Cl | Cl | H | H | COOH |
| 14-103 | H | F | H | H | $COOCH_3$ |
| 14-104 | H | Cl | H | H | $COOCH_3$ |
| 14-105 | F | F | H | H | $COOCH_3$ |
| 14-106 | F | Cl | H | H | $COOCH_3$ |
| 14-107 | Cl | F | H | H | $COOCH_3$ |
| 14-108 | Cl | Cl | H | H | $COOCH_3$ |
| 14-109 | H | F | H | H | $COOC_2H_5$ |
| 14-110 | H | Cl | H | H | $COOC_2H_5$ |
| 14-111 | F | F | H | H | $COOC_2H_5$ |
| 14-112 | F | Cl | H | H | $COOC_2H_5$ |
| 14-113 | Cl | F | H | H | $COOC_2H_5$ |
| 14-114 | Cl | Cl | H | H | $COOC_2H_5$ |
| 14-115 | H | F | H | H | $COOnC_3H_7$ |
| 14-116 | H | Cl | H | H | $COOnC_3H_7$ |
| 14-117 | F | F | H | H | $COOnC_3H_7$ |
| 14-118 | F | Cl | H | H | $COOnC_3H_7$ |
| 14-119 | Cl | F | H | H | $COOnC_3H_7$ |
| 14-120 | Cl | Cl | H | H | $COOnC_3H_7$ |
| 14-121 | H | F | H | H | $COOnC_4H_9$ |
| 14-122 | H | Cl | H | H | $COOnC_4H_9$ |
| 14-123 | F | F | H | H | $COOnC_4H_9$ |
| 14-124 | F | Cl | H | H | $COOnC_4H_9$ |
| 14-125 | Cl | F | H | H | $COOnC_4H_9$ |

TABLE 59

| | X | Y | $R^1$ | $R^7$ | $R^8$ |
|---|---|---|---|---|---|
| 14-126 | Cl | Cl | H | H | $COOnC_4H_9$ |
| 14-127 | H | F | H | H | $COOnC_5H_{11}$ |
| 14-128 | H | Cl | H | H | $COOnC_5H_{11}$ |
| 14-129 | F | F | H | H | $COOnC_5H_{11}$ |
| 14-130 | F | Cl | H | H | $COOnC_5H_{11}$ |
| 14-131 | Cl | F | H | H | $COOnC_5H_{11}$ |
| 14-132 | Cl | Cl | H | H | $COOnC_5H_{11}$ |
| 14-133 | H | F | H | H | $COOiC_3H_7$ |
| 14-134 | H | Cl | H | H | $COOiC_3H_7$ |
| 14-135 | F | F | H | H | $COOiC_3H_7$ |
| 14-136 | F | Cl | H | H | $COOiC_3H_7$ |
| 14-137 | Cl | F | H | H | $COOiC_3H_7$ |
| 14-138 | Cl | Cl | H | H | $COOiC_3H_7$ |
| 14-139 | H | F | H | H | $COOcC_5H_9$ |
| 14-140 | H | Cl | H | H | $COOcC_5H_9$ |

TABLE 59-continued

| | X | Y | $R^1$ | $R^7$ | $R^8$ |
|---|---|---|---|---|---|
| 14-141 | F | F | H | H | $COOcC_5H_9$ |
| 14-142 | F | Cl | H | H | $COOcC_5H_9$ |
| 14-143 | Cl | F | H | H | $COOcC_5H_9$ |
| 14-144 | Cl | Cl | H | H | $COOcC_5H_9$ |
| 14-145 | H | F | H | H | $COOcC_6H_{11}$ |
| 14-146 | H | Cl | H | H | $COOcC_6H_{11}$ |
| 14-147 | F | F | H | H | $COOcC_6H_{11}$ |
| 14-148 | F | Cl | H | H | $COOcC_6H_{11}$ |
| 14-149 | Cl | F | H | H | $COOcC_6H_{11}$ |
| 14-150 | Cl | Cl | H | H | $COOcC_6H_{11}$ |

TABLE 60

| | X | Y | $R^1$ | $R^7$ | $R^8$ |
|---|---|---|---|---|---|
| 14-151 | H | F | H | H | $COOCH_2CH=CH_2$ |
| 14-152 | H | Cl | H | H | $COOCH_2CH=CH_2$ |
| 14-153 | F | F | H | H | $COOCH_2CH=CH_2$ |
| 14-154 | F | Cl | H | H | $COOCH_2CH=CH_2$ |
| 14-155 | Cl | F | H | H | $COOCH_2CH=CH_2$ |
| 14-156 | Cl | Cl | H | H | $COOCH_2CH=CH_2$ |
| 14-157 | H | F | H | H | $COOCH_2C\equiv CH$ |
| 14-158 | H | Cl | H | H | $COOCH_2C\equiv CH$ |
| 14-159 | F | F | H | H | $COOCH_2C\equiv CH$ |
| 14-160 | F | Cl | H | H | $COOCH_2C\equiv CH$ |
| 14-161 | Cl | F | H | H | $COOCH_2C\equiv CH$ |
| 14-162 | Cl | Cl | H | H | $COOCH_2C\equiv CH$ |
| 14-163 | H | F | H | H | $CONH_2$ |
| 14-164 | H | Cl | H | H | $CONH_2$ |
| 14-165 | F | F | H | H | $CONH_2$ |
| 14-166 | F | Cl | H | H | $CONH_2$ |
| 14-167 | Cl | F | H | H | $CONH_2$ |
| 14-168 | Cl | Cl | H | H | $CONH_2$ |
| 14-169 | H | F | H | H | $CONHCH_3$ |
| 14-170 | H | Cl | H | H | $CONHCH_3$ |
| 14-171 | F | F | H | H | $CONHCH_3$ |
| 14-172 | F | Cl | H | H | $CONHCH_3$ |
| 14-173 | Cl | F | H | H | $CONHCH_3$ |
| 14-174 | Cl | Cl | H | H | $CONHCH_3$ |
| 14-175 | H | F | H | H | $CONHC_2H_5$ |

TABLE 61

| | X | Y | $R^1$ | $R^7$ | $R^8$ |
|---|---|---|---|---|---|
| 14-176 | H | Cl | H | H | $CONHC_2H_5$ |
| 14-177 | F | F | H | H | $CONHC_2H_5$ |
| 14-178 | F | Cl | H | H | $CONHC_2H_5$ |
| 14-179 | Cl | F | H | H | $CONHC_2H_5$ |
| 14-180 | Cl | Cl | H | H | $CONHC_2H_5$ |
| 14-181 | H | F | H | H | $CON(CH_3)_2$ |
| 14-182 | H | Cl | H | H | $CON(CH_3)_2$ |
| 14-183 | F | F | H | H | $CON(CH_3)_2$ |
| 14-184 | F | Cl | H | H | $CON(CH_3)_2$ |
| 14-185 | Cl | F | H | H | $CON(CH_3)_2$ |
| 14-186 | Cl | Cl | H | H | $CON(CH_3)_2$ |
| 14-187 | H | F | H | H | $CON(C_2H_5)_2$ |
| 14-188 | H | Cl | H | H | $CON(C_2H_5)_2$ |
| 14-189 | F | F | H | H | $CON(C_2H_5)_2$ |
| 14-190 | F | Cl | H | H | $CON(C_2H_5)_2$ |
| 14-191 | Cl | F | H | H | $CON(C_2H_5)_2$ |
| 14-192 | Cl | Cl | H | H | $CON(C_2H_5)_2$ |
| 14-193 | H | F | H | $CH_3$ | $CH_3$ |
| 14-194 | H | Cl | H | $CH_3$ | $CH_3$ |
| 14-195 | H | Br | H | $CH_3$ | $CH_3$ |
| 14-196 | F | F | H | $CH_3$ | $CH_3$ |
| 14-197 | F | Cl | H | $CH_3$ | $CH_3$ |
| 14-198 | F | Br | H | $CH_3$ | $CH_3$ |
| 14-199 | Cl | F | H | $CH_3$ | $CH_3$ |
| 14-200 | Cl | Cl | H | $CH_3$ | $CH_3$ |

TABLE 62

|  | X | Y | R$^1$ | R$^7$ | R$^8$ |
|---|---|---|---|---|---|
| 14-201 | Cl | Br | H | CH$_3$ | CH$_3$ |
| 14-202 | H | F | H | CH$_3$ | CH$_2$OH |
| 14-203 | H | Cl | H | CH$_3$ | CH$_2$OH |
| 14-204 | H | Br | H | CH$_3$ | CH$_2$OH |
| 14-205 | F | F | H | CH$_3$ | CH$_2$OH |
| 14-206 | F | Cl | H | CH$_3$ | CH$_2$OH |
| 14-207 | F | Br | H | CH$_3$ | CH$_2$OH |
| 14-208 | Cl | F | H | CH$_3$ | CH$_2$OH |
| 14-209 | Cl | Cl | H | CH$_3$ | CH$_2$OH |
| 14-210 | Cl | Br | H | CH$_3$ | CH$_2$OH |
| 14-211 | H | F | H | CH$_3$ | CH$_2$Cl |
| 14-212 | H | Cl | H | CH$_3$ | CH$_2$Cl |
| 14-213 | F | F | H | CH$_3$ | CH$_2$Cl |
| 14-214 | F | Cl | H | CH$_3$ | CH$_2$Cl |
| 14-215 | Cl | F | H | CH$_3$ | CH$_2$Cl |
| 14-216 | Cl | Cl | H | CH$_3$ | CH$_2$Cl |
| 14-217 | H | F | H | CH$_3$ | CH$_2$Br |
| 14-218 | H | Cl | H | CH$_3$ | CH$_2$Br |
| 14-219 | F | F | H | CH$_3$ | CH$_2$Br |
| 14-220 | F | Cl | H | CH$_3$ | CH$_2$Br |
| 14-221 | Cl | F | H | CH$_3$ | CH$_2$Br |
| 14-222 | Cl | Cl | H | CH$_3$ | CH$_2$Br |
| 14-223 | H | F | H | CH$_3$ | CH$_2$OCH$_3$ |
| 14-224 | H | Cl | H | CH$_3$ | CH$_2$OCH$_3$ |
| 14-225 | F | F | H | CH$_3$ | CH$_2$OCH$_3$ |

TABLE 63

|  | X | Y | R$^1$ | R$^7$ | R$^8$ |
|---|---|---|---|---|---|
| 14-226 | F | Cl | H | CH$_3$ | CH$_2$OCH$_3$ |
| 14-227 | Cl | F | H | CH$_3$ | CH$_2$OCH$_3$ |
| 14-228 | Cl | Cl | H | CH$_3$ | CH$_2$OCH$_3$ |
| 14-229 | H | F | H | CH$_3$ | CH$_2$OC$_2$H$_5$ |
| 14-230 | H | Cl | H | CH$_3$ | CH$_2$OC$_2$H$_5$ |
| 14-231 | F | F | H | CH$_3$ | CH$_2$OC$_2$H$_5$ |
| 14-232 | F | Cl | H | CH$_3$ | CH$_2$OC$_2$H$_5$ |
| 14-233 | Cl | F | H | CH$_3$ | CH$_2$OC$_2$H$_5$ |
| 14-234 | Cl | Cl | H | CH$_3$ | CH$_2$OC$_2$H$_5$ |
| 14-235 | H | F | H | CH$_3$ | CH$_2$OiC$_3$H$_7$ |
| 14-236 | H | Cl | H | CH$_3$ | CH$_2$OiC$_3$H$_7$ |
| 14-237 | F | F | H | CH$_3$ | CH$_2$OiC$_3$H$_7$ |
| 14-238 | F | Cl | H | CH$_3$ | CH$_2$OiC$_3$H$_7$ |
| 14-239 | Cl | F | H | CH$_3$ | CH$_2$OiC$_3$H$_7$ |
| 14-240 | Cl | Cl | H | CH$_3$ | CH$_2$OiC$_3$H$_7$ |
| 14-241 | H | F | H | CH$_3$ | CH$_2$OCH$_2$OCH$_3$ |
| 14-242 | H | Cl | H | CH$_3$ | CH$_2$OCH$_2$OCH$_3$ |
| 14-243 | F | F | H | CH$_3$ | CH$_2$OCH$_2$OCH$_3$ |
| 14-244 | F | Cl | H | CH$_3$ | CH$_2$OCH$_2$OCH$_3$ |
| 14-245 | Cl | F | H | CH$_3$ | CH$_2$OCH$_2$OCH$_3$ |
| 14-246 | Cl | Cl | H | CH$_3$ | CH$_2$OCH$_2$OCH$_3$ |
| 14-247 | H | F | H | CH$_3$ | CH$_2$OCH$_2$OC$_2$H$_5$ |
| 14-248 | H | Cl | H | CH$_3$ | CH$_2$OCH$_2$OC$_2$H$_5$ |
| 14-249 | F | F | H | CH$_3$ | CH$_2$OCH$_2$OC$_2$H$_5$ |
| 14-250 | F | Cl | H | CH$_3$ | CH$_2$OCH$_2$OC$_2$H$_5$ |

TABLE 64

|  | X | Y | R$^1$ | R$^7$ | R$^8$ |
|---|---|---|---|---|---|
| 14-251 | Cl | F | H | CH$_3$ | CH$_2$OCH$_2$OC$_2$H$_5$ |
| 14-252 | Cl | Cl | H | CH$_3$ | CH$_2$OCH$_2$OC$_2$H$_5$ |
| 14-253 | H | F | H | CH$_3$ | CH$_2$OCOCH$_3$ |
| 14-254 | H | Cl | H | CH$_3$ | CH$_2$OCOCH$_3$ |
| 14-255 | F | F | H | CH$_3$ | CH$_2$OCOCH$_3$ |
| 14-256 | F | Cl | H | CH$_3$ | CH$_2$OCOCH$_3$ |
| 14-257 | Cl | F | H | CH$_3$ | CH$_2$OCOCH$_3$ |
| 14-258 | Cl | Cl | H | CH$_3$ | CH$_2$OCOCH$_3$ |
| 14-259 | H | F | H | CH$_3$ | CH$_2$OCOC$_2$H$_5$ |
| 14-260 | H | Cl | H | CH$_3$ | CH$_2$OCOC$_2$H$_5$ |
| 14-261 | F | F | H | CH$_3$ | CH$_2$OCOC$_2$H$_5$ |
| 14-262 | F | Cl | H | CH$_3$ | CH$_2$OCOC$_2$H$_5$ |

TABLE 64-continued

|  | X | Y | R$^1$ | R$^7$ | R$^8$ |
|---|---|---|---|---|---|
| 14-263 | Cl | F | H | CH$_3$ | CH$_2$OCOC$_2$H$_5$ |
| 14-264 | Cl | Cl | H | CH$_3$ | CH$_2$OCOC$_2$H$_5$ |
| 14-265 | H | F | H | CH$_3$ | CH$_2$OCOiC$_3$H$_7$ |
| 14-266 | H | Cl | H | CH$_3$ | CH$_2$OCOiC$_3$H$_7$ |
| 14-267 | F | F | H | CH$_3$ | CH$_2$OCOiC$_3$H$_7$ |
| 14-268 | F | Cl | H | CH$_3$ | CH$_2$OCOiC$_3$H$_7$ |
| 14-269 | Cl | F | H | CH$_3$ | CH$_2$OCOiC$_3$H$_7$ |
| 14-270 | Cl | Cl | H | CH$_3$ | CH$_2$OCOiC$_3$H$_7$ |
| 14-271 | H | F | H | CH$_3$ | CH$_2$OCOCH$_2$Cl |
| 14-272 | H | Cl | H | CH$_3$ | CH$_2$OCOCH$_2$Cl |
| 14-273 | F | F | H | CH$_3$ | CH$_2$OCOCH$_2$Cl |
| 14-274 | F | Cl | H | CH$_3$ | CH$_2$OCOCH$_2$Cl |
| 14-275 | Cl | F | H | CH$_3$ | CH$_2$OCOCH$_2$Cl |

TABLE 65

|  | X | Y | R$^1$ | R$^7$ | R$^8$ |
|---|---|---|---|---|---|
| 14-276 | Cl | Cl | H | CH$_3$ | CH$_2$OCOCH$_2$Cl |
| 14-277 | H | F | H | CH$_3$ | CH$_2$OCOCCl$_3$ |
| 14-278 | H | Cl | H | CH$_3$ | CH$_2$OCOCCl$_3$ |
| 14-279 | F | F | H | CH$_3$ | CH$_2$OCOCCl$_3$ |
| 14-280 | F | Cl | H | CH$_3$ | CH$_2$OCOCCl$_3$ |
| 14-281 | Cl | F | H | CH$_3$ | CH$_2$OCOCCl$_3$ |
| 14-282 | Cl | Cl | H | CH$_3$ | CH$_2$OCOCCl$_3$ |
| 14-283 | H | F | H | CH$_3$ | CH$_2$OCOCF$_3$ |
| 14-284 | H | Cl | H | CH$_3$ | CH$_2$OCOCF$_3$ |
| 14-285 | F | F | H | CH$_3$ | CH$_2$OCOCF$_3$ |
| 14-286 | F | Cl | H | CH$_3$ | CH$_2$OCOCF$_3$ |
| 14-287 | Cl | F | H | CH$_3$ | CH$_2$OCOCF$_3$ |
| 14-288 | Cl | Cl | H | CH$_3$ | CH$_2$OCOCF$_3$ |
| 14-289 | H | F | H | CH$_3$ | COOH |
| 14-290 | H | Cl | H | CH$_3$ | COOH |
| 14-291 | F | F | H | CH$_3$ | COOH |
| 14-292 | F | Cl | H | CH$_3$ | COOH |
| 14-293 | Cl | F | H | CH$_3$ | COOH |
| 14-294 | Cl | Cl | H | CH$_3$ | COOH |
| 14-295 | H | F | H | CH$_3$ | COOCH$_3$ |
| 14-296 | H | Cl | H | CH$_3$ | COOCH$_3$ |
| 14-297 | F | F | H | CH$_3$ | COOCH$_3$ |
| 14-298 | F | Cl | H | CH$_3$ | COOCH$_3$ |
| 14-299 | Cl | F | H | CH$_3$ | COOCH$_3$ |
| 14-300 | Cl | Cl | H | CH$_3$ | COOCH$_3$ |

TABLE 66

|  | X | Y | R$^1$ | R$^7$ | R$^8$ |
|---|---|---|---|---|---|
| 14-301 | H | F | H | CH$_3$ | COOC$_2$H$_5$ |
| 14-302 | H | Cl | H | CH$_3$ | COOC$_2$H$_5$ |
| 14-303 | F | F | H | CH$_3$ | COOC$_2$H$_5$ |
| 14-304 | F | Cl | H | CH$_3$ | COOC$_2$H$_5$ |
| 14-305 | Cl | F | H | CH$_3$ | COOC$_2$H$_5$ |
| 14-306 | Cl | Cl | H | CH$_3$ | COOC$_2$H$_5$ |
| 14-307 | H | F | H | CH$_3$ | COOnC$_3$H$_7$ |
| 14-308 | H | Cl | H | CH$_3$ | COOnC$_3$H$_7$ |
| 14-309 | F | F | H | CH$_3$ | COOnC$_3$H$_7$ |
| 14-310 | F | Cl | H | CH$_3$ | COOnC$_3$H$_7$ |
| 14-311 | Cl | F | H | CH$_3$ | COOnC$_3$H$_7$ |
| 14-312 | Cl | Cl | H | CH$_3$ | COOnC$_3$H$_7$ |
| 14-313 | H | F | H | CH$_3$ | COOnC$_4$H$_9$ |
| 14-314 | H | Cl | H | CH$_3$ | COOnC$_4$H$_9$ |
| 14-315 | F | F | H | CH$_3$ | COOnC$_4$H$_9$ |
| 14-316 | F | Cl | H | CH$_3$ | COOnC$_4$H$_9$ |
| 14-317 | Cl | F | H | CH$_3$ | COOnC$_4$H$_9$ |
| 14-318 | Cl | Cl | H | CH$_3$ | COOnC$_4$H$_9$ |
| 14-319 | H | F | H | CH$_3$ | COOnC$_5$H$_{11}$ |
| 14-320 | H | Cl | H | CH$_3$ | COOnC$_5$H$_{11}$ |
| 14-321 | F | F | H | CH$_3$ | COOnC$_5$H$_{11}$ |
| 14-322 | F | Cl | H | CH$_3$ | COOnC$_5$H$_{11}$ |
| 14-323 | Cl | F | H | CH$_3$ | COOnC$_5$H$_{11}$ |

TABLE 66-continued

|  | X | Y | R¹ | R⁷ | R⁸ |
| --- | --- | --- | --- | --- | --- |
| 14-324 | Cl | Cl | H | CH₃ | COOnC₅H₁₁ |
| 14-325 | H | F | H | CH₃ | COOiC₃H₇ |

TABLE 67

|  | X | Y | R¹ | R⁷ | R⁸ |
| --- | --- | --- | --- | --- | --- |
| 14-326 | H | Cl | H | CH₃ | COOiC₃H₇ |
| 14-327 | F | F | H | CH₃ | COOiC₃H₇ |
| 14-328 | F | Cl | H | CH₃ | COOiC₃H₇ |
| 14-329 | Cl | F | H | CH₃ | COOiC₃H₇ |
| 14-330 | Cl | Cl | H | CH₃ | COOiC₃H₇ |
| 14-331 | H | F | H | CH₃ | COOcC₅H₉ |
| 14-332 | H | Cl | H | CH₃ | COOcC₅H₉ |
| 14-333 | F | F | H | CH₃ | COOcC₅H₉ |
| 14-334 | F | Cl | H | CH₃ | COOcC₅H₉ |
| 14-335 | Cl | F | H | CH₃ | COOcC₅H₉ |
| 14-336 | Cl | Cl | H | CH₃ | COOcC₅H₉ |
| 14-337 | H | F | H | CH₃ | COOcC₆H₁₁ |
| 14-338 | H | Cl | H | CH₃ | COOcC₆H₁₁ |
| 14-339 | F | F | H | CH₃ | COOcC₆H₁₁ |
| 14-340 | F | Cl | H | CH₃ | COOcC₆H₁₁ |
| 14-341 | Cl | F | H | CH₃ | COOcC₆H₁₁ |
| 14-342 | Cl | Cl | H | CH₃ | COOcC₆H₁₁ |
| 14-343 | H | F | H | CH₃ | COOCH₂CH=CH₂ |
| 14-344 | H | Cl | H | CH₃ | COOCH₂CH=CH₂ |
| 14-345 | F | F | H | CH₃ | COOCH₂CH=CH₂ |
| 14-346 | F | Cl | H | CH₃ | COOCH₂CH=CH₂ |
| 14-347 | Cl | F | H | CH₃ | COOCH₂CH=CH₂ |
| 14-348 | Cl | Cl | H | CH₃ | COOCH₂CH=CH₂ |
| 14-349 | H | F | H | CH₃ | COOCH₂C≡CH |
| 14-350 | H | Cl | H | CH₃ | COOCH₂C≡CH |

TABLE 68

|  | X | Y | R¹ | R⁷ | R⁸ |
| --- | --- | --- | --- | --- | --- |
| 14-351 | F | F | H | CH₃ | COOCH₂C≡CH |
| 14-352 | F | Cl | H | CH₃ | COOCH₂C≡CH |
| 14-353 | Cl | F | H | CH₃ | COOCH₂C≡CH |
| 14-354 | Cl | Cl | H | CH₃ | COOCH₂C≡CH |
| 14-355 | H | F | H | CH₃ | CONH₂ |
| 14-356 | H | Cl | H | CH₃ | CONH₂ |
| 14-357 | F | F | H | CH₃ | CONH₂ |
| 14-358 | F | Cl | H | CH₃ | CONH₂ |
| 14-359 | Cl | F | H | CH₃ | CONH₂ |
| 14-360 | Cl | Cl | H | CH₃ | CONH₂ |
| 14-361 | H | F | H | CH₃ | CONHCH₃ |
| 14-362 | H | Cl | H | CH₃ | CONHCH₃ |
| 14-363 | F | F | H | CH₃ | CONHCH₃ |
| 14-364 | F | Cl | H | CH₃ | CONHCH₃ |
| 14-365 | Cl | F | H | CH₃ | CONHCH₃ |
| 14-366 | Cl | Cl | H | CH₃ | CONHCH₃ |
| 14-367 | H | F | H | CH₃ | CONHC₂H₅ |
| 14-368 | H | Cl | H | CH₃ | CONHC₂H₅ |
| 14-369 | F | F | H | CH₃ | CONHC₂H₅ |
| 14-370 | F | Cl | H | CH₃ | CONHC₂H₅ |
| 14-371 | Cl | F | H | CH₃ | CONHC₂H₅ |
| 14-372 | Cl | Cl | H | CH₃ | CONHC₂H₅ |
| 14-373 | H | F | H | CH₃ | CON(CH₃)₂ |
| 14-374 | H | Cl | H | CH₃ | CON(CH₃)₂ |
| 14-375 | F | F | H | CH₃ | CON(CH₃)₂ |

TABLE 69

|  | X | Y | R¹ | R⁷ | R⁸ |
| --- | --- | --- | --- | --- | --- |
| 14-376 | F | Cl | H | CH₃ | CON(CH₃)₂ |
| 14-377 | Cl | F | H | CH₃ | CON(CH₃)₂ |
| 14-378 | Cl | Cl | H | CH₃ | CON(CH₃)₂ |

TABLE 69-continued

|  | X | Y | R¹ | R⁷ | R⁸ |
| --- | --- | --- | --- | --- | --- |
| 14-379 | H | F | H | CH₃ | CON(C₂H₅)₂ |
| 14-380 | H | Cl | H | CH₃ | CON(C₂H₅)₂ |
| 14-381 | F | F | H | CH₃ | CON(C₂H₅)₂ |
| 14-382 | F | Cl | H | CH₃ | CON(C₂H₅)₂ |
| 14-383 | Cl | F | H | CH₃ | CON(C₂H₅)₂ |
| 14-384 | Cl | Cl | H | CH₃ | CON(C₂H₅)₂ |

Compounds of the general formula:

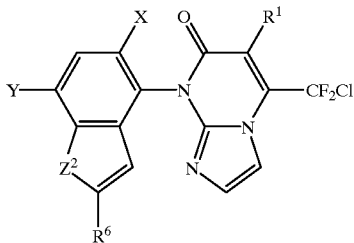

TABLE 70

|  | X | Y | Z² | R¹ | R⁶ |
| --- | --- | --- | --- | --- | --- |
| 18-1 | H | F | O | H | CH₃ |
| 18-2 | H | Cl | O | H | CH₃ |
| 18-3 | H | Br | O | H | CH₃ |
| 18-4 | F | F | O | H | CH₃ |
| 18-5 | F | Cl | O | H | CH₃ |
| 18-6 | F | Br | O | H | CH₃ |
| 18-7 | Cl | F | O | H | CH₃ |
| 18-8 | Cl | Cl | O | H | CH₃ |
| 18-9 | Cl | Br | O | H | CH₃ |
| 18-10 | H | F | O | H | C₂H₅ |
| 18-11 | H | Cl | O | H | C₂H₅ |
| 18-12 | H | Br | O | H | C₂H₅ |
| 18-13 | F | F | O | H | C₂H₅ |
| 18-14 | F | Cl | O | H | C₂H₅ |
| 18-15 | F | Br | O | H | C₂H₅ |
| 18-16 | Cl | F | O | H | C₂H₅ |
| 18-17 | Cl | Cl | O | H | C₂H₅ |
| 18-18 | Cl | Br | O | H | C₂H₅ |
| 18-19 | H | F | O | H | CH₂Br |
| 18-20 | H | Cl | O | H | CH₂Br |
| 18-21 | F | F | O | H | CH₂Br |
| 18-22 | F | Cl | O | H | CH₂Br |
| 18-23 | Cl | F | O | H | CH₂Br |
| 18-24 | Cl | Cl | O | H | CH₂Br |
| 18-25 | H | F | O | H | CHBr₂ |

TABLE 71

|  | X | Y | Z² | R¹ | R⁶ |
| --- | --- | --- | --- | --- | --- |
| 18-26 | H | Cl | O | H | CHBr₂ |
| 18-27 | F | F | O | H | CHBr₂ |
| 18-28 | F | Cl | O | H | CHBr₂ |
| 18-29 | Cl | F | O | H | CHBr₂ |
| 18-30 | Cl | Cl | O | H | CHBr₂ |
| 18-31 | H | F | O | H | CBr₃ |
| 18-32 | H | Cl | O | H | CBr₃ |
| 18-33 | F | F | O | H | CBr₃ |
| 18-34 | F | Cl | O | H | CBr₃ |
| 18-35 | Cl | F | O | H | CBr₃ |
| 18-36 | Cl | Cl | O | H | CBr₃ |
| 18-37 | H | F | O | H | CHO |
| 18-38 | H | Cl | O | H | CHO |
| 18-39 | F | F | O | H | CHO |

TABLE 71-continued

| | X | Y | Z² | R¹ | R⁶ |
|---|---|---|---|---|---|
| 18-40 | F | Cl | O | H | CHO |
| 18-41 | Cl | F | O | H | CHO |
| 18-42 | Cl | Cl | O | H | CHO |
| 18-43 | H | F | O | H | CN |
| 18-44 | H | Cl | O | H | CN |
| 18-45 | F | F | O | H | CN |
| 18-46 | F | Cl | O | H | CN |
| 18-47 | Cl | F | O | H | CN |
| 18-48 | Cl | Cl | O | H | CN |
| 18-49 | H | F | O | H | $CH_2OH$ |
| 18-50 | H | Cl | O | H | $CH_2OH$ |

TABLE 72

| | X | Y | Z² | R¹ | R⁶ |
|---|---|---|---|---|---|
| 18-51 | F | F | O | H | $CH_2OH$ |
| 18-52 | F | Cl | O | H | $CH_2OH$ |
| 18-53 | Cl | F | O | H | $CH_2OH$ |
| 18-54 | Cl | Cl | O | H | $CH_2OH$ |
| 18-55 | H | F | O | H | $CH_2OCH_3$ |
| 18-56 | H | Cl | O | H | $CH_2OCH_3$ |
| 18-57 | F | F | O | H | $CH_2OCH_3$ |
| 18-58 | F | Cl | O | H | $CH_2OCH_3$ |
| 18-59 | Cl | F | O | H | $CH_2OCH_3$ |
| 18-60 | Cl | Cl | O | H | $CH_2OCH_3$ |
| 18-61 | H | F | O | H | $CH_2OC_2H_5$ |
| 18-62 | H | Cl | O | H | $CH_2OC_2H_5$ |
| 18-63 | F | F | O | H | $CH_2OC_2H_5$ |
| 18-64 | F | Cl | O | H | $CH_2OC_2H_5$ |
| 18-65 | Cl | F | O | H | $CH_2OC_2H_5$ |
| 18-66 | Cl | Cl | O | H | $CH_2OC_2H_5$ |
| 18-67 | H | F | O | H | $CH_2OiC_3H_7$ |
| 18-68 | H | Cl | O | H | $CH_2OiC_3H_7$ |
| 18-69 | F | F | O | H | $CH_2OiC_3H_7$ |
| 18-70 | F | Cl | O | H | $CH_2OiC_3H_7$ |
| 18-71 | Cl | F | O | H | $CH_2OiC_3H_7$ |
| 18-72 | Cl | Cl | O | H | $CH_2OiC_3H_7$ |
| 18-73 | H | F | O | H | $CH_2OCH_2OCH_3$ |
| 18-74 | H | Cl | O | H | $CH_2OCH_2OCH_3$ |
| 18-75 | F | F | O | H | $CH_2OCH_2OCH_3$ |

TABLE 73

| | X | Y | Z² | R¹ | R⁶ |
|---|---|---|---|---|---|
| 18-76 | F | Cl | O | H | $CH_2OCH_2OCH_3$ |
| 18-77 | Cl | F | O | H | $CH_2OCH_2OCH_3$ |
| 18-78 | Cl | Cl | O | H | $CH_2OCH_2OCH_3$ |
| 18-79 | H | F | O | H | $CH_2OCH_2OC_2H_5$ |
| 18-80 | H | Cl | O | H | $CH_2OCH_2OC_2H_5$ |
| 18-81 | F | F | O | H | $CH_2OCH_2OC_2H_5$ |
| 18-82 | F | Cl | O | H | $CH_2OCH_2OC_2H_5$ |
| 18-83 | Cl | F | O | H | $CH_2OCH_2OC_2H_5$ |
| 18-84 | Cl | Cl | O | H | $CH_2OCH_2OC_2H_5$ |
| 18-85 | H | F | O | H | $CH_2OCOCH_3$ |
| 18-86 | H | Cl | O | H | $CH_2OCOCH_3$ |
| 18-87 | F | F | O | H | $CH_2OCOCH_3$ |
| 18-88 | F | Cl | O | H | $CH_2OCOCH_3$ |
| 18-89 | Cl | F | O | H | $CH_2OCOCH_3$ |
| 18-90 | Cl | Cl | O | H | $CH_2OCOCH_3$ |
| 18-91 | H | F | O | H | $CH_2OCOC_2H_5$ |
| 18-92 | H | Cl | O | H | $CH_2OCOC_2H_5$ |
| 18-93 | F | F | O | H | $CH_2OCOC_2H_5$ |
| 18-94 | F | Cl | O | H | $CH_2OCOC_2H_5$ |
| 18-95 | Cl | F | O | H | $CH_2OCOC_2H_5$ |
| 18-96 | Cl | Cl | O | H | $CH_2OCOC_2H_5$ |
| 18-97 | H | F | O | H | $CH_2OCOiC_3H_7$ |
| 18-98 | H | Cl | O | H | $CH_2OCOiC_3H_7$ |
| 18-99 | F | F | O | H | $CH_2OCOiC_3H_7$ |
| 18-100 | F | Cl | O | H | $CH_2OCOiC_3H_7$ |

TABLE 74

| | X | Y | Z² | R¹ | R⁶ |
|---|---|---|---|---|---|
| 18-101 | Cl | F | O | H | $CH_2OCOiC_3H_7$ |
| 18-102 | Cl | Cl | O | H | $CH_2OCOiC_3H_7$ |
| 18-103 | H | F | O | H | $CH_2OCOCH_2Cl$ |
| 18-104 | H | Cl | O | H | $CH_2OCOCH_2Cl$ |
| 18-105 | F | F | O | H | $CH_2OCOCH_2Cl$ |
| 18-106 | F | Cl | O | H | $CH_2OCOCH_2Cl$ |
| 18-107 | Cl | F | O | H | $CH_2OCOCH_2Cl$ |
| 18-108 | Cl | Cl | O | H | $CH_2OCOCH_2Cl$ |
| 18-109 | H | F | O | H | $CH_2OCOCCl_3$ |
| 18-110 | H | Cl | O | H | $CH_2OCOCCl_3$ |
| 18-111 | F | F | O | H | $CH_2OCOCCl_3$ |
| 18-112 | F | Cl | O | H | $CH_2OCOCCl_3$ |
| 18-113 | Cl | F | O | H | $CH_2OCOCCl_3$ |
| 18-114 | Cl | Cl | O | H | $CH_2OCOCCl_3$ |
| 18-115 | H | F | O | H | $CH_2OCOCF_3$ |
| 18-116 | H | Cl | O | H | $CH_2OCOCF_3$ |
| 18-117 | F | F | O | H | $CH_2OCOCF_3$ |
| 18-118 | F | Cl | O | H | $CH_2OCOCF_3$ |
| 18-119 | Cl | F | O | H | $CH_2OCOCF_3$ |
| 18-120 | Cl | Cl | O | H | $CH_2OCOCF_3$ |
| 18-121 | H | F | O | H | COOH |
| 18-122 | H | Cl | O | H | COOH |
| 18-123 | F | F | O | H | COOH |
| 18-124 | F | Cl | O | H | COOH |
| 18-125 | Cl | F | O | H | COOH |

TABLE 75

| | X | Y | Z² | R¹ | R⁶ |
|---|---|---|---|---|---|
| 18-126 | Cl | Cl | O | H | COOH |
| 18-127 | H | F | O | H | $COOCH_3$ |
| 18-128 | H | Cl | O | H | $COOCH_3$ |
| 18-129 | F | F | O | H | $COOCH_3$ |
| 18-130 | F | Cl | O | H | $COOCH_3$ |
| 18-131 | Cl | F | O | H | $COOCH_3$ |
| 18-132 | Cl | Cl | O | H | $COOCH_3$ |
| 18-133 | H | F | O | H | $COOC_2H_5$ |
| 18-134 | H | Cl | O | H | $COOC_2H_5$ |
| 18-135 | F | F | O | H | $COOC_2H_5$ |
| 18-136 | F | Cl | O | H | $COOC_2H_5$ |
| 18-137 | Cl | F | O | H | $COOC_2H_5$ |
| 18-138 | Cl | Cl | O | H | $COOC_2H_5$ |
| 18-139 | H | F | O | H | $COOnC_3H_7$ |
| 18-140 | H | Cl | O | H | $COOnC_3H_7$ |
| 18-141 | F | F | O | H | $COOnC_3H_7$ |
| 18-142 | F | Cl | O | H | $COOnC_3H_7$ |
| 18-143 | Cl | F | O | H | $COOnC_3H_7$ |
| 18-144 | Cl | Cl | O | H | $COOnC_3H_7$ |
| 18-145 | H | F | O | H | $COOnC_4H_9$ |
| 18-146 | H | Cl | O | H | $COOnC_4H_9$ |
| 18-147 | F | F | O | H | $COOnC_4H_9$ |
| 18-148 | F | Cl | O | H | $COOnC_4H_9$ |
| 18-149 | Cl | F | O | H | $COOnC_4H_9$ |
| 18-150 | Cl | Cl | O | H | $COOnC_4H_9$ |

TABLE 76

| | X | Y | Z² | R¹ | R⁶ |
|---|---|---|---|---|---|
| 18-151 | H | F | O | H | $COOnC_5H_{11}$ |
| 18-152 | H | Cl | O | H | $COOnC_5H_{11}$ |
| 18-153 | F | F | O | H | $COOnC_5H_{11}$ |
| 18-154 | F | Cl | O | H | $COOnC_5H_{11}$ |
| 18-155 | Cl | F | O | H | $COOnC_5H_{11}$ |
| 18-156 | Cl | Cl | O | H | $COOnC_5H_{11}$ |
| 18-157 | H | F | O | H | $COOiC_3H_7$ |
| 18-158 | H | Cl | O | H | $COOiC_3H_7$ |
| 18-159 | F | F | O | H | $COOiC_3H_7$ |
| 18-160 | F | Cl | O | H | $COOiC_3H_7$ |

TABLE 76-continued

|  | X | Y | $Z^2$ | $R^1$ | $R^6$ |
|---|---|---|---|---|---|
| 18-161 | Cl | F | O | H | $COOiC_3H_7$ |
| 18-162 | Cl | Cl | O | H | $COOiC_3H_7$ |

Compounds of the general formula:

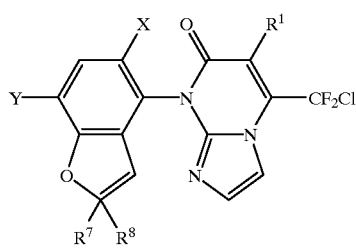

TABLE 77

|  | X | Y | $R^1$ | $R^7$ | $R^8$ |
|---|---|---|---|---|---|
| 19-1 | H | F | H | H | $CH_3$ |
| 19-2 | H | Cl | H | H | $CH_3$ |
| 19-3 | H | Br | H | H | $CH_3$ |
| 19-4 | F | F | H | H | $CH_3$ |
| 19-5 | F | Cl | H | H | $CH_3$ |
| 19-6 | F | Br | H | H | $CH_3$ |
| 19-7 | Cl | F | H | H | $CH_3$ |
| 19-8 | Cl | Cl | H | H | $CH_3$ |
| 19-9 | Cl | Br | H | H | $CH_3$ |
| 19-10 | H | F | H | H | $CH_2OH$ |
| 19-11 | H | Cl | H | H | $CH_2OH$ |
| 19-12 | H | Br | H | H | $CH_2OH$ |
| 19-13 | F | F | H | H | $CH_2OH$ |
| 19-14 | F | Cl | H | H | $CH_2OH$ |
| 19-15 | F | Br | H | H | $CH_2OH$ |
| 19-16 | Cl | F | H | H | $CH_2OH$ |
| 19-17 | Cl | Cl | H | H | $CH_2OH$ |
| 19-18 | Cl | Br | H | H | $CH_2OH$ |
| 19-19 | H | F | H | H | $CH_2Cl$ |
| 19-20 | H | Cl | H | H | $CH_2Cl$ |
| 19-21 | F | F | H | H | $CH_2Cl$ |
| 19-22 | F | Cl | H | H | $CH_2Cl$ |
| 19-23 | Cl | F | H | H | $CH_2Cl$ |
| 19-24 | Cl | Cl | H | H | $CH_2Cl$ |
| 19-25 | H | F | H | H | $CH_2Br$ |

TABLE 78

|  | X | Y | $R^1$ | $R^7$ | $R^8$ |
|---|---|---|---|---|---|
| 19-26 | H | Cl | H | H | $CH_2Br$ |
| 19-27 | F | F | H | H | $CH_2Br$ |
| 19-28 | F | Cl | H | H | $CH_2Br$ |
| 19-29 | Cl | F | H | H | $CH_2Br$ |
| 19-30 | Cl | Cl | H | H | $CH_2Br$ |
| 19-31 | H | F | H | H | $CH_2OCH_3$ |
| 19-32 | H | Cl | H | H | $CH_2OCH_3$ |
| 19-33 | F | F | H | H | $CH_2OCH_3$ |
| 19-34 | F | Cl | H | H | $CH_2OCH_3$ |
| 19-35 | Cl | F | H | H | $CH_2OCH_3$ |
| 19-36 | Cl | Cl | H | H | $CH_2OCH_3$ |
| 19-37 | H | F | H | H | $CH_2OC_2H_5$ |
| 19-38 | H | Cl | H | H | $CH_2OC_2H_5$ |
| 19-39 | F | F | H | H | $CH_2OC_2H_5$ |
| 19-40 | F | Cl | H | H | $CH_2OC_2H_5$ |
| 19-41 | Cl | F | H | H | $CH_2OC_2H_5$ |
| 19-42 | Cl | Cl | H | H | $CH_2OC_2H_5$ |
| 19-43 | H | F | H | H | $CH_2OiC_3H_7$ |
| 19-44 | H | Cl | H | H | $CH_2OiC_3H_7$ |

TABLE 78-continued

|  | X | Y | $R^1$ | $R^7$ | $R^8$ |
|---|---|---|---|---|---|
| 19-45 | F | F | H | H | $CH_2OiC_3H_7$ |
| 19-46 | F | Cl | H | H | $CH_2OiC_3H_7$ |
| 19-47 | Cl | F | H | H | $CH_2OiC_3H_7$ |
| 19-48 | Cl | Cl | H | H | $CH_2OiC_3H_7$ |
| 19-49 | H | F | H | H | $CH_2OCH_2OCH_3$ |
| 19-50 | H | Cl | H | H | $CH_2OCH_2OCH_3$ |

TABLE 79

|  | X | Y | $R^1$ | $R^7$ | $R^8$ |
|---|---|---|---|---|---|
| 19-51 | F | F | H | H | $CH_2OCH_2OCH_3$ |
| 19-52 | F | Cl | H | H | $CH_2OCH_2OCH_3$ |
| 19-53 | Cl | F | H | H | $CH_2OCH_2OCH_3$ |
| 19-54 | Cl | Cl | H | H | $CH_2OCH_2OCH_3$ |
| 19-55 | H | F | H | H | $CH_2OCH_2OC_2H_5$ |
| 19-56 | H | Cl | H | H | $CH_2OCH_2OC_2H_5$ |
| 19-57 | F | F | H | H | $CH_2OCH_2OC_2H_5$ |
| 19-58 | F | Cl | H | H | $CH_2OCH_2OC_2H_5$ |
| 19-59 | Cl | F | H | H | $CH_2OCH_2OC_2H_5$ |
| 19-60 | Cl | Cl | H | H | $CH_2OCH_2OC_2H_5$ |
| 19-61 | H | F | H | H | $CH_2OCOCH_3$ |
| 19-62 | H | Cl | H | H | $CH_2OCOCH_3$ |
| 19-63 | F | F | H | H | $CH_2OCOCH_3$ |
| 19-64 | F | Cl | H | H | $CH_2OCOCH_3$ |
| 19-65 | Cl | F | H | H | $CH_2OCOCH_3$ |
| 19-66 | Cl | Cl | H | H | $CH_2OCOCH_3$ |
| 19-67 | H | F | H | H | $CH_2OCOC_2H_5$ |
| 19-68 | H | Cl | H | H | $CH_2OCOC_2H_5$ |
| 19-69 | F | F | H | H | $CH_2OCOC_2H_5$ |
| 19-70 | F | Cl | H | H | $CH_2OCOC_2H_5$ |
| 19-71 | Cl | F | H | H | $CH_2OCOC_2H_5$ |
| 19-72 | Cl | Cl | H | H | $CH_2OCOC_2H_5$ |
| 19-73 | H | F | H | H | $CH_2OCOiC_3H_7$ |
| 19-74 | H | Cl | H | H | $CH_2OCOiC_3H_7$ |
| 19-75 | F | F | H | H | $CH_2OCOiC_3H_7$ |

TABLE 80

|  | X | Y | $R^1$ | $R^7$ | $R^8$ |
|---|---|---|---|---|---|
| 19-76 | F | Cl | H | H | $CH_2OCOiC_3H_7$ |
| 19-77 | Cl | F | H | H | $CH_2OCOiC_3H_7$ |
| 19-78 | Cl | Cl | H | H | $CH_2OCOiC_3H_7$ |
| 19-79 | H | F | H | H | $CH_2OCOCH_2Cl$ |
| 19-80 | H | Cl | H | H | $CH_2OCOCH_2Cl$ |
| 19-81 | F | F | H | H | $CH_2OCOCH_2Cl$ |
| 19-82 | F | Cl | H | H | $CH_2OCOCH_2Cl$ |
| 19-83 | Cl | F | H | H | $CH_2OCOCH_2Cl$ |
| 19-84 | Cl | Cl | H | H | $CH_2OCOCH_2Cl$ |
| 19-85 | H | F | H | H | $CH_2OCOCCl_3$ |
| 19-86 | H | Cl | H | H | $CH_2OCOCCl_3$ |
| 19-87 | F | F | H | H | $CH_2OCOCCl_3$ |
| 19-88 | F | Cl | H | H | $CH_2OCOCCl_3$ |
| 19-89 | Cl | F | H | H | $CH_2OCOCCl_3$ |
| 19-90 | Cl | Cl | H | H | $CH_2OCOCCl_3$ |
| 19-91 | H | F | H | H | $CH_2OCOCF_3$ |
| 19-92 | H | Cl | H | H | $CH_2OCOCF_3$ |
| 19-93 | F | F | H | H | $CH_2OCOCF_3$ |
| 19-94 | F | Cl | H | H | $CH_2OCOCF_3$ |
| 19-95 | Cl | F | H | H | $CH_2OCOCF_3$ |
| 19-96 | Cl | Cl | H | H | $CH_2OCOCF_3$ |
| 19-97 | H | F | H | H | COOH |
| 19-98 | H | Cl | H | H | COOH |
| 19-99 | F | F | H | H | COOH |
| 19-100 | F | Cl | H | H | COOH |

TABLE 81

|  | X | Y | R¹ | R⁷ | R⁸ |
|---|---|---|---|---|---|
| 19-101 | Cl | F | H | H | COOH |
| 19-102 | Cl | Cl | H | H | COOH |
| 19-103 | H | F | H | H | COOCH$_3$ |
| 19-104 | H | Cl | H | H | COOCH$_3$ |
| 19-105 | F | F | H | H | COOCH$_3$ |
| 19-106 | F | Cl | H | H | COOCH$_3$ |
| 19-107 | Cl | F | H | H | COOCH$_3$ |
| 19-108 | Cl | Cl | H | H | COOCH$_3$ |
| 19-109 | H | F | H | H | COOC$_2$H$_5$ |
| 19-110 | H | Cl | H | H | COOC$_2$H$_5$ |
| 19-111 | F | F | H | H | COOC$_2$H$_5$ |
| 19-112 | F | Cl | H | H | COOC$_2$H$_5$ |
| 19-113 | Cl | F | H | H | COOC$_2$H$_5$ |
| 19-114 | Cl | Cl | H | H | COOC$_2$H$_5$ |
| 19-115 | H | F | H | H | COOnC$_3$H$_7$ |
| 19-116 | H | Cl | H | H | COOnC$_3$H$_7$ |
| 19-117 | F | F | H | H | COOnC$_3$H$_7$ |
| 19-118 | F | Cl | H | H | COOnC$_3$H$_7$ |
| 19-119 | Cl | F | H | H | COOnC$_3$H$_7$ |
| 19-120 | Cl | Cl | H | H | COOnC$_3$H$_7$ |
| 19-121 | H | F | H | H | COOnC$_4$H$_9$ |
| 19-122 | H | Cl | H | H | COOnC$_4$H$_9$ |
| 19-123 | F | F | H | H | COOnC$_4$H$_9$ |
| 19-124 | F | Cl | H | H | COOnC$_4$H$_9$ |
| 19-125 | Cl | F | H | H | COOnC$_4$H$_9$ |

TABLE 82

|  | X | Y | R¹ | R⁷ | R⁸ |
|---|---|---|---|---|---|
| 19-126 | Cl | Cl | H | H | COOnC$_4$H$_9$ |
| 19-127 | H | F | H | H | COOnC$_5$H$_{11}$ |
| 19-128 | H | Cl | H | H | COOnC$_5$H$_{11}$ |
| 19-129 | F | F | H | H | COOnC$_5$H$_{11}$ |
| 19-130 | F | Cl | H | H | COOnC$_5$H$_{11}$ |
| 19-131 | Cl | F | H | H | COOnC$_5$H$_{11}$ |
| 19-132 | Cl | Cl | H | H | COOnC$_5$H$_{11}$ |
| 19-133 | H | F | H | H | COOiC$_3$H$_7$ |
| 19-134 | H | Cl | H | H | COOiC$_3$H$_7$ |
| 19-135 | F | F | H | H | COOiC$_3$H$_7$ |
| 19-136 | F | Cl | H | H | COOiC$_3$H$_7$ |
| 19-137 | Cl | F | H | H | COOiC$_3$H$_7$ |
| 19-138 | Cl | Cl | H | H | COOiC$_3$H$_7$ |
| 19-139 | H | F | H | H | COOcC$_5$H$_9$ |
| 19-140 | H | Cl | H | H | COOcC$_5$H$_9$ |
| 19-141 | F | F | H | H | COOcC$_5$H$_9$ |
| 19-142 | F | Cl | H | H | COOcC$_5$H$_9$ |
| 19-143 | Cl | F | H | H | COOcC$_5$H$_9$ |
| 19-144 | Cl | Cl | H | H | COOcC$_5$H$_9$ |
| 19-145 | H | F | H | H | COOcC$_6$H$_{11}$ |
| 19-146 | H | Cl | H | H | COOcC$_6$H$_{11}$ |
| 19-147 | F | F | H | H | COOcC$_6$H$_{11}$ |
| 19-148 | F | Cl | H | H | COOcC$_6$H$_{11}$ |
| 19-149 | Cl | F | H | H | COOcC$_6$H$_{11}$ |
| 19-150 | Cl | Cl | H | H | COOcC$_6$H$_{11}$ |

TABLE 83

|  | X | Y | R¹ | R⁷ | R⁸ |
|---|---|---|---|---|---|
| 19-151 | H | F | H | H | COOCH$_2$CH=CH$_2$ |
| 19-152 | H | Cl | H | H | COOCH$_2$CH=CH$_2$ |
| 19-153 | F | F | H | H | COOCH$_2$CH=CH$_2$ |
| 19-154 | F | Cl | H | H | COOCH$_2$CH=CH$_2$ |
| 19-155 | Cl | F | H | H | COOCH$_2$CH=CH$_2$ |
| 19-156 | Cl | Cl | H | H | COOCH$_2$CH=CH$_2$ |
| 19-157 | H | F | H | H | COOCH$_2$C≡CH |
| 19-158 | H | Cl | H | H | COOCH$_2$C≡CH |
| 19-159 | F | F | H | H | COOCH$_2$C≡CH |
| 19-160 | F | Cl | H | H | COOCH$_2$C≡CH |
| 19-161 | Cl | F | H | H | COOCH$_2$C≡CH |
| 19-162 | Cl | Cl | H | H | COOCH$_2$C≡CH |

TABLE 83-continued

|  | X | Y | R¹ | R⁷ | R⁸ |
|---|---|---|---|---|---|
| 19-163 | H | F | H | H | CONH$_2$ |
| 19-164 | H | Cl | H | H | CONH$_2$ |
| 19-165 | F | F | H | H | CONH$_2$ |
| 19-166 | F | Cl | H | H | CONH$_2$ |
| 19-167 | Cl | F | H | H | CONH$_2$ |
| 19-168 | Cl | Cl | H | H | CONH$_2$ |
| 19-169 | H | F | H | H | CONHCH$_3$ |
| 19-170 | H | Cl | H | H | CONHCH$_3$ |
| 19-171 | F | F | H | H | CONHCH$_3$ |
| 19-172 | F | Cl | H | H | CONHCH$_3$ |
| 19-173 | Cl | F | H | H | CONHCH$_3$ |
| 19-174 | Cl | Cl | H | H | CONHCH$_3$ |
| 19-175 | H | F | H | H | CONHC$_2$H$_5$ |

TABLE 84

|  | X | Y | R¹ | R⁷ | R⁸ |
|---|---|---|---|---|---|
| 19-176 | H | Cl | H | H | CONHC$_2$H$_5$ |
| 19-177 | F | F | H | H | CONHC$_2$H$_5$ |
| 19-178 | F | Cl | H | H | CONHC$_2$H$_5$ |
| 19-179 | Cl | F | H | H | CONHC$_2$H$_5$ |
| 19-180 | Cl | Cl | H | H | CONHC$_2$H$_5$ |
| 19-181 | H | F | H | H | CON(CH$_3$)$_2$ |
| 19-182 | H | Cl | H | H | CON(CH$_3$)$_2$ |
| 19-183 | F | F | H | H | CON(CH$_3$)$_2$ |
| 19-184 | F | Cl | H | H | CON(CH$_3$)$_2$ |
| 19-185 | Cl | F | H | H | CON(CH$_3$)$_2$ |
| 19-186 | Cl | Cl | H | H | CON(CH$_3$)$_2$ |
| 19-187 | H | F | H | H | CON(C$_2$H$_5$)$_2$ |
| 19-188 | H | Cl | H | H | CON(C$_2$H$_5$)$_2$ |
| 19-189 | F | F | H | H | CON(C$_2$H$_5$)$_2$ |
| 19-190 | F | Cl | H | H | CON(C$_2$H$_5$)$_2$ |
| 19-191 | Cl | F | H | H | CON(C$_2$H$_5$)$_2$ |
| 19-192 | Cl | Cl | H | H | CON(C$_2$H$_5$)$_2$ |
| 19-193 | H | F | H | CH$_3$ | CH$_3$ |
| 19-194 | H | Cl | H | CH$_3$ | CH$_3$ |
| 19-195 | H | Br | H | CH$_3$ | CH$_3$ |
| 19-196 | F | F | H | CH$_3$ | CH$_3$ |
| 19-197 | F | Cl | H | CH$_3$ | CH$_3$ |
| 19-198 | F | Br | H | CH$_3$ | CH$_3$ |
| 19-199 | Cl | F | H | CH$_3$ | CH$_3$ |
| 19-200 | Cl | Cl | H | CH$_3$ | CH$_3$ |

TABLE 85

|  | X | Y | R¹ | R⁷ | R⁸ |
|---|---|---|---|---|---|
| 19-201 | Cl | Br | H | CH$_3$ | CH$_3$ |
| 19-202 | H | F | H | CH$_3$ | CH$_2$OH |
| 19-203 | H | Cl | H | CH$_3$ | CH$_2$OH |
| 19-204 | H | Br | H | CH$_3$ | CH$_2$OH |
| 19-205 | F | F | H | CH$_3$ | CH$_2$OH |
| 19-206 | F | Cl | H | CH$_3$ | CH$_2$OH |
| 19-207 | F | Br | H | CH$_3$ | CH$_2$OH |
| 19-208 | Cl | F | H | CH$_3$ | CH$_2$OH |
| 19-209 | Cl | Cl | H | CH$_3$ | CH$_2$OH |
| 19-210 | Cl | Br | H | CH$_3$ | CH$_2$OH |
| 19-211 | H | F | H | CH$_3$ | CH$_2$Cl |
| 19-212 | H | Cl | H | CH$_3$ | CH$_2$Cl |
| 19-213 | F | F | H | CH$_3$ | CH$_2$Cl |
| 19-214 | F | Cl | H | CH$_3$ | CH$_2$Cl |
| 19-215 | Cl | F | H | CH$_3$ | CH$_2$Cl |
| 19-216 | Cl | Cl | H | CH$_3$ | CH$_2$Cl |
| 19-217 | H | F | H | CH$_3$ | CH$_2$Br |
| 19-218 | H | Cl | H | CH$_3$ | CH$_2$Br |
| 19-219 | F | F | H | CH$_3$ | CH$_2$Br |
| 19-220 | F | Cl | H | CH$_3$ | CH$_2$Br |
| 19-221 | Cl | F | H | CH$_3$ | CH$_2$Br |
| 19-222 | Cl | Cl | H | CH$_3$ | CH$_2$Br |
| 19-223 | H | F | H | CH$_3$ | CH$_2$OCH$_3$ |

TABLE 85-continued

|  | X | Y | $R^1$ | $R^7$ | $R^8$ |
|---|---|---|---|---|---|
| 19-224 | H | Cl | H | $CH_3$ | $CH_2OCH_3$ |
| 19-225 | F | F | H | $CH_3$ | $CH_2OCH_3$ |

TABLE 86

|  | X | Y | $R^1$ | $R^7$ | $R^8$ |
|---|---|---|---|---|---|
| 19-226 | F | Cl | H | $CH_3$ | $CH_2OCH_3$ |
| 19-227 | Cl | F | H | $CH_3$ | $CH_2OCH_3$ |
| 19-228 | Cl | Cl | H | $CH_3$ | $CH_2OCH_3$ |
| 19-229 | H | F | H | $CH_3$ | $CH_2OC_2H_5$ |
| 19-230 | H | Cl | H | $CH_3$ | $CH_2OC_2H_5$ |
| 19-231 | F | F | H | $CH_3$ | $CH_2OC_2H_5$ |
| 19-232 | F | Cl | H | $CH_3$ | $CH_2OC_2H_5$ |
| 19-233 | Cl | F | H | $CH_3$ | $CH_2OC_2H_5$ |
| 19-234 | Cl | Cl | H | $CH_3$ | $CH_2OC_2H_5$ |
| 19-235 | H | F | H | $CH_3$ | $CH_2OiC_3H_7$ |
| 19-236 | H | Cl | H | $CH_3$ | $CH_2OiC_3H_7$ |
| 19-237 | F | F | H | $CH_3$ | $CH_2OiC_3H_7$ |
| 19-238 | F | Cl | H | $CH_3$ | $CH_2OiC_3H_7$ |
| 19-239 | Cl | F | H | $CH_3$ | $CH_2OiC_3H_7$ |
| 19-240 | Cl | Cl | H | $CH_3$ | $CH_2OiC_3H_7$ |
| 19-241 | H | F | H | $CH_3$ | $CH_2OCH_2OCH_3$ |
| 19-242 | H | Cl | H | $CH_3$ | $CH_2OCH_2OCH_3$ |
| 19-243 | F | F | H | $CH_3$ | $CH_2OCH_2OCH_3$ |
| 19-244 | F | Cl | H | $CH_3$ | $CH_2OCH_2OCH_3$ |
| 19-245 | Cl | F | H | $CH_3$ | $CH_2OCH_2OCH_3$ |
| 19-246 | Cl | Cl | H | $CH_3$ | $CH_2OCH_2OCH_3$ |
| 19-247 | H | F | H | $CH_3$ | $CH_2OCH_2OC_2H_5$ |
| 19-248 | H | Cl | H | $CH_3$ | $CH_2OCH_2OC_2H_5$ |
| 19-249 | F | F | H | $CH_3$ | $CH_2OCH_2OC_2H_5$ |
| 19-250 | F | Cl | H | $CH_3$ | $CH_2OCH_2OC_2H_5$ |

TABLE 87

|  | X | Y | $R^1$ | $R^7$ | $R^8$ |
|---|---|---|---|---|---|
| 19-251 | Cl | F | H | $CH_3$ | $CH_2OCH_2OC_2H_5$ |
| 19-252 | Cl | Cl | H | $CH_3$ | $CH_2OCH_2OC_2H_5$ |
| 19-253 | H | F | H | $CH_3$ | $CH_2OCOCH_3$ |
| 19-254 | H | Cl | H | $CH_3$ | $CH_2OCOCH_3$ |
| 19-255 | F | F | H | $CH_3$ | $CH_2OCOCH_3$ |
| 19-256 | F | Cl | H | $CH_3$ | $CH_2OCOCH_3$ |
| 19-257 | Cl | F | H | $CH_3$ | $CH_2OCOCH_3$ |
| 19-258 | Cl | Cl | H | $CH_3$ | $CH_2OCOCH_3$ |
| 19-259 | H | F | H | $CH_3$ | $CH_2OCOC_2H_5$ |
| 19-260 | H | Cl | H | $CH_3$ | $CH_2OCOC_2H_5$ |
| 19-261 | F | F | H | $CH_3$ | $CH_2OCOC_2H_5$ |
| 19-262 | F | Cl | H | $CH_3$ | $CH_2OCOC_2H_5$ |
| 19-263 | Cl | F | H | $CH_3$ | $CH_2OCOC_2H_5$ |
| 19-264 | Cl | Cl | H | $CH_3$ | $CH_2OCOC_2H_5$ |
| 19-265 | H | F | H | $CH_3$ | $CH_2OCOiC_3H_7$ |
| 19-266 | H | Cl | H | $CH_3$ | $CH_2OCOiC_3H_7$ |
| 19-267 | F | F | H | $CH_3$ | $CH_2OCOiC_3H_7$ |
| 19-268 | F | Cl | H | $CH_3$ | $CH_2OCOiC_3H_7$ |
| 19-269 | Cl | F | H | $CH_3$ | $CH_2OCOiC_3H_7$ |
| 19-270 | Cl | Cl | H | $CH_3$ | $CH_2OCOiC_3H_7$ |
| 19-271 | H | F | H | $CH_3$ | $CH_2OCOCH_2Cl$ |
| 19-272 | H | Cl | H | $CH_3$ | $CH_2OCOCH_2Cl$ |
| 19-273 | F | F | H | $CH_3$ | $CH_2OCOCH_2Cl$ |
| 19-274 | F | Cl | H | $CH_3$ | $CH_2OCOCH_2Cl$ |
| 19-275 | Cl | F | H | $CH_3$ | $CH_2OCOCH_2Cl$ |

TABLE 88

|  | X | Y | $R^1$ | $R^7$ | $R^8$ |
|---|---|---|---|---|---|
| 19-276 | Cl | Cl | H | $CH_3$ | $CH_2OCOCH_2Cl$ |
| 19-277 | H | F | H | $CH_3$ | $CH_2OCOCCl_3$ |
| 19-278 | H | Cl | H | $CH_3$ | $CH_2OCOCCl_3$ |

TABLE 88-continued

|  | X | Y | $R^1$ | $R^7$ | $R^8$ |
|---|---|---|---|---|---|
| 19-279 | F | F | H | $CH_3$ | $CH_2OCOCCl_3$ |
| 19-280 | F | Cl | H | $CH_3$ | $CH_2OCOCCl_3$ |
| 19-281 | Cl | F | H | $CH_3$ | $CH_2OCOCCl_3$ |
| 19-282 | Cl | Cl | H | $CH_3$ | $CH_2OCOCCl_3$ |
| 19-283 | H | F | H | $CH_3$ | $CH_2OCOCF_3$ |
| 19-284 | H | Cl | H | $CH_3$ | $CH_2OCOCF_3$ |
| 19-285 | F | F | H | $CH_3$ | $CH_2OCOCF_3$ |
| 19-286 | F | Cl | H | $CH_3$ | $CH_2OCOCF_3$ |
| 19-287 | Cl | F | H | $CH_3$ | $CH_2OCOCF_3$ |
| 19-288 | Cl | Cl | H | $CH_3$ | $CH_2OCOCF_3$ |
| 19-289 | H | F | H | $CH_3$ | COOH |
| 19-290 | H | Cl | H | $CH_3$ | COOH |
| 19-291 | F | F | H | $CH_3$ | COOH |
| 19-292 | F | Cl | H | $CH_3$ | COOH |
| 19-293 | Cl | F | H | $CH_3$ | COOH |
| 19-294 | Cl | Cl | H | $CH_3$ | COOH |
| 19-295 | H | F | H | $CH_3$ | $COOCH_3$ |
| 19-296 | H | Cl | H | $CH_3$ | $COOCH_3$ |
| 19-297 | F | F | H | $CH_3$ | $COOCH_3$ |
| 19-298 | F | Cl | H | $CH_3$ | $COOCH_3$ |
| 19-299 | Cl | F | H | $CH_3$ | $COOCH_3$ |
| 19-300 | Cl | Cl | H | $CH_3$ | $COOCH_3$ |

TABLE 89

|  | X | Y | $R^1$ | $R^7$ | $R^8$ |
|---|---|---|---|---|---|
| 19-301 | H | F | H | $CH_3$ | $COOC_2H_5$ |
| 19-302 | H | Cl | H | $CH_3$ | $COOC_2H_5$ |
| 19-303 | F | F | H | $CH_3$ | $COOC_2H_5$ |
| 19-304 | F | Cl | H | $CH_3$ | $COOC_2H_5$ |
| 19-305 | Cl | F | H | $CH_3$ | $COOC_2H_5$ |
| 19-306 | Cl | Cl | H | $CH_3$ | $COOC_2H_5$ |
| 19-307 | H | F | H | $CH_3$ | $COOnC_3H_7$ |
| 19-308 | H | Cl | H | $CH_3$ | $COOnC_3H_7$ |
| 19-309 | F | F | H | $CH_3$ | $COOnC_3H_7$ |
| 19-310 | F | Cl | H | $CH_3$ | $COOnC_3H_7$ |
| 19-311 | Cl | F | H | $CH_3$ | $COOnC_3H_7$ |
| 19-312 | Cl | Cl | H | $CH_3$ | $COOnC_3H_7$ |
| 19-313 | H | F | H | $CH_3$ | $COOnC_4H_9$ |
| 19-314 | H | Cl | H | $CH_3$ | $COOnC_4H_9$ |
| 19-315 | F | F | H | $CH_3$ | $COOnC_4H_9$ |
| 19-316 | F | Cl | H | $CH_3$ | $COOnC_4H_9$ |
| 19-317 | Cl | F | H | $CH_3$ | $COOnC_4H_9$ |
| 19-318 | Cl | Cl | H | $CH_3$ | $COOnC_4H_9$ |
| 19-319 | H | F | H | $CH_3$ | $COOnC_5H_{11}$ |
| 19-320 | H | Cl | H | $CH_3$ | $COOnC_5H_{11}$ |
| 19-321 | F | F | H | $CH_3$ | $COOnC_5H_{11}$ |
| 19-322 | F | Cl | H | $CH_3$ | $COOnC_5H_{11}$ |
| 19-323 | Cl | F | H | $CH_3$ | $COOnC_5H_{11}$ |
| 19-324 | Cl | Cl | H | $CH_3$ | $COOnC_5H_{11}$ |
| 19-325 | H | F | H | $CH_3$ | $COOiC_3H_7$ |

TABLE 90

|  | X | Y | $R^1$ | $R^7$ | $R^8$ |
|---|---|---|---|---|---|
| 19-326 | H | Cl | H | $CH_3$ | $COOiC_3H_7$ |
| 19-327 | F | F | H | $CH_3$ | $COOiC_3H_7$ |
| 19-328 | F | Cl | H | $CH_3$ | $COOiC_3H_7$ |
| 19-329 | Cl | F | H | $CH_3$ | $COOiC_3H_7$ |
| 19-330 | Cl | Cl | H | $CH_3$ | $COOiC_3H_7$ |
| 19-331 | H | F | H | $CH_3$ | $COOcC_5H_9$ |
| 19-332 | H | Cl | H | $CH_3$ | $COOcC_5H_9$ |
| 19-333 | F | F | H | $CH_3$ | $COOcC_5H_9$ |
| 19-334 | F | Cl | H | $CH_3$ | $COOcC_5H_9$ |
| 19-335 | Cl | F | H | $CH_3$ | $COOcC_5H_9$ |
| 19-336 | Cl | Cl | H | $CH_3$ | $COOcC_5H_9$ |
| 19-337 | H | F | H | $CH_3$ | $COOcC_6H_{11}$ |
| 19-338 | H | Cl | H | $CH_3$ | $COOcC_6H_{11}$ |
| 19-339 | F | F | H | $CH_3$ | $COOcC_6H_{11}$ |
| 19-340 | F | Cl | H | $CH_3$ | $COOcC_6H_{11}$ |

TABLE 90-continued

| | X | Y | R¹ | R⁷ | R⁸ |
|---|---|---|---|---|---|
| 19-341 | Cl | F | H | CH₃ | COOcC₆H₁₁ |
| 19-342 | Cl | Cl | H | CH₃ | COOcC₆H₁₁ |
| 19-343 | H | F | H | CH₃ | COOCH₂CH=CH₂ |
| 19-344 | H | Cl | H | CH₃ | COOCH₂CH=CH₂ |
| 19-345 | F | F | H | CH₃ | COOCH₂CH=CH₂ |
| 19-346 | F | Cl | H | CH₃ | COOCH₂CH=CH₂ |
| 19-347 | Cl | F | H | CH₃ | COOCH₂CH=CH₂ |
| 19-348 | Cl | Cl | H | CH₃ | COOCH₂CH=CH₂ |
| 19-349 | H | F | H | CH₃ | COOCH₂C≡CH |
| 19-350 | H | Cl | H | CH₃ | COOCH₂C≡CH |

TABLE 91

| | X | Y | R¹ | R⁷ | R⁸ |
|---|---|---|---|---|---|
| 19-351 | F | F | H | CH₃ | COOCH₂C≡CH |
| 19-352 | F | Cl | H | CH₃ | COOCH₂C≡CH |
| 19-353 | Cl | F | H | CH₃ | COOCH₂C≡CH |
| 19-354 | Cl | Cl | H | CH₃ | COOCH₂C≡CH |
| 19-355 | H | F | H | CH₃ | CONH₂ |
| 19-356 | H | Cl | H | CH₃ | CONH₂ |
| 19-357 | F | F | H | CH₃ | CONH₂ |
| 19-358 | F | Cl | H | CH₃ | CONH₂ |
| 19-359 | Cl | F | H | CH₃ | CONH₂ |
| 19-360 | Cl | Cl | H | CH₃ | CONH₂ |
| 19-361 | H | F | H | CH₃ | CONHCH₃ |
| 19-362 | H | Cl | H | CH₃ | CONHCH₃ |
| 19-363 | F | F | H | CH₃ | CONHCH₃ |
| 19-364 | F | Cl | H | CH₃ | CONHCH₃ |
| 19-365 | Cl | F | H | CH₃ | CONHCH₃ |
| 19-366 | Cl | Cl | H | CH₃ | CONHCH₃ |
| 19-367 | H | F | H | CH₃ | CONHC₂H₅ |
| 19-368 | H | Cl | H | CH₃ | CONHC₂H₅ |
| 19-369 | F | F | H | CH₃ | CONHC₂H₅ |
| 19-370 | F | Cl | H | CH₃ | CONHC₂H₅ |
| 19-371 | Cl | F | H | CH₃ | CONHC₂H₅ |
| 19-372 | Cl | Cl | H | CH₃ | CONHC₂H₅ |
| 19-373 | H | F | H | CH₃ | CON(CH₃)₂ |
| 19-374 | H | Cl | H | CH₃ | CON(CH₃)₂ |
| 19-375 | F | F | H | CH₃ | CON(CH₃)₂ |

TABLE 92

| | X | Y | R¹ | R⁷ | R⁸ |
|---|---|---|---|---|---|
| 19-376 | F | Cl | H | CH₃ | CON(CH₃)₂ |
| 19-377 | Cl | F | H | CH₃ | CON(CH₃)₂ |
| 19-378 | Cl | Cl | H | CH₃ | CON(CH₃)₂ |
| 19-379 | H | F | H | CH₃ | CON(C₂H₅)₂ |
| 19-380 | H | Cl | H | CH₃ | CON(C₂H₅)₂ |
| 19-381 | F | F | H | CH₃ | CON(C₂H₅)₂ |
| 19-382 | F | Cl | H | CH₃ | CON(C₂H₅)₂ |
| 19-383 | Cl | F | H | CH₃ | CON(C₂H₅)₂ |
| 19-384 | Cl | Cl | H | CH₃ | CON(C₂H₅)₂ |

The following are formulation examples for the present compounds. In these example, the present compounds are designated by their compound numbers shown in Tables 1 to 92 and parts are by weight.

Formulation Example 1

Fifty parts of each of the present compounds 8-5, 9-14, 9-206, 9-298, and 9-304, 3 parts of calcium lignin sulfonate, 2 parts of sodium laurylsulfate, and 45 parts of synthetic hydrated silicon oxide are well pulverized and mixed to give a wettable powder for each compound.

Formulation Example 2

Ten parts of each of the present compounds 8-5, 9-14, 9-206, 9-298, and 9-304, 14 parts of polyoxyethylene styryl phenyl ether, 6 parts of calcium dodecylbenzenesulfonate, 35 parts of xylene, and 35 parts of cyclohexanone are well mixed to give an emulsifiable concentrate for each compound.

Formulation Example 3

Two parts of the present compounds 8-5, 9-14, 9-206, 9-298, and 9-304, 2 parts of synthetic hydrated silicon oxide, 2 parts of calcium lignin sulfonate, 30 parts of bentonite, and 64 parts of kaolin clay are well pulverized and mixed. The mixture is well kneaded with the addition of water, and then granulated and dried to give a granule for each compound.

Formulation Example 4

Twenty-five parts of the present compounds 8-5, 9-14, 9-206, 9-298, and 9-304, 50 parts of 10% aqueous polyvinyl alcohol solution, and 25 parts of water are mixed and then wet pulverized until the mean particle size comes to 5 μm or smaller to give a flowable for each compound.

Formulation Example 5

Five parts of the present compounds 8-5, 9-14, 9-206, 9-298, and 9-304, is added to 40 parts of 10% aqueous polyvinyl alcohol solution and dispersed therein by emulsification with a homogenizer until the mean particle size comes to 10 μm or smaller, and 55 parts of water is added to give a thick emulsion for each compound.

The following test example will demonstrate that the present compounds are useful as the active ingredients of herbicides. In this example, the present compounds are designated by their compound numbers shown in Tables 1 to 92.

Test Example Foliar treatment on upland fields

Cylindrical plastic pots each having a diameter of 10 cm and a depth of 10 cm were filled with soil and then seeded with ivyleaf morningglory (*Ipomoea hederacea*) and velvetleaf (*Abutilon theoplrasti*). These test plants were grown in a greenhouse for 19 days. Each of the test compounds listed below was formulated into an emulsifiable concentrate according to Formulation Example 2 and then diluted in its prescribed amount with water containing a spreading agent. The dilution was uniformly sprayed over the foliage of the test plants with a sprayer at a rate of 1000 liters per hectare After the application, the test plants were grown in the greenhouse for 7 days, and the herbicidal activity was examined. As a result, it was found that present compounds 8-5, 9-14, 9-206, 9-298, and 9-304, made both test plants completely dead in a dosage of 500 g/ha.

We claim:

1. A pyrimidinone compound of the general formula:

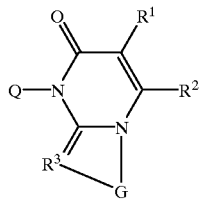

wherein:

R¹ is hydrogen or C₁–C₃ alkyl;
R² is C₁–C₃ haloalkyl;
R³ is nitrogen or CH;

G is any group of the general formula:

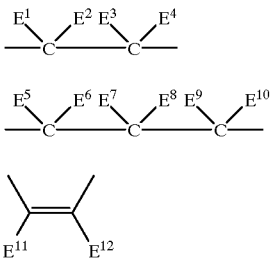

G-1

G-2

G-3 wherein:

$E^1, E^2, E^3, E^4, E^5, E^6, E^7, E^8, E^9, E^{10}, E^{11}$, and $E^{12}$ are independently hydrogen or $C_1$–$C_3$ alkyl; and Q is any group of the general formula:

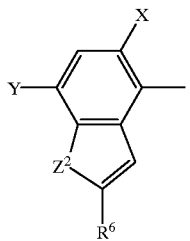

Q-3

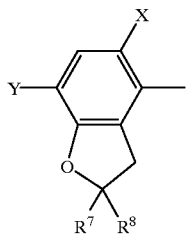

Q-4 wherein:

X is hydrogen or halogen;
Y is halogen, nitro, cyano, or trifluoromethyl;
$Z^2$ is oxygen or sulfur;

$R^6$ is $C_1$–$C_6$ alkyl, $C_1$–$C_6$ haloalkyl, cyano, carboxyl, hydroxy $C_1$–$C_6$ alkyl, $C_1$–$C_6$ alkoxy $C_1$–$C_6$ alkyl, $C_1$–$C_4$ alkylthio $C_1$–$C_4$ alkyl, $C_1$–$C_6$ alkoxy $C_1$–$C_6$ alkoxy $C_1$–$C_6$ alkyl, ($C_1$–$C_6$ alkyl)carbonyloxy $C_1$–$C_6$ alkyl, ($C_1$–$C_6$ haloalkyl)carbonyloxy $C_1$–$C_6$ alkyl, or ($C_1$–$C_6$ alkoxy)carbonyl;

$R^7$ is hydrogen or $C_1$–$C_6$ alkyl; and $R^8$ is $C_1$–$C_6$ alkyl, $C_1$–$C_6$ haloalkyl, hydroxy $C_1$–$C_6$ alkyl, $C_1$–$C_4$ alkoxy $C_1$–$C_4$ alkyl, $C_1$–$C_3$ alkoxy $C_1$–$C_3$ alkoxy $C_1$–$C_3$ alkyl, ($C_1$–$C_6$ alkyl)carbonyloxy $C_1$–$C_6$ alkyl, ($C_1$–$C_6$ haloalkyl)carbonyl $C_1$–$C_6$ alkyl, carboxyl, carboxy $C_1$–$C_6$ alkyl, ($C_1$–$C_8$ alkoxy)carbonyl, ($C_1$–$C_6$ haloalkoxy)carbonyl, ($C_3$–$C_{10}$ cycloalkoxy)carbonyl, ($C_3$–$C_8$ alkenyloxy)carbonyl, ($C_3$–$C_8$ alkynyloxy)carbonyl, ($C_1$–$C_6$ alkyl)aminocarbonyl, di($C_1$–$C_6$ alkyl)aminocarbonyl, ($C_1$–$C_6$ alkyl)aminocarbonyloxy $C_1$–$C_6$ alkyl, or di($C_1$–$C_6$ alkyl)aminocarbonyloxy $C_1$–$C_6$ alkyl.

2. A pyrimidinone compound according to claim 1, wherein Q is Q-3.

3. A pyrimidinone compound according to claim 1, wherein Q is Q-4.

4. A pyrimidinone compound according to claim 1, wherein $R^3$ is nitrogen.

5. A pyrimidinone compound according to claim 1, wherein $R^3$ is CH.

6. A pyrimidinone compound according to claim 1, wherein G is G-1.

7. A pyrimidinone compound according to claim 1, wherein G is G-3.

8. A pyrimidinone compound according to claim 1, wherein $R^2$ is trifluoromethyl.

9. A pyrimidinone compound according to claim 1, wherein $R^2$ is chlorodifluoromethyl.

10. A herbicidal composition a pyrimidinone compound according to claim 1, and an inert carrier or diluent.

11. A method for controlling weeds, which comprises an effective amount of applying a pyrimidinone compound according to claim 1 to an area where the weeds grow or will grow.

12. A method for controlling weeds, which comprises applying an effective amount of a herbicidal composition according to claim 10 to an area where the weeds grow or will grow.

* * * * *